United States Patent
Desrosiers et al.

(10) Patent No.: US 10,544,177 B2
(45) Date of Patent: Jan. 28, 2020

(54) CHIRAL DIHYDROBENZOOXAPHOSPHOLE LIGANDS AND SYNTHESIS THEREOF

(71) Applicant: Boehringer Ingelheim International GmbH, Ingelheim am Rhein (DE)

(72) Inventors: Jean-Nicolas Desrosiers, Southbury, CT (US); Daniel Robert Fandrick, Danbury, CT (US); Nizar Haddad, Danbury, CT (US); Guisheng Li, Danbury, CT (US); Nitinchandra D. Patel, Danbury, CT (US); Bo Qu, Brookfield, CT (US); Sonia Rodriguez, New Milford, CT (US); Chris Hugh Senanayake, Brookfield, CT (US); Joshua Daniel Sieber, Sandy Hook, CT (US); Zhulin Tan, Cheshire, CT (US); Xiao-Jun Wang, Ridgefield, CT (US); Nathan K. Yee, Danbury, CT (US); Li Zhang, New Milford, CT (US); Yongda Zhang, Sandy Hook, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/244,950

(22) Filed: Jan. 10, 2019

(65) Prior Publication Data

US 2019/0144475 A1   May 16, 2019

Related U.S. Application Data

(62) Division of application No. 15/832,799, filed on Dec. 6, 2017, now Pat. No. 10,221,203.

(60) Provisional application No. 62/430,376, filed on Dec. 6, 2016.

(51) Int. Cl.
| | | |
|---|---|---|
| C07F 9/6571 | (2006.01) | |
| C07B 53/00 | (2006.01) | |
| C07F 15/00 | (2006.01) | |
| C07F 9/6568 | (2006.01) | |

(52) U.S. Cl.
CPC ............ *C07F 9/6571* (2013.01); *C07B 53/00* (2013.01); *C07F 9/65683* (2013.01); *C07F 9/65685* (2013.01); *C07F 15/006* (2013.01); *C07F 15/0033* (2013.01)

(58) Field of Classification Search
CPC ..................................................... C07F 9/6571
See application file for complete search history.

(56) References Cited

U.S. PATENT DOCUMENTS

| 8,552,212 B2 | 10/2013 | Qu et al. |
| 8,946,418 B1 | 2/2015 | Haddad et al. |
| 9,096,626 B2 | 8/2015 | Haddad et al. |

FOREIGN PATENT DOCUMENTS

| CN | 103087105 A | 5/2013 |
| WO | 2011056737 A1 | 5/2011 |
| WO | 2011126917 A1 | 10/2011 |
| WO | 2016094489 A1 | 6/2016 |

OTHER PUBLICATIONS

International Report on Patentability for PCT/EP2017/064797 dated Jun. 21, 2019.
Qu, A mild Dihydrobenzooxaphosphole Oxaline/Iridium Catalytic System for Asymmetric Hydrogenation of Unfunctionalized Dialins:, vol. 53, 2014, p. 14428-14432.
Tang, "Novel, Tunable, and Efficient Chiral Bisdihydrobenzooxaphosphole Ligands for Asymmetric Hydrogenation", Organic Letters, vol. 12, 2009, p. 176-179.
Zhao, "An Efficient Method for Sterically Demanding Suzuki-Miyaura Coupling Reactions," A European Journal, 2012.
Tang, "A general and Special Catalyst for Suzuki-Miyaura Coupling Processes", Angewandte-Chemie, 2010, p. 5879-5883.
English Abstract for CN103087105 cited herein, dated May 8, 2013.
International Search Report and Written Opinion for PCT/US2017/064797 dated Jun. 20, 2018.
Rodriguez, Amine-Tunable Ruthenium Catalysts for Asymmetric Reuction of Ketones, Advanced Synthesis and Catalysis, vol. 356, 2014, p. 301-307.
Kang, Enantioseelective Palladium-Catalyzed Dearomative Cyclization for the Efficient Synthesis of Terpenes and Steroids, Angewandte Chemie International Edition, vol. 54, 2015, p. 3033-3037.

*Primary Examiner* — Karen Cheng
(74) *Attorney, Agent, or Firm* — David L. Kershner

(57) ABSTRACT

This invention relates to novel phosphorous ligands useful for organic transformations. Methods of making and using the ligands in organic synthesis are described. The invention also relates to processes for preparing the novel ligands.

9 Claims, No Drawings

CHIRAL DIHYDROBENZOOXAPHOSPHOLE LIGANDS AND SYNTHESIS THEREOF

FIELD OF THE INVENTION

This invention describes novel phosphorous ligands useful in asymmetric transformations in organic synthesis and novel processes for their preparation.

BACKGROUND

The increasing demand to produce enantiomerically pure pharmaceuticals, agrochemicals, flavors, and other fine chemicals has advanced the field of asymmetric catalytic technologies. Development of efficient asymmetric metal-catalyzed transformations has played a central role for the advancement of asymmetric catalysis. In the past decades, metal-catalyzed reactions with chiral phosphine ligands have been widely utilized and advanced for variety of asymmetric transformations. Development of efficient chiral phosphorus ligands is essential for the success of asymmetric hydrogenation. Known chiral phosphorus ligands in this field include Knowles' DIPAMP [Knowles, W. S. *Acc. Chem. Res.* 1983, 16, 106], Kagan's DIOP [Kagan et al, *J. Am. Chem. Soc.* 1972, 94, 6429], Noyori's BINAP [Noyori, R. *Chem. Soc. Rev.* 1989, 18, 187], Burk's Duphos and BPE [Burk, M. J. et al, Organometallics 1990, 9, 2653; Burk, M. J. et al, *Angew. Chem., Int. Ed. Engl.* 1990, 29, 1462], Imamoto's BisP* [Imamoto, T. et al, J. Am. Chem. Soc. 1997, 119, 1799], Zhang's PennPhos [Zhang, X. et al, *Angew. Chem. Int. Ed. Engl.* 1999, 38, 516] and TangPhos [US2004/0229846 and Zhang, X. et al, *Angew. Chem. Int. Ed.* 2002, 41, 1613.], Pfizer's trichickenfootphos [WO2005/087370 and Hoge, G. et al, *J. Am. Chem. Soc.* 2004, 126, 5966].

More recently, families of phosphine ligands containing a unique dihydrobenzooxaphosphole (BOP) core which are structurally rigid, electronically and sterically tunable, and air-stable have been discovered. For example, one family of ligands (U.S. Pat. No. 9,096,626) is represented by formulas (A) and (B).

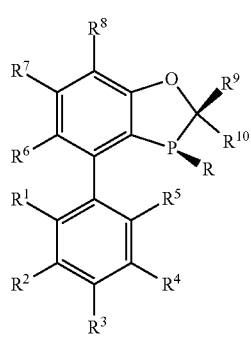

A

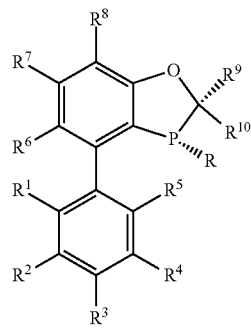

B

Another family of BOP ligands (U.S. Pat. No. 8,552,212) is represented by formulas C and D.

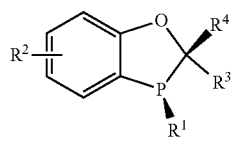

C

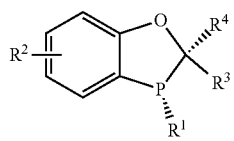

D

Another family of ligands (U.S. Pat. No. 8,946,418) is represented by formulas E and F.

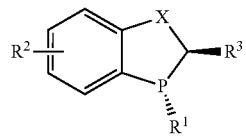

E

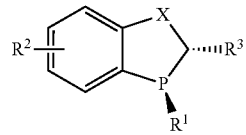

F

These unique chiral BOP ligands have demonstrated superior reactivity and selectivity for various transformations including Suzuki-Miyaura cross-coupling reaction, hydrogenation of enamides, ketones, and unfunctionalized alkenes, propargylation, ketone and imine addition, de-aromative cyclization and reductive alkynone cyclization, hydroboration and ring-opening reactions.

Although tremendous progress has been made in the field of catalysis and many efficient ligands have been developed, the design of new efficient ligands continues to be important since there is no universal ligand for catalytic transformations of various kinds of substrates.

BRIEF SUMMARY OF THE INVENTION

This invention relates to novel phosphorous ligands of general formulas I, II, III, IV, V and VI. Methods of making and using the ligands in organic synthesis are described. The invention also relates to processes for preparing the novel ligands.

DETAILED DESCRIPTION OF THE INVENTION

One embodiment of the present invention is directed to a novel class of phosphorous ligands represented by formula I

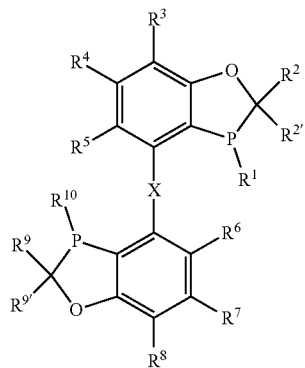

I wherein
X is a bond, —NR$^{11}$, O, CR$^{11}$(R)$^{12}$ or S.
R$^1$ and R$^{10}$ are each independently selected from alkyl, cycloalkyl or optionally substituted aryl;
R$^2$, R$^{2'}$, R$^9$ and R$^{9'}$ are each independently selected from the group consisting of hydrogen, halo, perhaloalkyl, —NR$^{11}$R$^{12}$, —OR$^{11}$, —SR$^{11}$, —Si(R$^{11}$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$ alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent R$^2$ and R$^{2'}$ and R$^9$ and R$^{9'}$ taken together with the carbon atoms to which they are bound to form a substituted or unsubstituted cycloalkyl or heterocyclyl ring;
R$^3$, R$^4$, R$^5$, R$^6$, R$^7$ and R$^8$ are each independently selected from the group consisting of hydrogen, halo, perhaloalkyl, —NR$^{11}$R$^{12}$, —OR$^{11}$, —SR$^{11}$, —Si(R$^{11}$)$_3$, —CN, —NO$_2$, —OH, alkyl, alkenyl, alkynyl, cycloalkyl, heterocycloalkyl, benzyl, aryl, alkyl, heteroarylalkyl, bicycloaryl, heterobicycloaryl, —C(O)alkyl, —C(S)alkyl, —S(O)$_{1-2}$ alkyl, benzyl, aryl, heteroaryl, aryloxy and heteroaryloxy, wherein each alkyl, alkenyl, alkynyl, cycloalkyl, heterocycloalkyl, aryl and heteroaryl are unsubstituted or substituted;
R$^{11}$ and R$^{12}$ are each independently selected from the group consisting of hydrogen, perhaloalkyl, alkyl, alkenyl, alkynyl, cycloalkyl, heterocycloalkyl, benzyl, aryl, and alkyl.
and the enantiomers and diastereomers thereof.

Another embodiment is directed to compounds of formula I as described in the embodiment above, wherein
X is a bond, O, NR$^{11}$ or S;
R$^1$ and R$^{10}$ are each independently selected from C$_{1-6}$alkyl, C$_{3-6}$cycloalkyl or optionally substituted aryl;
R$^2$, R$^{2'}$, R$^9$ and R$^{9'}$ are each independently selected from H, C$_{1-6}$alkyl, or optionally substituted aryl or heteroaryl;
R$^3$, R$^4$, R$^5$, R$^6$, R$^7$ and R$^8$ are each independently selected from H or optionally substituted aryl or heteroaryl;
and the enantiomers and diastereomers thereof.

Another embodiment is directed to compounds of formula I, as described in any of the embodiments above, wherein
X is a bond;
R$^1$ and R$^{10}$ are each independently selected from C$_{1-6}$alkyl, C$_{3-6}$cycloalkyl, or phenyl;
R$^2$, R$^{2'}$, R$^9$ and R$^{9'}$ are each independently selected from H, methyl or isopropyl, phenyl or pyridyl, optionally substituted with methoxy;
R$^3$, R$^4$, R$^5$, R$^6$, R$^7$ and R$^8$ are each independently selected from H or phenyl optionally substituted with one or two groups independently selected from methoxy and trifluoromethyl;
and the enantiomers and diastereomers thereof.

In another embodiment there are compounds of formula I as described as described in any of the embodiments above, wherein
X is a bond;
R$^1$ and R$^{10}$ are each independently selected from is t-butyl, cyclopentyl or cyclohexyl;
R$^2$, R$^{2'}$, R$^9$ and R$^{9'}$ are each independently selected from H, methyl, isopropyl, phenyl or 2-methoxypyridin-2-yl;
R$^3$, R$^4$, R$^5$, R$^6$, R$^7$ and R$^8$ are each independently selected from H, phenyl, 2,6-dimethoxyphenyl, 4-methoxyphenyl, or 3,5-bis(trifluoromethyl)phenyl;
and the enantiomers and diastereomers thereof.

In another embodiment there are compounds of formula I as described in any of the embodiments above, wherein
X is a bond;
R$^1$ and R$^{10}$ are t-butyl;
R$^2$, R$^{2'}$, R$^9$ and R$^{9'}$ are selected from H, methyl and isopropyl; and
R$^3$, R$^4$, R$^5$, R$^6$, R$^7$ and R$^8$ are independently selected from phenyl, 3,5-bis(trifluoromethyl)phenyl, 2,6-dimethoxyphenyl or 4-methoxyphenyl;
and the enantiomers and diastereomers thereof.

In another embodiment there is a compound of formula I selected from

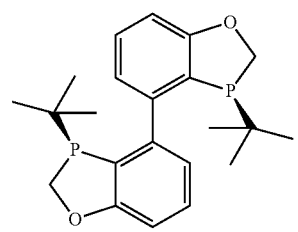

Ia

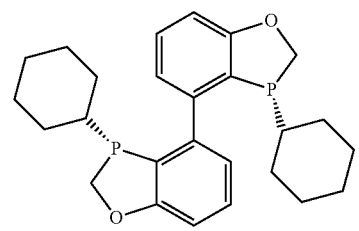

Ib

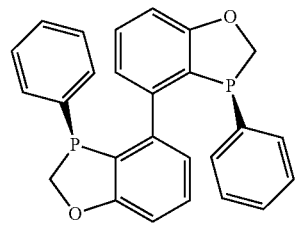

Ic

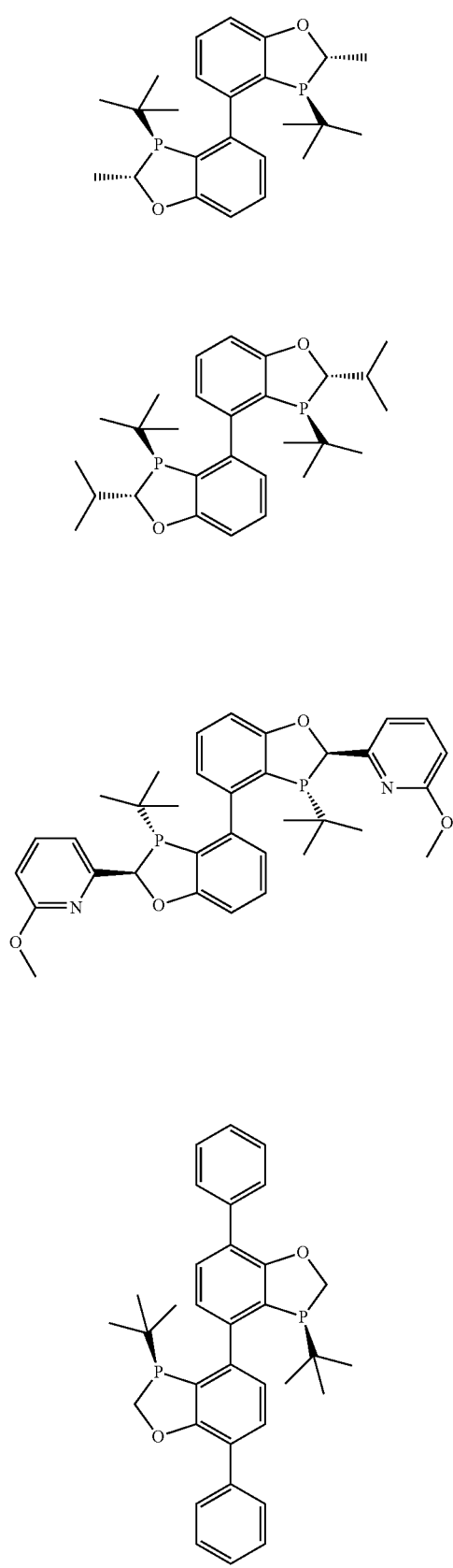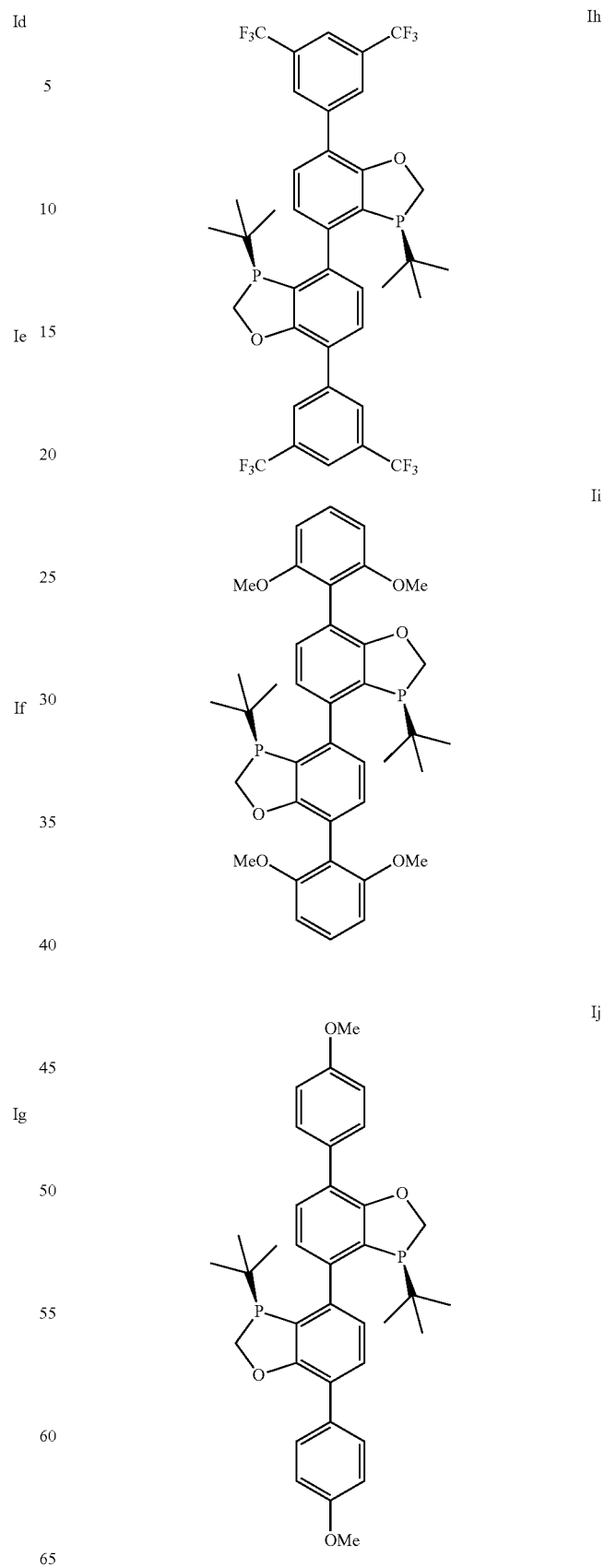
and the enantiomers and diastereomers thereof.

Another embodiment is directed to ligands of formula II

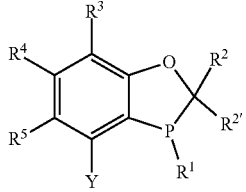

II wherein,

Y=PR$^6$R$^7$, CR$^8$R$^9$, NR$^8$R$^9$, SR$^8$;

R$^1$, R$^6$ and R$^7$ are each independently selected from alkyl, cycloalkyl or optionally substituted aryl;

R$^2$ and R$^{2'}$ are each independently selected from the group consisting of hydrogen, halo, perhaloalkyl, —NR$^8$R$^9$, —OR$^8$, —SR$^8$, —Si(R$^8$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent R$^2$ and R$^{2'}$ taken together with the carbon atoms to which they are bound to form a substituted or unsubstituted cycloalkyl or heterocyclyl ring;

R$^3$, R$^4$, and R$^5$ are each independently selected from the group consisting of hydrogen, halo, perhaloalkyl, —NR$^8$R$^9$, —OR$^8$, —SR$^8$, —Si(R$^8$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$ alkyl, benzyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, R$^8$ and R$^9$ are each independently selected from the group consisting of hydrogen, perhaloalkyl, alkyl, alkenyl, alkynyl, cycloalkyl, heterocycloalkyl, benzyl, aryl, and alkyl.

and the enantiomers and diastereomers thereof.

Another embodiment is directed to ligands of formula II as described above, wherein Y is PR$^6$R$^7$, CR$^8$R$^9$, NR$^8$R$^9$, or SR$^8$ R$^1$ is C$_{1-6}$ alkyl;

R$^2$ and R$^{2'}$ are H;

R$^3$, R$^4$, and R$^5$ are H;

R$^6$ and R$^7$ are C$_{1-6}$ alkyl or aryl;

and the enantiomers and diastereomers thereof.

Another embodiment is directed to ligands of formula II as described in any of the embodiments above, wherein Y is PR$^6$R$^7$ R$^1$ is t-butyl;

R$^2$ and R$^{2'}$ are H;

R$^3$, R$^4$, and R$^5$ are H;

R$^6$ and R$^7$ are t-butyl or phenyl;

and the enantiomers and diastereomers thereof.

Another embodiment is directed to a ligand of formula IIa

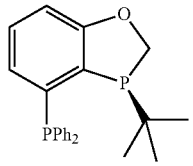

IIa

Another embodiment is directed to ligands of formula III

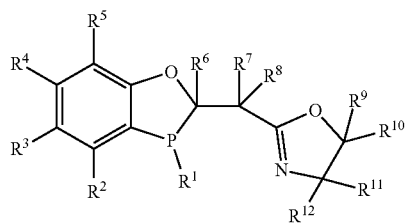

III wherein

R$^1$ is selected from alkyl, cycloalkyl or optionally substituted aryl;

R$^2$, R$^3$, R$^4$, R$^5$, and R$^6$ are each independently selected from the group consisting of hydrogen, halo, perhaloalkyl, —NR$^{13}$R$^{14}$, —OR$^{13}$, —SR$^{13}$, —Si(R$^{13}$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$ alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted;

R$^7$, R$^8$, R$^9$, R$^{10}$, R$^{11}$ and R$^{12}$ are each independently selected from the group consisting of hydrogen, halo, perhaloalkyl, —NR$^{13}$R$^{14}$, —OR$^{13}$, —SR$^{13}$, —Si(R$^{13}$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$ alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent R$^7$, R$^8$, R$^9$, R$^{10}$, R$^{11}$ and R$^{12}$ taken together with the carbon atoms to which they are bound to form a substituted or unsubstituted cycloalkyl, aryl or heteroaryl ring;

R$^{13}$ and R$^{14}$ are each independently selected from the group consisting of hydrogen, perhaloalkyl, alkyl, alkenyl, alkynyl, cycloalkyl, heterocycloalkyl, benzyl, aryl, and alkyl.

and the enantiomers and diastereomers thereof.

Another embodiment is directed to ligands of formula III as described in any of the embodiments above, wherein R$^1$ is C$_{1-6}$ alkyl, C$_{3-6}$ cycloalkyl or optionally substituted aryl;

R$^2$, R$^3$, R$^4$, and R$^5$ are each independently selected from H or optionally substituted aryl or heteroaryl;

R$^6$ is H;

R$^7$ and R$^8$ are C$_{1-6}$alkyl;

R$^9$, R$^{10}$, R$^{11}$ and R$^{12}$ are independently selected from H and C$_{1-6}$alkyl;

and the enantiomers and diastereomers thereof.

Another embodiment is directed to ligands of formula III as described in any of the embodiments above, wherein $R^1$ is $C_{1-6}$alkyl;

$R^2$, $R^3$, $R^4$, and $R^5$ are H;

$R^6$ is H;

$R^7$ and $R^8$ are $C_{1-6}$alkyl;

$R^9$, $R^{10}$, $R^{11}$ and $R^{12}$ are independently selected from H and $C_{1-6}$ alkyl and the enantiomers and diastereomers thereof.

Another embodiment is directed to ligands of formula III as described in any of the embodiments above, wherein $R^1$ is t-butyl;

$R^2$, $R^3$, $R^4$, and $R^5$ are H;

$R^6$ is H;

$R^7$ and $R^8$ are methyl;

$R^9$, $R^{10}$, $R^{11}$ and $R^{12}$ are independently selected from H and $C_{1-6}$alkyl and the enantiomers and diastereomers thereof.

Another embodiment is directed to a ligand of formula III selected from the group

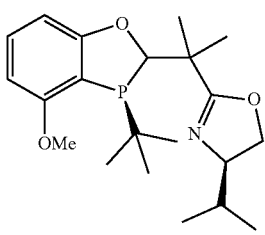

IIIa

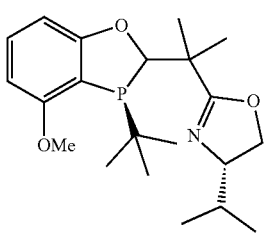

IIIb

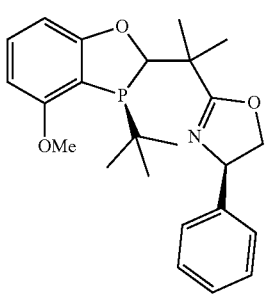

IIIc

Another embodiment is directed to ligands of formula IV

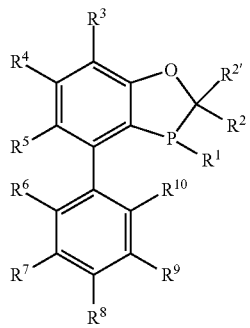

IV wherein $R^1$ is selected from alkyl, cycloalkyl or optionally substituted aryl;

$R^2$ and $R^{2'}$ are each independently selected from the group consisting of hydrogen, halo, perhaloalkyl, —$NR^{11}R^{12}$, —$OR^{11}$, —$SR^{11}$, —$Si(R^{11})_3$, —CN, —$NO_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —$S(O)_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent $R^2$ and $R^{2'}$ taken together with the carbon atoms to which they are bound to form a substituted or unsubstituted cycloalkyl or heterocyclyl ring;

$R^3$, $R^4$, $R^5$, $R^6$, $R^7$, $R^8$, $R^9$, and $R^{10}$ are each independently selected from the group consisting of hydrogen, halo, perhaloalkyl, —$NR^{11}R^{12}$, —$OR^{11}$, —$SR^{11}$, —$Si(R^{11})_3$, —CN, —$NO_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —$S(O)_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted;

$R^{11}$ and $R^{12}$ are each independently selected from the group consisting of hydrogen, perhaloalkyl, alkyl, alkenyl, alkynyl, cycloalkyl, heterocycloalkyl, benzyl, aryl, and alkyl.

and the enantiomers and diastereomers thereof.

Another embodiment, is directed to compounds of formula IV as described above in any of the embodiments wherein $R^1$ is $C_{1-6}$ alkyl, $C_{3-6}$cycloalkyl or optionally substituted aryl;

$R^2$ and $R^{2'}$ are each independently selected from H or $C_{1-4}$alkyl;

$R^3$, $R^4$ and $R^5$ are each independently selected from —OMe or H;

$R^6$ and $R^{10}$ are —OMe;

$R^7$ and $R^9$ are $C_{1-6}$ alkyl, $C_{3-6}$ cycloalkyl or optionally substituted aryl;

$R^8$ is H;

and the enantiomers and diastereomers thereof.

Another embodiment is directed to ligands of formula IV as described in any of the embodiments above, wherein $R^1$ is $C_{1-6}$ alkyl;

$R^2$ and $R^{2'}$ are each independently selected from H or $C_{1-3}$ alkyl $R^3$, $R^4$ and $R^5$ are each independently selected from —OMe or H;

$R^6$ and $R^{10}$ are —OMe;

$R^7$ and $R^9$ are $C_{1-6}$alkyl, $C_{3-6}$ cycloalkyl or optionally substituted aryl;

$R^8$ is H;

and the enantiomers and diastereomers thereof.

Another embodiment is directed to ligands of formula IV as described in any of the embodiments above, wherein $R^1$ is t-butyl;

$R^2$ and $R^{2'}$ are each independently selected from H or $C_{1-3}$alkyl $R^3$, $R^4$ and $R^5$ are each independently selected from —OMe or H;

$R^6$ and $R^{10}$ are —OMe;

$R^7$ and $R^9$ are $C_{1-3}$alkyl, cyclopropyl or optionally substituted phenyl;

$R^8$ is H;

and the enantiomers and diastereomers thereof.

Another embodiment is directed to ligands of formula IV as described in any of the embodiments above, wherein $R^1$ is t-butyl;

$R^2$ and $R^{2'}$ are each independently selected from H, methyl or —CH(CH$_3$)$_2$;

$R^3$, $R^4$ and $R^5$ are H;

$R^6$ and $R^{10}$ are —OMe;

$R^7$ and $R^9$ are $C_{1-3}$alkyl, cyclopropyl or phenyl, optionally substituted with one to two groups selected from methoxy and —CF$_3$;

$R^8$ is H;

and the enantiomers and diastereomers thereof.

Another embodiment is directed to a ligand of formula IV selected from the group IVa
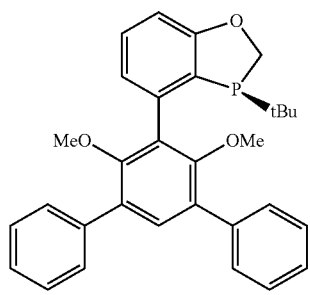

IVb
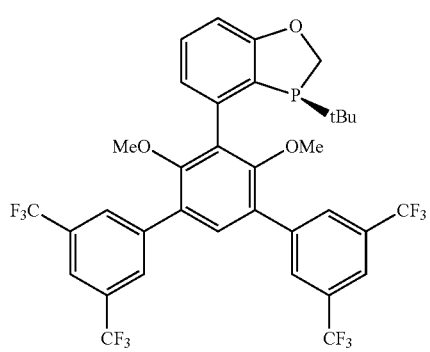

IVc
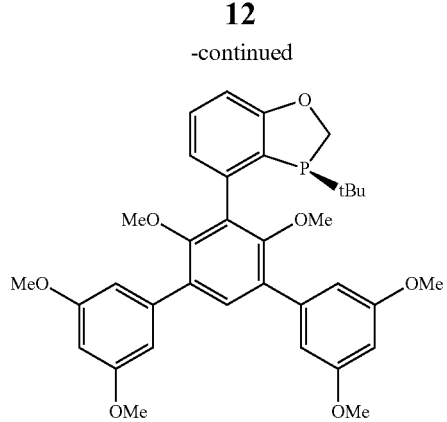

IVd
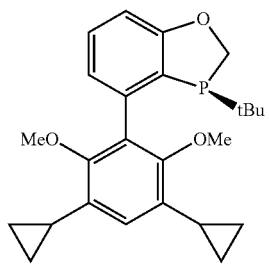

IVe
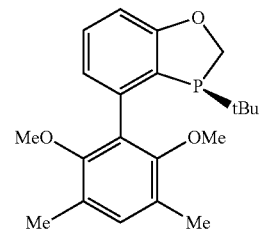

IVf
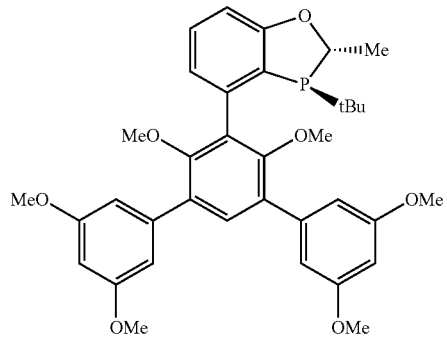

IVg
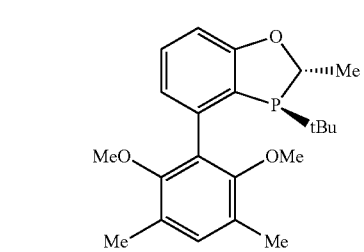

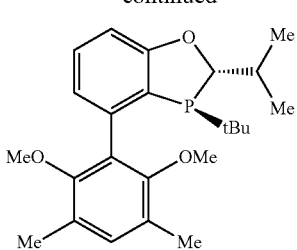

and the enantiomers and diastereomers thereof.

Another embodiment of the present invention is directed to a palladacycle represented by formula V

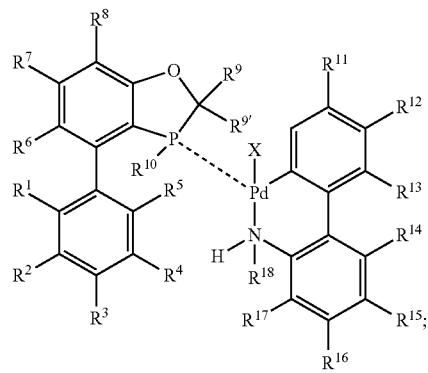

wherein,

X is an halogen, triflate, tosylate or mesylate;

$R^1, R^2, R^3, R^4, R^5, R^6, R^7, R^8, R^{11}, R^{12}, R^{13}, R^{14}, R^{15}, R^{16}$, and $R^{17}$ are each independently selected from the group consisting of hydrogen, halo, perhaloalkyl, —$NR^{19}R^{20}$, —$OR^{19}$, —$SR^{19}$, —$Si(R^{19})_3$, —CN, —$NO_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —$S(O)_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, $R^9$ and $R^{9'}$ are each independently selected from the group consisting of hydrogen, halo, perhaloalkyl, —$NR^{19}R^{20}$, —$OR^{19}$, —$SR^{19}$, —$Si(R^{19})_3$, —CN, —$NO_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —$S(O)_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent $R^9$ and $R^{9'}$ taken together with the carbon atoms to which they are bound to form a substituted or unsubstituted cycloalkyl or heterocyclyl ring;

$R^{10}$ is selected from alkyl, cycloalkyl or optionally substituted aryl;

$R^{18}$ is selected from alkyl, cycloalkyl or optionally substituted aryl;

$R^{19}$ and $R^{20}$ are each independently selected from the group consisting of hydrogen, perhaloalkyl, alkyl, alkenyl, alkynyl, cycloalkyl, heterocycloalkyl, benzyl, aryl, and alkyl;

and the enantiomers and diastereomers thereof.

Another embodiment is directed to a palladacycle of formula V as described in the embodiment above, wherein
$R^1$ and $R^5$ are alkoxy or alkyl;
$R^2, R^3, R^4, R^6, R^7, R^8, R^9$, and $R^{9'}$ are H;
$R^{10}$ is alkyl, cycloalkyl, or aryl;
$R^{11}, R_{12}, R^{13}, R^{14}, R^{15}, R^{16}$, and $R^{17}$ are H;
$R^{18}$ is H or alkyl;
X is mesylate;
and the enantiomers and diastereomers thereof.

Another embodiment is directed to a palladacycle of formula V as described in any of the embodiments above, wherein,
$R^1$ and $R^5$ are —OMe;
$R^2, R^3, R^4, R^6, R^7, R^8, R^9$, and $R^{9'}$ are H;
$R^{10}$ is tert-butyl;
$R^{11}, R^{12}, R^{13}, R^{14}, R^{15}, R^{16}$, and $R^{17}$ are H;
$R^{18}$ is H;
X is mesylate;
and the enantiomers and diastereomers thereof.

Another embodiment is directed to a ligand of formula Va

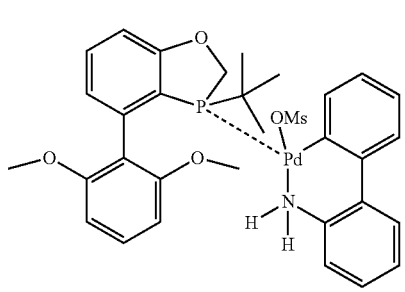

Another embodiment of the present invention is directed to a ligand represented by formula VI

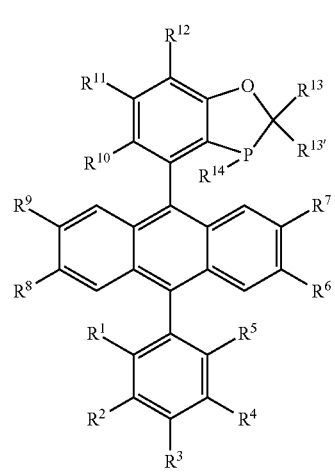

$R^1, R^2, R^3, R^4, R^5, R^6, R^7, R^8, R^9, R^{10}, R^{11}$ and $R^{12}$ are each independently selected from the group consisting of hydrogen, halo, perhaloalkyl, —$NR^{15}R^{16}$, —$OR^{15}$, —$SR^{15}$, —$Si(R^{15})_3$, —CN, —$NO_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —$S(O)_{1-2}$ alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted;

$R^{13}$ and $R^{13'}$ are each independently selected from the group consisting of hydrogen, halo, perhaloalkyl, —$NR^{15}R^{16}$, —$OR^{15}$, —$SR^{15}$, —$Si(R^{15})_3$, —CN, —$NO_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —$S(O)_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent $R^{13}$ and $R^{13'}$ taken together with the carbon atoms to which they are bound to form a substituted or unsubstituted cycloalkyl or heterocyclyl ring;

$R^{14}$ is selected from alkyl, cycloalkyl or optionally substituted aryl;

$R^{15}$ and $R^{16}$ are each independently selected from the group consisting of hydrogen, perhaloalkyl, alkyl, alkenyl, alkynyl, cycloalkyl, heterocycloalkyl, benzyl, aryl, and alkyl.

and the enantiomers and diastereomers thereof.

Another embodiment is directed to the ligand of formula VI as described above, wherein $R^1$, $R^3$ and $R^5$ are H, alkyl or alkoxy;

$R^2$, $R^4$, $R^6$, $R^7$, $R^8$, $R^9$, $R^{10}$ $R^{11}$, and $R^{12}$ are H;

$R^{13}$ and $R^{13'}$ are independently selected from H or alkyl;

$R^{14}$ is alkyl, cycloalkyl or optionally substituted aryl;

and the enantiomers and diastereomers thereof.

Another embodiment is directed to the ligand of formula VI as described in any of the embodiments above, wherein $R^1$, $R^3$ and $R^5$ are methyl;

$R^2$, $R^4$, $R^6$, $R^7$, $R^8$, $R^9$, $R^{10}$ $R^{11}$, and $R^{12}$ are H;

$R^{13}$ and $R^{13'}$ are independently selected from H or alkyl;

$R^{14}$ is tert-butyl;

and the enantiomers and diastereomers thereof.

Another embodiment is directed to a ligand of formula VI selected from

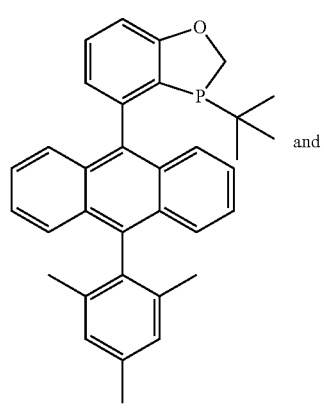

VIa and

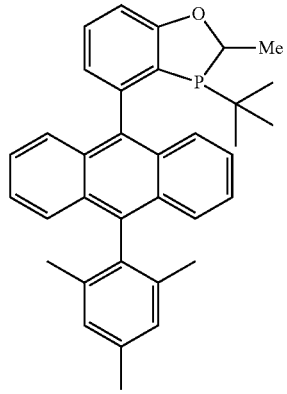

VIb

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist.

Some of the compounds of formula (I) can exist in more than one tautomeric form. The invention includes methods for using all such tautomers.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methyl-ethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —(C (CH₃)₂—CH₂)—, —(CH(CH₃)—CH(CH₃))—, —(CH₂—CH(CH₂CH₃))—, —(CH(CH₂CH₃)—CH₂)—, —(CH(CH₂CH₂CH₃))—, —(CHCH(CH₃)₂)— and —C(CH₃)(CH₂CH₃)—.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1λ⁶-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-azaspiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, non-limiting examples would be —CH₂CHF₂, —CF₃ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)₂—$C_{1-6}$ alkyl, likewise, —S—$R_a$ may be represented as phenyl-S(O)$_m$— when $R^a$ is phenyl and where m is 0, 1 or 2.

General Synthetic Methods

Scheme 1 and Scheme 2 illustrate how compounds of Formula (I) and Formula (II) may be prepared.

Lithiated compounds I-1 react with the phosphine dichloride I-2 followed water give phosphinate compounds I-3. Compounds 1-3 react with carbonyl compounds I-4 produce alcohols I-5. Deprotection of compounds I-5 affords triol compounds I-6. Mesylation of compounds I-6 followed by hydrolysis give compounds I-10. Preparation of diastereomers I-11 and I-12 followed by separation of these diastereoisomers I-11 and I-12 through crystallization or column chromatography give enantiomerically enriched isomer I-11 and I-12. Hydrolysis of I-11 and I-12 give enantiomerically enriched I-13 and I-14.

Scheme 1

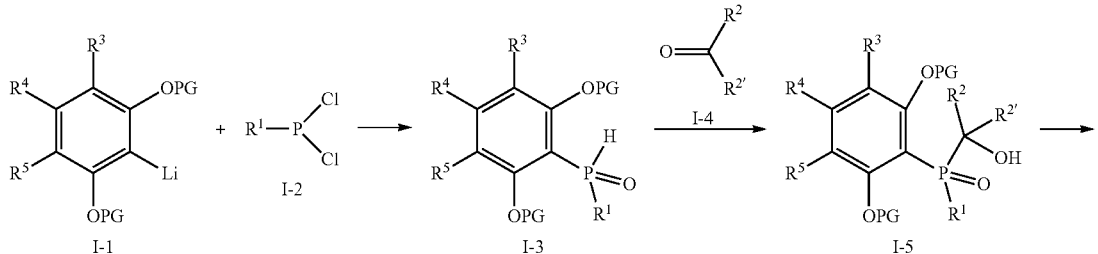

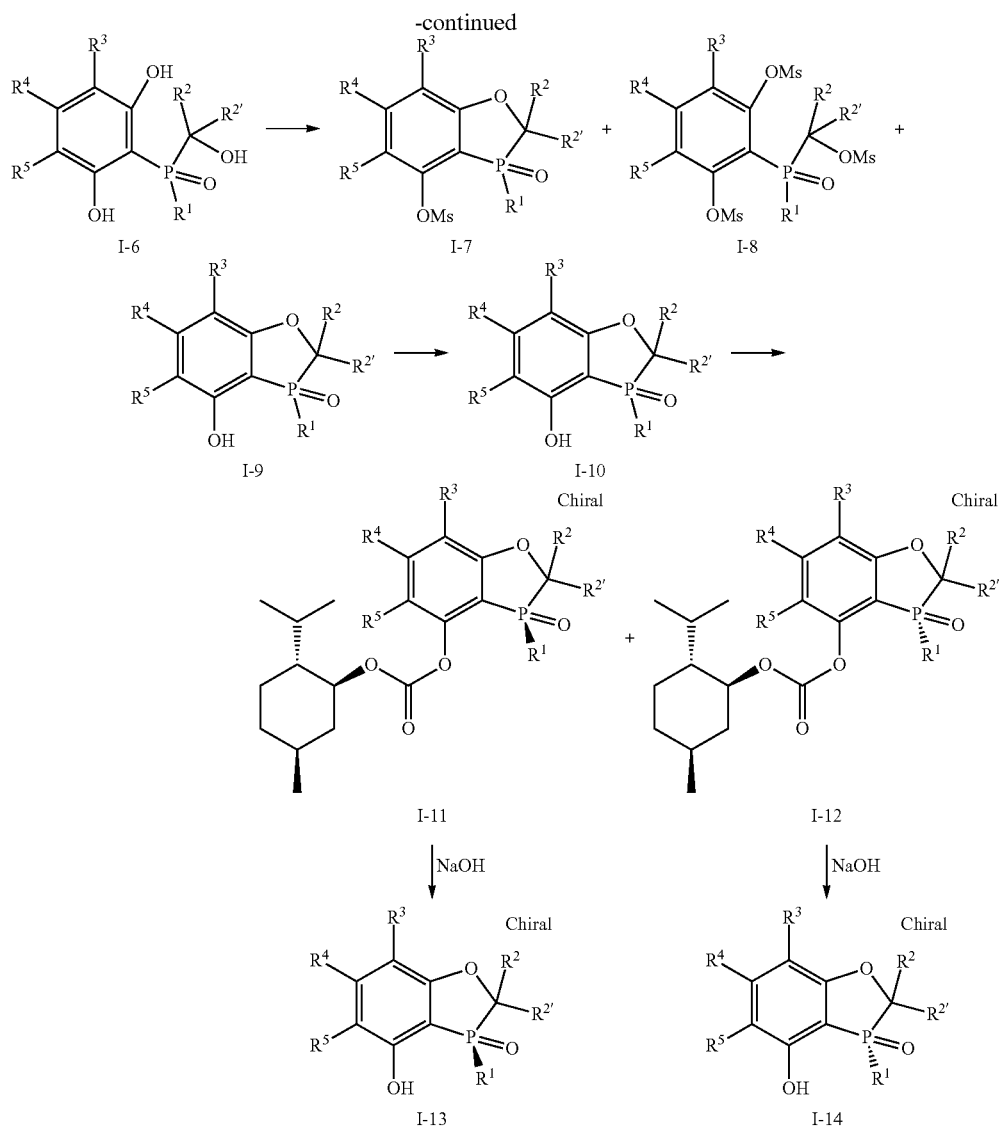

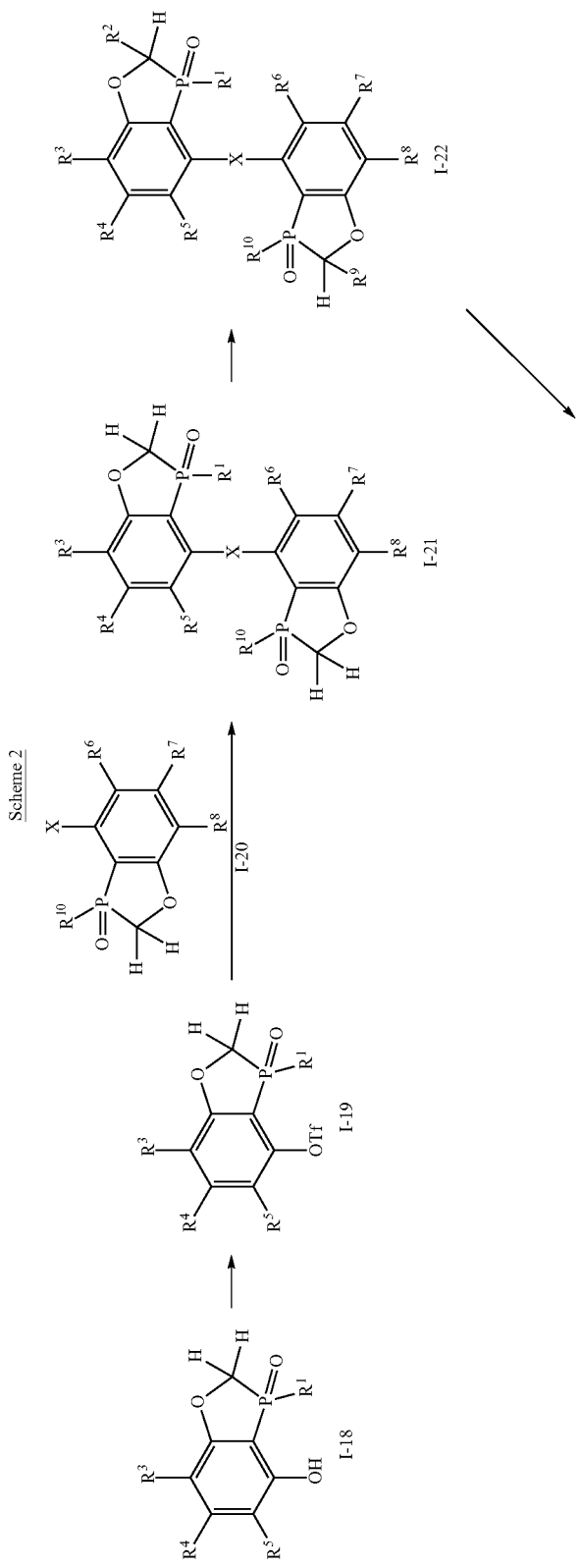

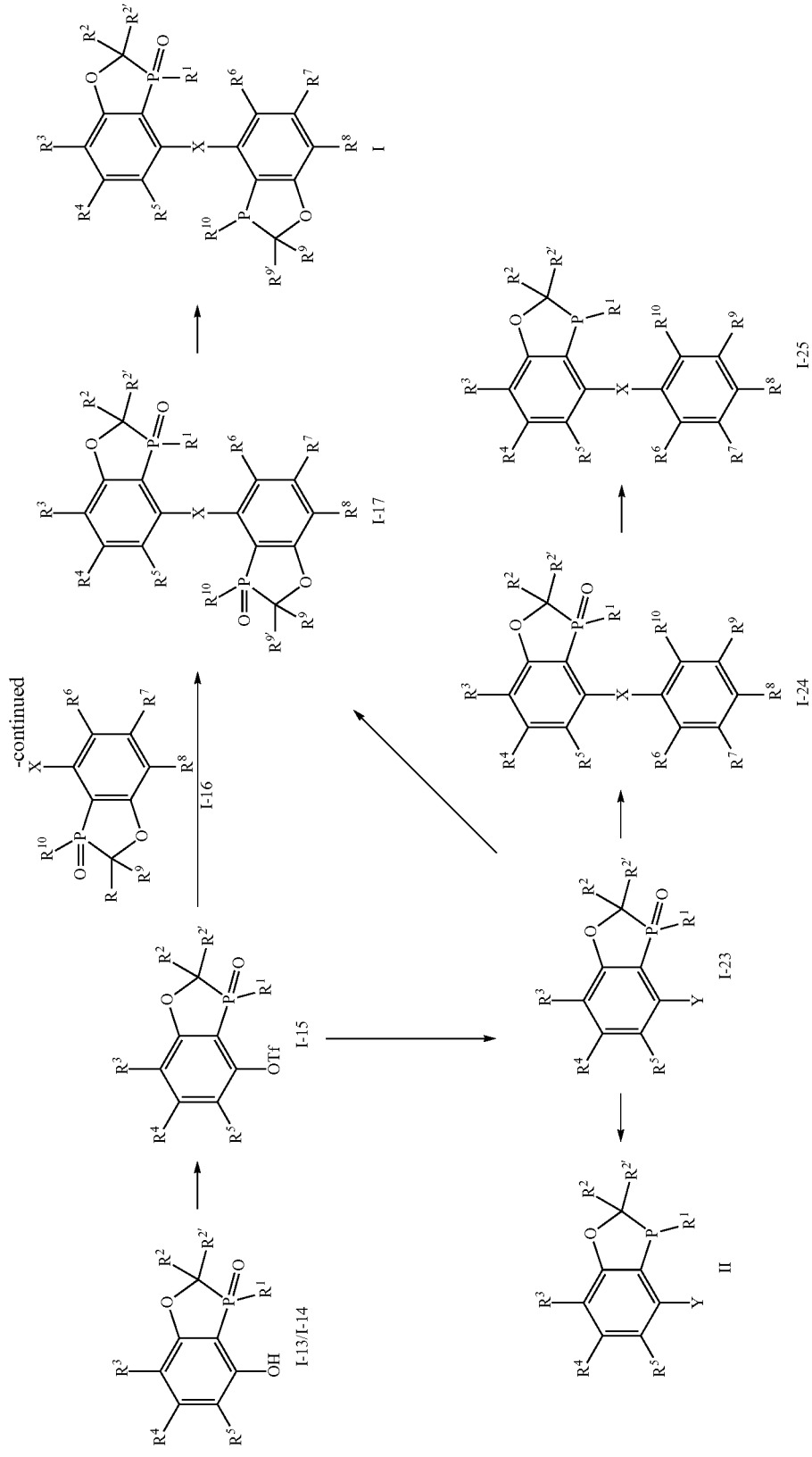

Compounds I-13/I-14 are converted to triflates I-15 which react with I-16 to give phosphine oxide I-17. Reduction of I-17 produces Formula (I).

Triflate I-15 can be converted to compounds I-23. Reduction of I-23 affords Formula (II).

Compounds I-24 are made through cross-coupling reactions. Reduction of phosphine oxide I-24 generates compounds I-25.

Triflate I-19 can be made from compounds I-18. I-19 can react with compound I-20 to produce I-21. Nucleophilic displacement of I-21 can give I-22 which can be converted to compounds I-17.

Scheme 3 illustrates how compounds of Formula (III) can be prepared.

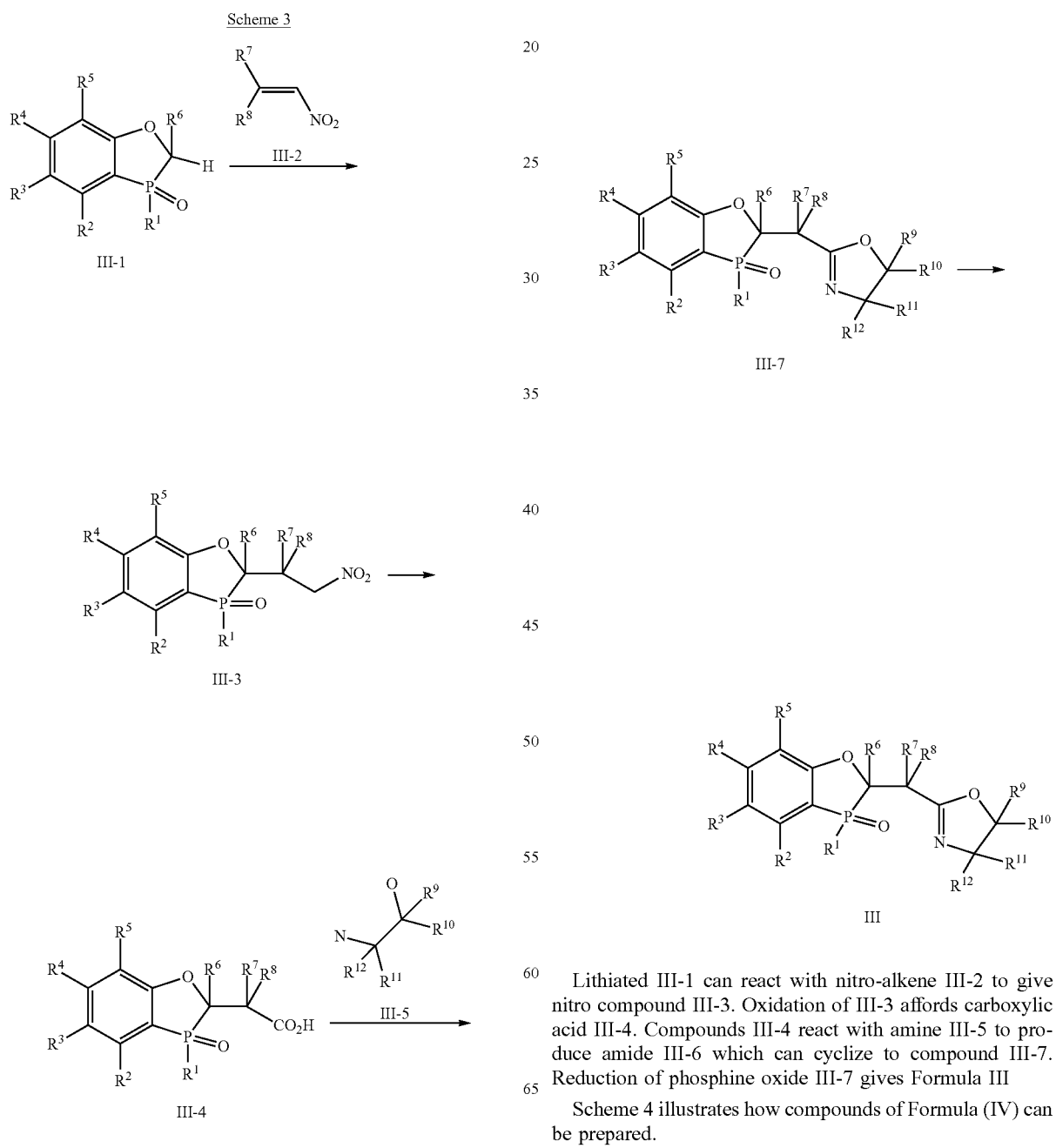

Lithiated III-1 can react with nitro-alkene III-2 to give nitro compound III-3. Oxidation of III-3 affords carboxylic acid III-4. Compounds III-4 react with amine III-5 to produce amide III-6 which can cyclize to compound III-7. Reduction of phosphine oxide III-7 gives Formula III Scheme 4 illustrates how compounds of Formula (IV) can be prepared.

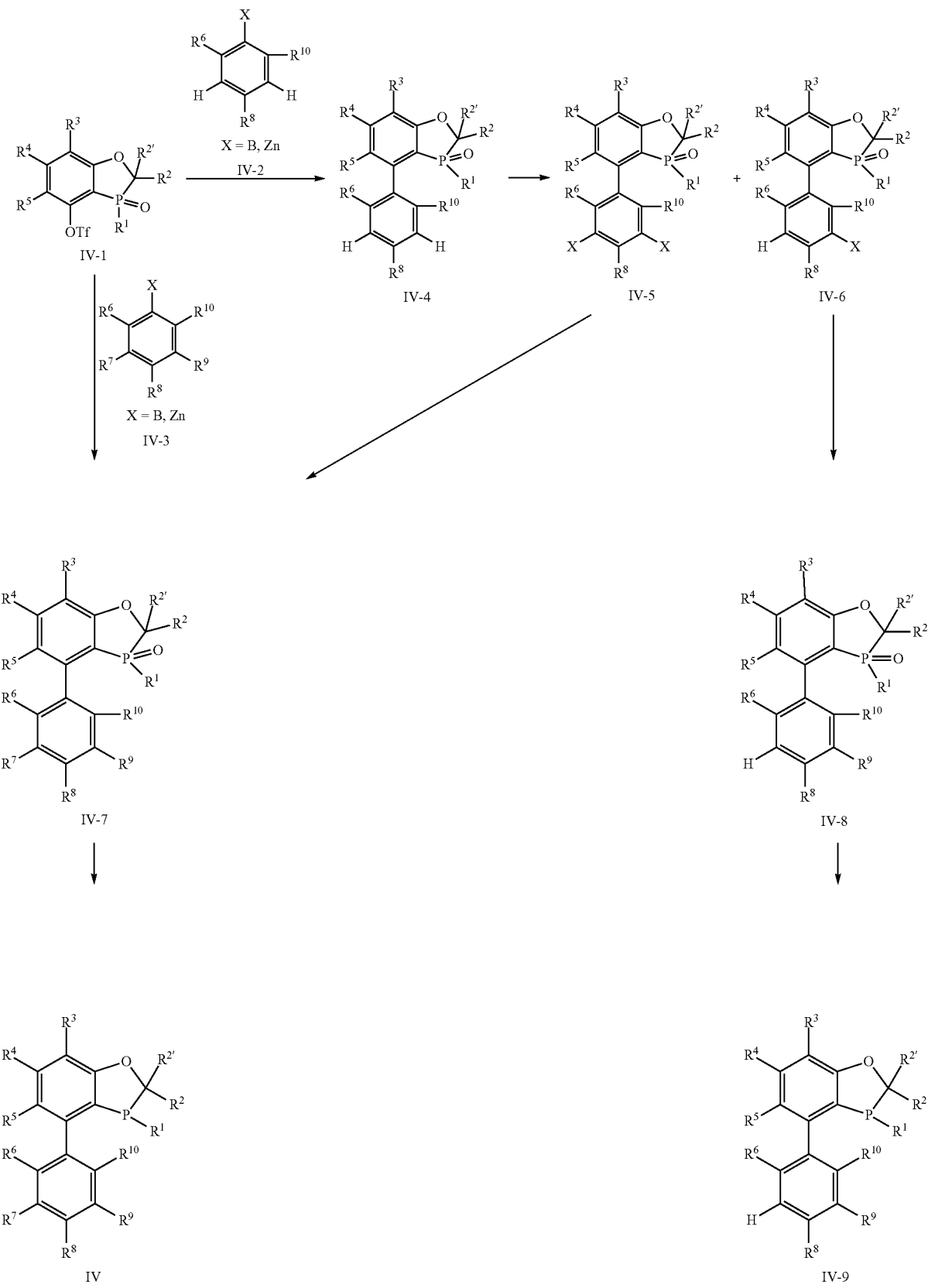

Triflates IV-1 react with organometallic compound IV-2 to form compound IV-4. Haloganation of IV-4 gives halide IV-5 and IV-6. The mono halide IV-6 is converted to IV-8. Reduction of phosphine oxide IV-8 gives IV-9. Compounds IV-5 can be converted to compounds IV-7. Reduction of phosphine oxide IV-7 produces Formula IV. Compounds IV-1 can react with IV-3 to give compound IV-7.

Scheme 5 illustrates how palladacycles of formula (V) may be prepared.

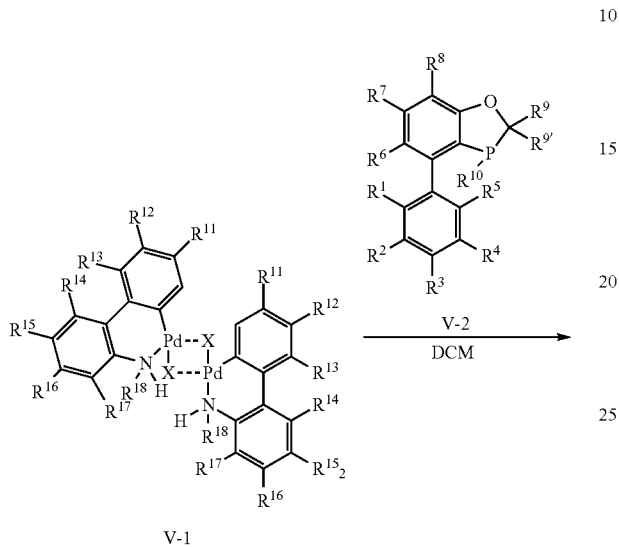

V-1

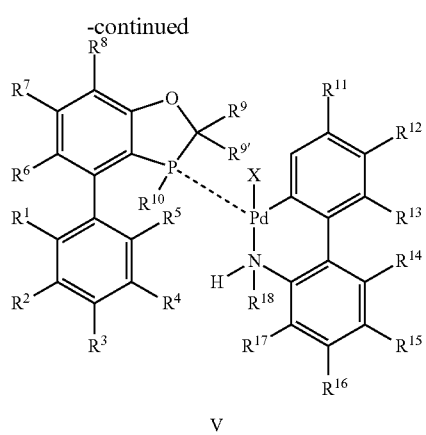

V

As illustrated in Scheme 5, the palladium dimer V-1 is reacted with ligand V-2 in dichloromethane. After crystallization, the desired compound of formula V is obtained.

Scheme 6 illustrates how ligands of formula (VI) may be prepared.

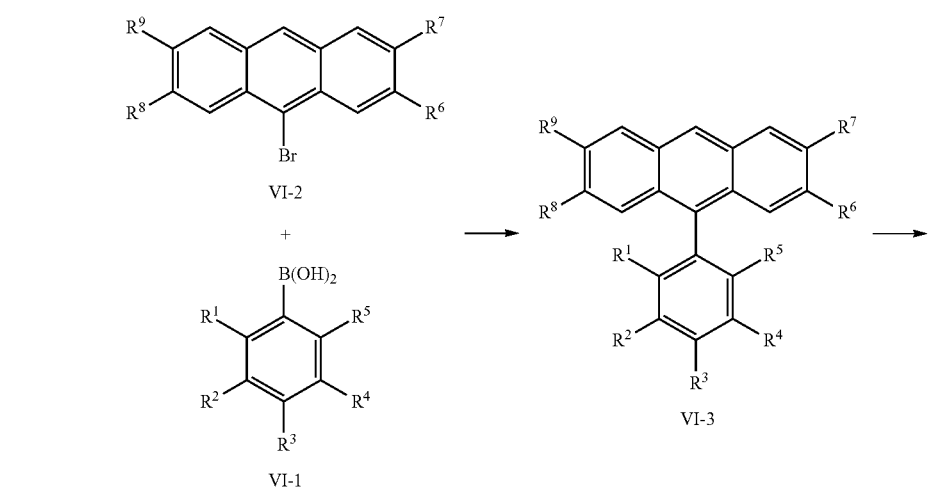

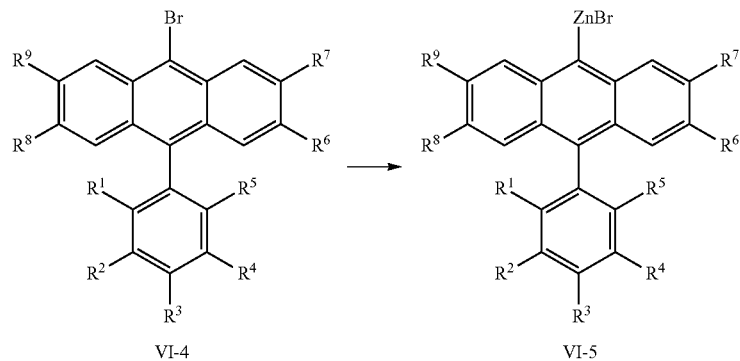

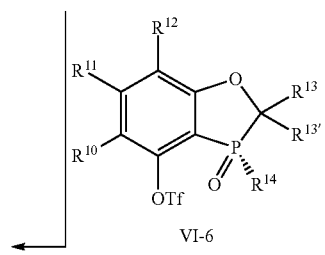

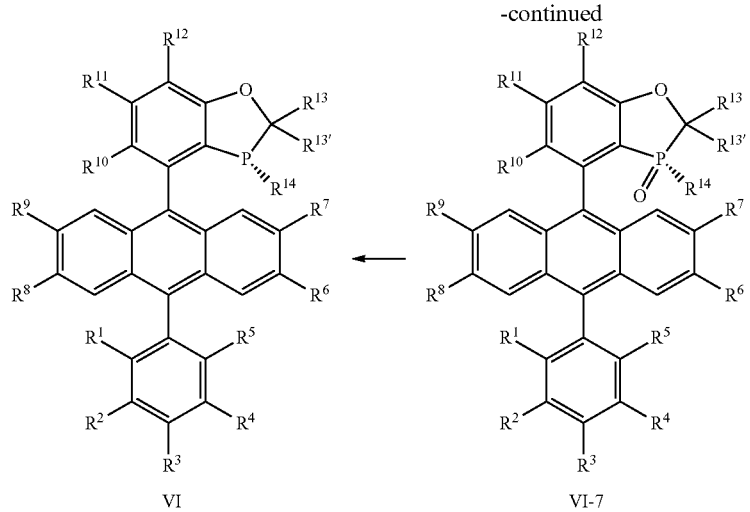

As illustrated in scheme 6, VI-3 is prepared via a palladium-catalyzed Suzuki coupling between VI-1 and VI-2. The resulting anthracene derivative VI-3 is brominated to procure VI-4. VI-4 is then treated with zinc to generate VI-5 which is utilized for a subsequent palladium-catalyzed Negishi coupling with triflate VI-6. The phosphine oxide 6 g obtained is then reduced to provide the desired ligand of formula VI.

SYNTHETIC EXAMPLES

Examples 1-6

Examples 1 to 6 describes how compound 8 and 9 are prepared.

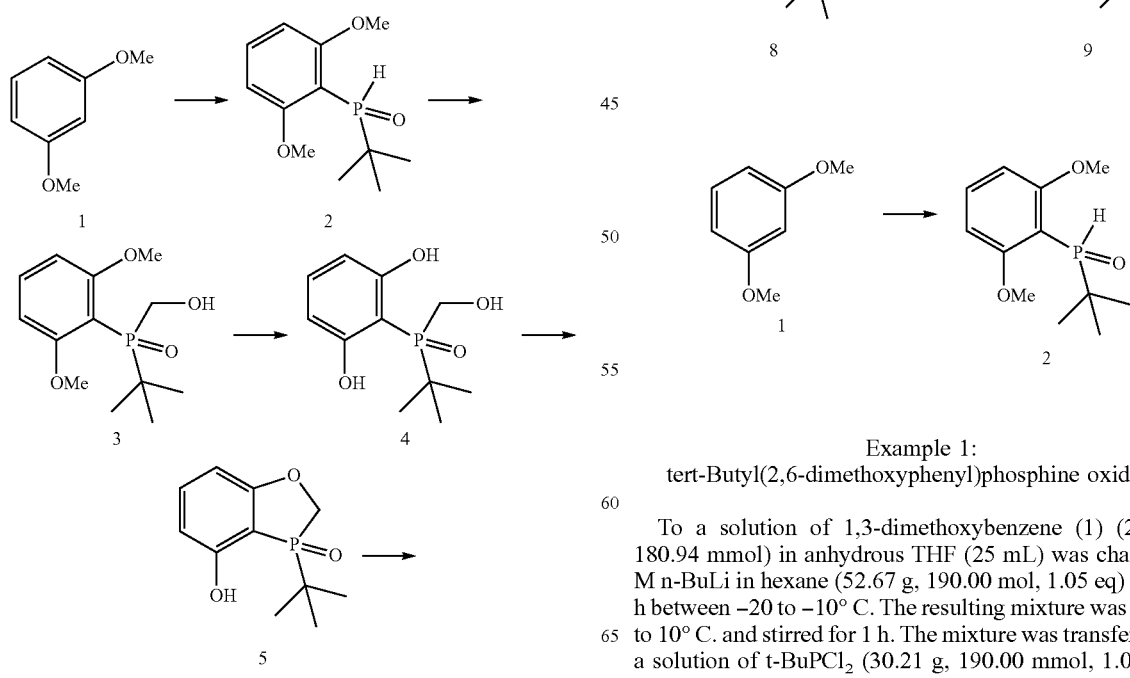

Example 1:
tert-Butyl(2,6-dimethoxyphenyl)phosphine oxide (2)

To a solution of 1,3-dimethoxybenzene (1) (25.00 g, 180.94 mmol) in anhydrous THF (25 mL) was charged 2.5 M n-BuLi in hexane (52.67 g, 190.00 mol, 1.05 eq) over 0.5 h between −20 to −10° C. The resulting mixture was warmed to 10° C. and stirred for 1 h. The mixture was transferred into a solution of t-BuPCl$_2$ (30.21 g, 190.00 mmol, 1.05 eq) in anhydrous THF (30.21 g) cooled at −20° C. while the internal temperature was controlled below 5° C. The mixture was stirred at 0° C. for about 1 h. Water (50 mL) was added below 20° C. The volatiles (~50 mL) were distilled under reduced pressure. Hexane (50 mL) was added and the mixture was stirred for ~20 min. The aqueous phase was separated and the organic phase was extracted with water (25 mL). The combined aqueous extracts (~104 g, containing 41.64 g of product 2, 171.90 mmol, 95% yield) were used in the next step without further purification.

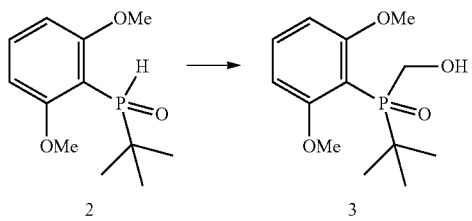 [SMILES: COc1cccc(OC)c1[PH](=O)C(C)(C)C ; COc1cccc(OC)c1P(=O)(CO)C(C)(C)C]

Example 2: tert-Butyl(2,6-dimethoxyphenyl)(hydroxymethyl)phosphine oxide (3)

To the crude product 2 (41.64 g, 171.90 mmol) in water from previous step was added 6 M NaOH (42.97 mL, 257.82 mmol, 1.50 eq). The solution was heated to ~65° C. and 37% formaline solution (69.76 g, 859.50 mmol, 5.00 eq) was added slowly to maintain the internal temperature between 65-75° C. The mixture was stirred for 0.5 h at this temperature and cooled to room temperature. Concentrated hydrochloric acid (22.20 mL, 266.43 mmol, 1.55 eq) was added below 30° C. to adjust pH to 3-4. The mixture was extracted with $CH_2Cl_2$ (3×70 mL) and the combined extracts were concentrated to remove ~170 mL of solvents. The residual mixture was diluted with MeOH (120 mL) and treated with 6 M HCl in 2-propanol (0.57 mL, 0.02 eq) for ~1 h at 55-60° C. Solvents (120 mL) were removed under reduced pressure. 2-Butanone (120 mL) was charged and solvents (120 mL) was removed under reduced pressure. This process was repeated twice. The mixture was cooled to rt. Isopropyl acetate (80 mL) was charged over 0.5 h and the mixture was stirred for at least 0.5 h. The solid was filtered, rinsed with a mixed solution of 2-butanone (40 mL) and isopropyl acetate (80 mL), and dried to give white solid product 3 (32.33 g, 69%). Crystallization of the concentrated filtrate from 2-butanone and isopropyl acetate (1/2, v/v) gave the $2^{nd}$ crop as white solid (9.48 g, 20%) with high purity similar to the first crop. Analytical data for 3: $^1$H NMR (400 MHz, DMSO-$d_6$) δ 7.45 (t, J=8.4 Hz, 1H), 6.69 (dd, J=8.4, 3.6 Hz, 2H), 4.76-4.72 (m, 1H), 4.17 (dd, J=13.8, 8.3 Hz, 1H), 3.97-3.92 (m, 1H), 3.73 (s, 6H), 1.04 (d, J=14.7 Hz, 9H); $^{13}$C NMR (100 MHz, DMSO-$d_6$) δ 162.9, 134.1, 106.2 (d, J=76.9 Hz), 105.0 (d, J=5.6 Hz), 59.0 (d, J=74.2 Hz), 55.9, 34.2 (d, J=66.0 Hz), 24.5; $^{31}$P NMR (162 MHz, DMSO-$d_6$) δ 48.1; HRMS (ESI$^+$) calcd for $C_{13}H_{21}O_4P$+H, 273.1256; found, 273.1266.

Example 3: tert-Butyl(2,6-dihydroxyphenyl)(hydroxymethyl)phosphine oxide (4)

A mixture of 3 (14.60 g, 53.62 mmol) and 57% HI (96.26 g, 428.96 mmol, 8.00 eq) was stirred at ~92° C. for 5 h, at ~95° C. for 5 h, and 97-100° C. for 14 h for complete demethylation. The resulting solution was cooled to 0-5° C. and stirred for 1 h. Dichloromethane (50 mL) was added and 50% NaOH (25.31 g, 316.38 mmol, 5.90 eq) was added slowly to maintain the temperature below 15° C. The slurry was aged at 15-20° C. for 2 h, filtered, rinsed with water (~100 mL) to pH ~7. The solid was dried in a vacuum oven at 40° C. until water content was <0.1% to give white solid product 4 (12.30 g, 94%). Analytical data for 4: $^1$H NMR (400 MHz, DMSO-$d_6$) δ 7.16 (t, J=8.1 Hz, 1H), 6.25 (dd, J=8.1, 3.6 Hz, 2H), 4.31 (s, 2H), 1.14 (d, J=1.47 Hz, 9H); $^{13}$C NMR (100 MHz, DMSO-$d_6$) δ 134.5, 107.0 (br), 96.4 (d, J=81.6 Hz), 58.0 (d, J=73.7 Hz), 34.3 (d, J=63.2 Hz), 24.5; $^{31}$P NMR (162 MHz, DMSO-$d_6$) δ 64.3; HRMS (ESI$^+$) calcd for $C_{11}H_{17}O_4P$ +H, 245.0943; found, 245.0934.

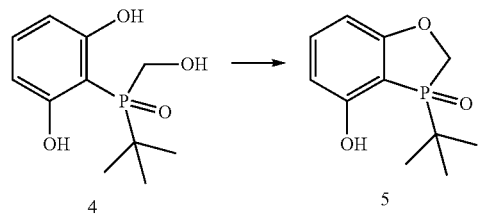 [SMILES: CC(C)(C)P(=O)(CO)c1c(O)cccc1O ; CC(C)(C)P1(=O)COc2cccc(O)c21]

Example 4: 3-(tert-Butyl)-4-hydroxy-2H-benzo[d][1,3]oxaphosphole 3-oxide (5)

To the suspension of triol 4 (100.00 g, 0.41 mol) in THF (200 mL) was added Et$_3$N (124.30 g, 1.23 mol, 3.00 eq) and the resulting solution was cooled to −5° C. Methanesulfonyl chloride (107.88 g, 0.94 mol, 2.30 eq) was added slowly to control the internal temperature below 20° C. After addition, the mixture was warmed up and stirred at 25° C. for 0.5 h. A solution of NaOH (98.27 g, 2.46 mol, 6.00 eq) in water (500 mL) was charged. The mixture was heated to 60° C., stirred for 1 h, then cooled to 25° C. and neutralized with a solution of concentrated HCl (201.71 g, 2.05 mol, 5.00 eq) in water (170 mL) to pH <2. The mixture was distilled at ~50° C. under reduced pressure to remove volatiles (180 mL). MeOH (200 mL) was added and the mixture was distilled at ~50° C. under reduced pressure to remove solvents (220 mL). The suspension was cooled to 10° C., rinsed with water (200 mL) and heptane (100 mL). The wet cake was dried in a vacuum oven at ~40° C. to constant weight to give white solid product 5 (88.40 g, 95%).

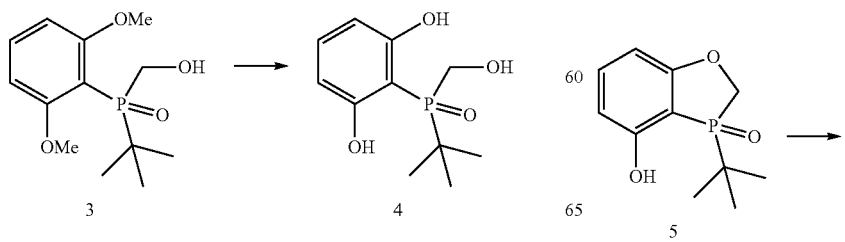

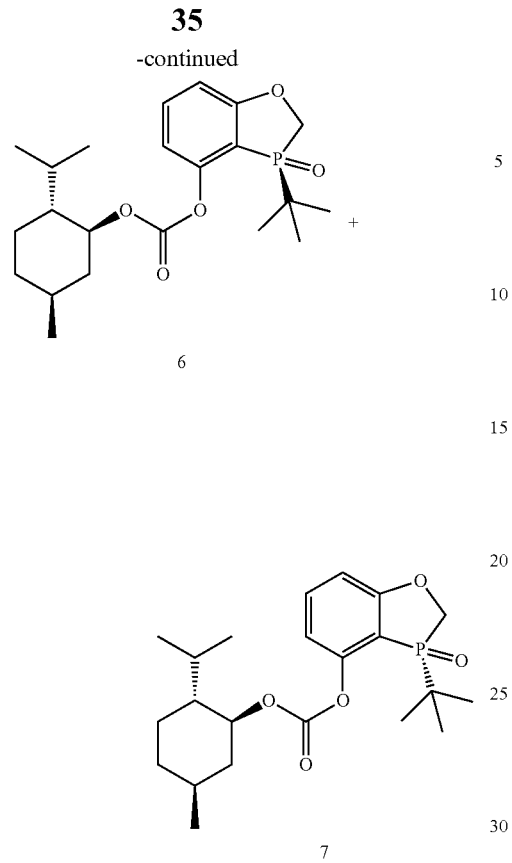

Example 5: (R)-3-(tert-Butyl)-3-oxido-2H-benzo[d][1,3]oxaphosphol-4-yl ((1S,2R,5S)-2-isopropyl-5-methylcyclohexyl) carbonate (6)

To the suspension of 5 (40.00 g, 176.83 mmol) in CH$_3$CN (120 mL) was added i-Pr$_2$NEt (29.71 g, 229.88 mmol, 1.30 eq), followed by (+)-menthyl chloroformate (41.00 g, 187.44 mmol, 1.06 eq). The mixture was heated to 60° C. in ~0.5 h and held for ~1 h. The slurry was cooled to ~5° C. in 1 h and held for 2 h. The solid was filtered, rinsed with chilled MeCN (80 mL), and dried at ~40° C. under vacuum to give white solid product 6 (34.92 g, 48%). Chiral HPLC conditions for separation of the four possible diastereomers: Chiralcel IA-3, 4.6×150 mm, 3 μm, n-heptane/isopropanol=90/10, isocratic, 40° C., 1.2 mL/min; The ratio of the 2 diastereomers was determined as follows: 4.2 min (7, 0.1%), 5.8 min (6, 99.2%).

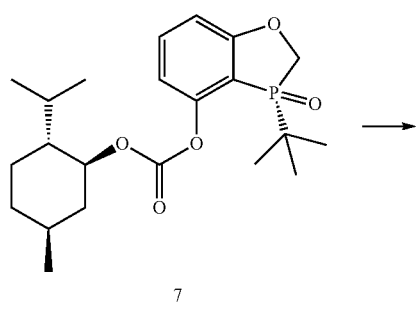

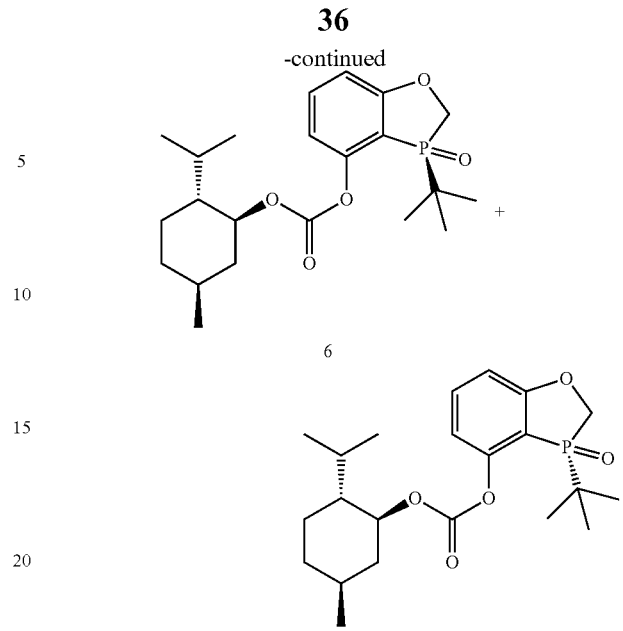

(R)-3-(tert-Butyl)-3-oxido-2H-benzo[d][1,3]oxaphosphol-4-yl ((1S,2R,5S)-2-isopropyl-5-methylcyclohexyl) carbonate (6) via epimerization of (7)

The filtrate from previous experiment was concentrated under reduced pressure. The residue was dissolved in EtOAc (200 mL) and extracted with 0.5 N HCl (100 mL). The organic layer was extracted with water (2×50 mL), dried over MgSO$_4$, filtered and concentrated to give brownish oil (~40 g, ~97.93 mmol). The oil was dissolved in CH$_2$Cl$_2$ (200 mL) and cooled to ~0° C. Oxalyl chloride (18.64 g, 146.89 mmol, 1.50 eq) was added in ~15 min. The mixture was stirred at rt for 20 h. Solvents were removed under vacuum. MeCN (50 mL) and water (5 mL) were added. The mixture was stirred at 60° C. for 2 h, and the resulting suspension was cooled to ~3° C. in an ice-water bath for 1 h. The solid was filtered, rinsed with chilled MeCN (10 mL) and dried to give 6 as white solid (11.86 g, 17% based on 5) with 99.2% chiral purity. Another round of epimerization from the filtrate provided additional amount of 6 (8.25 g, 11%) with chiral purity of 99.5%.

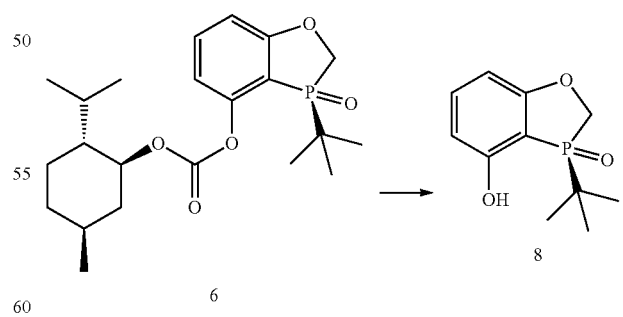

Example 6: (R)-3-(tert-Butyl)-4-hydroxy-2H-benzo[d][1,3]oxaphosphole 3-oxide (8)

To the suspension of 6 (60.36 g, 144.49 mmol) in MeOH (240 mL) was added a solution of NaOH (11.56 g, 288.97, 2.00 eq) in water (60 mL). The mixture was heated to 65° C. and stirred for 2 h. The mixture was cooled to 30° C. and acidified with a solution of 37% HCl (29.9 g, 303.42, 2.10 eq) in water (25 mL) to pH <2. The mixture was distilled at normal pressure to remove volatiles (190 mL). Heptane (300 mL) was added and solvents (150 mL) were distilled at normal pressure. The suspension was cooled to ~3° C. and filtered. The solid was rinsed with water (120 mL), heptane (120 mL), and dried to give 8 as white solid (32.15 g, 98%) with >99.5% ee (the enantiomer 9 was not detected). Chiral HPLC conditions for separation of enantiomers of 8/9: Chiralcel IA-3, 4.6×150 mm, 3 μm, n-heptane/isopropanol=90/10, isocratic, 40° C., 1.2 mL/min; 4.2 min (8), 5.8 min (9).

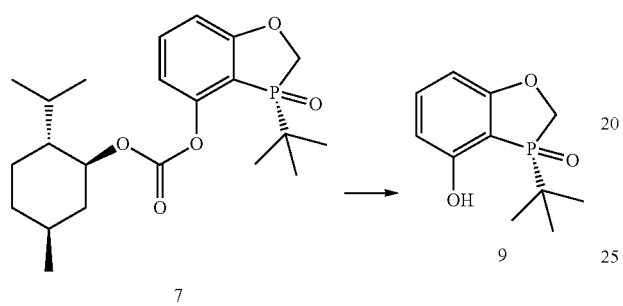

7

(S)-3-(tert-Butyl)-4-hydroxy-2H-benzo[d][1,3]oxaphosphole 3-oxide (9)

To the crude 7 after extractive workup (150.00 g, 367.23 mmol) was added MeOH (50 mL) and a solution of NaOH (22.03 g, 550.85 mol, 1.50 eq). The mixture was heated to 65° C. and held for ~1 h for complete hydrolysis. The mixture was cooled to rt and neutralized with concentrated HCl to pH <2. The solid was filtered, and rinsed with water (200 mL). The solid was suspended in heptane (300 mL) and stirred at rt for 2 h. The suspension was filtered, rinsed with heptane (200 mL) and acetone (200 mL), and dried to give white solid product 9 (80.00 g, 96%) with >99.5% ee (the enantiomer 8 was not detected).

Examples 7-9

Examples 7 to 9 describes how compound Ia is prepared.

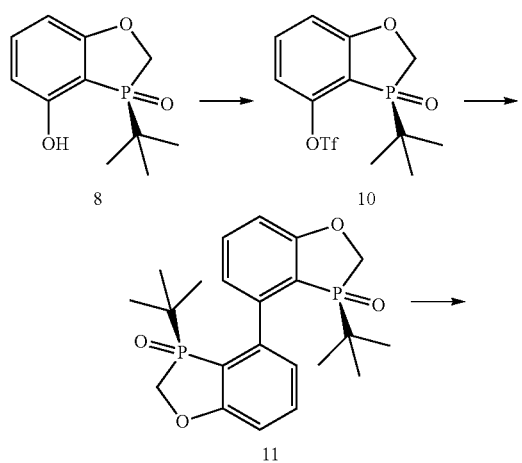

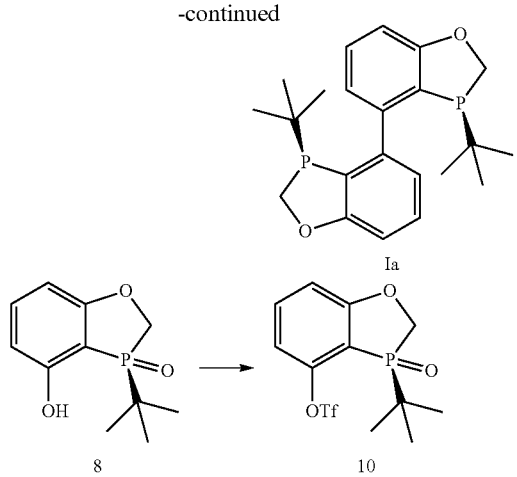

Example 7: (R)-3-(tert-Butyl)-3-oxido-2H-benzo[d][1,3]oxaphosphol-4-yl trifluoromethanesulfonate (10)

To the suspension of (R)-3-(tert-butyl)-4-hydroxy-2H-benzo[d][1,3]oxaphosphole 3-oxide (8, 30.00 g, 132.62 mmol) in CH$_2$Cl$_2$ (300 mL) was added Et$_3$N (26.84 g, 265.24 mmol, 2.00 eq), followed by N,N-bis(trifluoromethylsulfonyl)aniline (PhNTf$_2$) (52.12 g, 145.88 mmol, 1.10 eq). The resulting solution was stirred at room temperature for about 1 h. The mixture was cooled to 0° C., and extracted twice with chilled 5% NaOH (106.10 g, 132.62 mmol, 1.00 eq) each time. The organic layer was separated and neutralized with cold 1 N HCl (265 mL, 2.00 eq) to pH <1. The organic layer was separated, washed with water (100 mL), dried over MgSO4. The mixture was filtered, rinsed with CH$_2$Cl$_2$ (50 mL) and concentrated under reduced pressure to ~120 g. Heptane (190 g) was added and the resulting white suspension was concentrated to remove ~120 g of solvents. The solid was collected by filtration, rinsed with heptane (200 mL) and dried to give (R)-3-(tert-butyl)-3-oxido-2H-benzo[d][1,3]oxaphosphol-4-yl trifluoromethanesulfonate as white solid product 10 (42.62 g, 90%). $^1$H NMR (400 MHz, CDCl$_3$) δ 7.54 (t, J=8.3 Hz, 1H), 7.07 (dd, J=8.2, 3.5 Hz, 1H), 6.97 (dd, J=8.4, 2.5 Hz, 1H), 4.63 (dd, J=14.0, 2.2 Hz, 1H), 4.50 (dd, J=14.0, 10.9 Hz, 1H), 1.26 (d, J=16.8 Hz, 9H); $^{31}$P NMR (162 MHz, CDCl$_3$) δ 61.8.

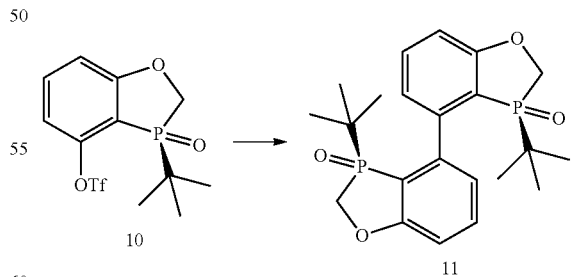

Example 8: (3R,3'R)-3,3'-Di-tert-butyl-2H,2'H-[4,4'-bibenzo[d][1,3]oxaphosphole]3,3'-dioxide (11)

Triflate 10 (43.32 g, 120.91 mmol), KBr (28.78, 241.83 mmol, 2.00 eq), zinc powder (23.71 g, 362.74 mmol, 3.00 eq), Pd$_2$(bda)$_3$ (2.77 g, 3.02 mmol, 0.025 eq), XPhos (4.32 g, 9.07 mmol, 0.075 eq) and N,N-dimethyl acetate (DMAc) (65 mL) were charged under argon. The mixture was evacuated and refilled with argon 3 times. The mixture was heated to 140-150° C. and stirred for ~1.5 h for complete conversion. The reaction mixture was cooled to room temperature, diluted with CH$_2$Cl$_2$ (200 mL) and water (200 mL). The mixture was stirred for ~0.5 h, filtered through a pad of celite and rinsed with CH$_2$Cl$_2$ (100 mL). The organic layer was separated and dried over MgSO$_4$. After filtration, the filtrate and rinse were concentrated. The residue was crystallized from CH$_2$Cl$_2$ and EtOAc (1/1) to give the desired bis-phosphine oxide product 11 (16.77 g, 66%) as white solid. Additional amount of the desired bis-phosphine oxide product 11 (2.57 g, 10%) was obtained from the mother liquor after silica gel column purification. $^1$H NMR (400 MHz, CDCl$_3$) δ 8.13 (dd, J=7.6, 3.7 Hz, 2H), 7.60 (t, J=8.0, 2H), 6.98 (dd, J=8.3, 3.0 Hz, 2H), 4.62 (dd, J=13.9, 2.2 Hz, 2H), 4.44 (dd, J=13.9, 11.1 Hz, 2H), 0.95 (d, J=16.1 Hz, 18H); $^{13}$C NMR (100 MHz, CDCl$_3$) δ 166.8 (d, J=19.0 Hz), 144.6 (d, J=3.7 Hz), 135.5 (d, J=1.3 Hz), 127.1 (d, J=7.1 Hz), 114.6 (d, J=5.2 Hz), 112.3 (d, J=85.7 Hz), 65.6 (d, J=63.3 Hz), 34.3 (d, J=70.9 Hz), 24.5; $^{31}$P NMR (162 MHz, CDCl$_3$) δ 65.6; HRMS (ESI$^+$) cald for C$_{22}$H$_{28}$O$_4$P$_2$+H, 419.1541; found, 419.1545.

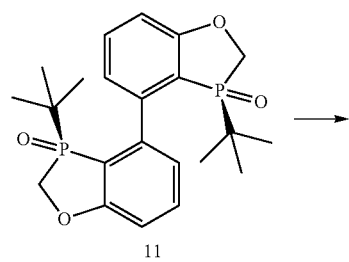

11

Example 9: (3S,3'S)-3,3'-Di-tert-butyl-2,2',3,3'-tetrahydro-4,4'-bibenzo[d][1,3]oxaphosphole (Ia)

To the suspension of phosphine oxide 11 (19.18 g, 45.84 mmol) in THF (40 mL) under argon was added 1,1,3,3-tetramethyldisiloxane (18.47, 137.52 mmol, 3.00 eq) and Ti(OiPr)$_4$ (29.97 g, 105.43 mmo, 2.30 eq). The mixture was stirred at 65° C. for ~2 h for complete reduction as indicated by $^{31}$P NMR. Volatiles (~20 mL) were removed by distillation at normal pressure. Degassed 2-propanol (100 mL) was added and solvents (~80 mL) was removed by distillation at normal pressure. The remaining mixture was cooled to ~55° C. to crystallize the product. The suspension was cooled in an ice-water bath for ~1 h and filtered. The wet cake was rinsed with degassed chilled 2-propanol (80 mL) and dried to constant weight to give the desired bis-phosphine Ia as white crystalline solid (15.43 g, 87%). $^1$H NMR (400 MHz, CDCl$_3$) δ 7.31 (t, J=7.8 Hz, 2H), 7.97 (d, J=7.3 Hz, 2H), 7.90 (d, J=8.1 Hz, 2H), 4.83 (d, J=12.7 Hz, 2H), 4.64 (dd, J=12.6, 24.0 Hz, 2H), 0.67 (d, J=6.1 Hz, 9H), 0.65 (d, J=6.2 Hz, 9H; $^{13}$C NMR (100 MHz, CDCl$_3$) δ 164.1, 134.1, 146.3 (d, J=7.7 Hz), 146.2 (d, J=7.7 Hz), 131.3, 123.0 (d, J=7.2 Hz), 122.9 (d, J=7.2 Hz), 122.7 (d, J=1.8 Hz), 122.7 (d, J=1.8 Hz), 110.2, 70.3 (d, J=14.2 Hz), 70.1 (d, J=14.8 Hz), 31.7 (d, J=7.8 Hz), 31.6 (d, J=7.8 Hz), 27.1 (d, J=7.5 Hz), 27.0 (d, J=7.5 Hz); $^{31}$P NMR (162 MHz, CDCl$_3$) δ −6.5; HRMS (ESI$^+$) cald for C$_{22}$H$_{28}$O$_2$P$_2$+H, 387.1643; found, 387.1650.

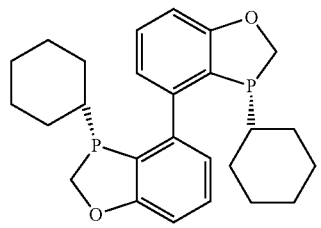

Example 10: (3R,3'R)-3,3'-dicyclohexyl-2,2',3,3'-tetrahydro-4,4'-bibenzo[d][1,3]oxaphosphole Ib Prepared using General Procedure from Example 1 to Example 9, except the diastereomeric (R)- and (S)-3-cyclohexyl-3-oxido-2H-benzo[d][1,3]oxaphosphol-4-yl ((1S,2R,5S)-2-isopropyl-5-methylcyclohexyl) carbonate (6) were separated by chiral SFC. $^1$H (400 MHz, CDCl$_3$) δ=7.32-7.26 (m, 2H), 6.93 (s, 2H), 6.91 (s, 2H), 4.79 (d, J=12.2 Hz, 2H), 4.59 (dd, J=11.7, 23.6 Hz, 2H), 1.60-0.59 (m, 22H). $^{31}$P (162 MHz, CDCl$_3$) δ=−23.07.

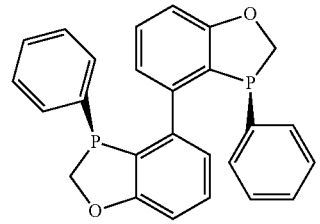

Example 11: (3S,3'S)-3,3'-diphenyl-2,2',3,3'-tetrahydro-4,4'-bibenzo[d][1,3]oxaphosphole (Ic)

Prepared using General Procedure from Example 1 to Example 9, except the diastereomeric (R)- and (S)-3-phenyl-3-oxido-2H-benzo[d][1,3]oxaphosphol-4-yl ((1S,2R,5S)-2-isopropyl-5-methylcyclohexyl) carbonate (6) were separated by chiral SFC. $^1$H NMR (400 MHz, CDCl$_3$) δ 7.30-7.11 (m, 12H), 7.01 (d, J=8.2 Hz, 2H), 6.58 (br, 2H), 4.83-4.60 (m, 4H); $^{13}$C NMR (100 MHz, CDCl$_3$) δ163.6, 145.2, 135.4, 138.3, 132.1, 131.4, 129.3, 128.6, 123.3, 122.3, 111.1, 75.4; $^{31}$P NMR (162 MHz, CDCl$_3$) δ −35.0.

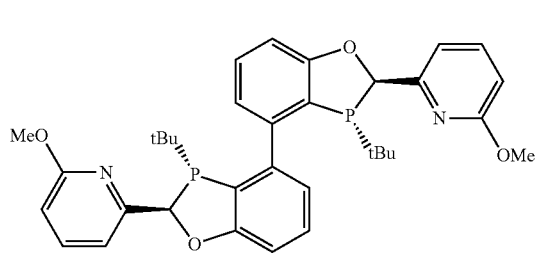

If

Example 12: 6,6'-((2R,2'R,3R,3'R)-3,3'-di-tert-butyl-2,2',3,3'-tetrahydro-[4,4'-bibenzo[d][1,3]oxaphosphole]-2,2'-diyl)bis(2-methoxypyridine) (If)

Prepared using General Procedure from Example 7 to Example 9. The hydroxyl intermediate is prepared through demethylation of the corresponding intermediate reported in J. Org. Chem. 2014, 79, 993. $^1$H NMR (400 MHz, CDCl$_3$) δ 7.53 (t, J=7.8 Hz, 2H), 7.32-7.20 (m, 4H), 7.10-6.90 (m, 2H), 6.54 (d, J=8.2 Hz, 2H), 6.12 (m, 2H), 3.89 (s, 6H), 0.34 (m, 18H); $^{13}$C NMR (100 MHz, CDCl$_3$) 163.6, 163.2, 155.1, 146.5, 138.9, 130.9, 125.03, 123.2, 113.1, 110.4, 108.5, 88.2, 53.4, 33.7, 27.6; $^{31}$P NMR (162 MHz, CDCl$_3$) δ −8.5.

Examples 13 to 19

Example 13 to 19 describes how compound Ig is prepared.

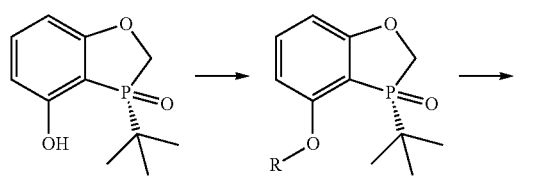

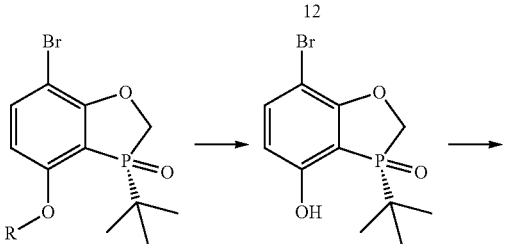

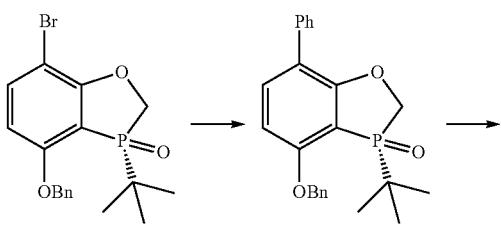

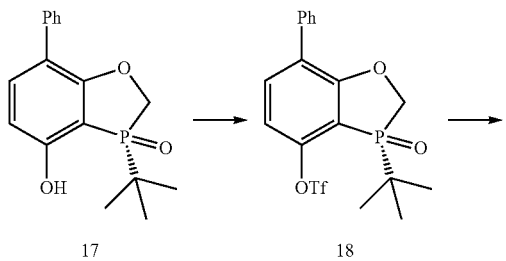

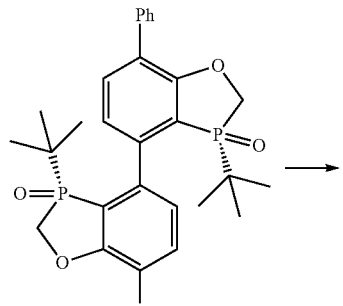

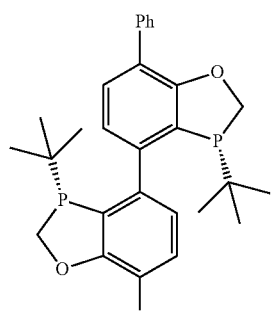

Example 13: (S)-3-(tert-butyl)-4-((tert-butyldiphenylsilyl)oxy)-2H-benzo[d][1,3]oxaphosphole 3-oxide (12)

To the suspension of (S)-3-(tert-butyl)-4-hydroxy-2H-benzo[d][1,3]oxaphosphole 3-oxide (9, 70.00 g, 309.45 mmol) in THF (300 mL) was added, Et$_3$N (58.15 mL, 402.28 mmol, 1.30 eq), TBDPSCl (93.56 g, 340.39 mmol, 1.10 eq) and DMAP (1.89 g, 15.47 mmol, 0.05 eq). The mixture was stirred at room temperature for 5 h. Water (500 mL) and EtOAc (300 mL) were added. The organic layer was separated, concentrated and chased with heptane (500 mL). The residue was triturated with heptane (500 mL). The solid was filtered and rinsed with heptane (150 mL) to give off-white solid product 12 (127.00 g, 88%).

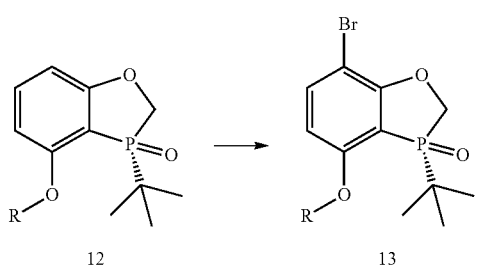

R = TBDPS

Example 14: (S)-7-bromo-3-(tert-butyl)-4-((tert-butyldiphenylsilyl)oxy)-2H-benzo[d][1,3]oxaphosphole 3-oxide (13)

To the suspension of (S)-3-(tert-butyl)-4-((tert-butyldiphenylsilyl)oxy)-2H-benzo[d][1,3]oxaphosphole 3-oxide (12, 50.00 g, 107.62 mmol) in MeCN (100 mL) was added NBS (19.73 g, 110.85 mmol, 1.03 eq) in one portion. The resulting mixture was stirred at room temperature was about 12 h for complete bromination. Water (300 mL) and EtOAc (300 mL) were added. The organic layer was separated and concentrated. The crude residue (13, 58.50 g, 100%) was used in next step without further purification.

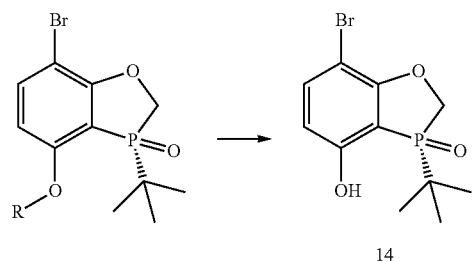

R = TBDPS

Example 15: (S)-7-bromo-3-(tert-butyl)-4-hydroxy-2H-benzo[d][1,3]oxaphosphole 3-oxide (14)

To the solution of (S)-7-bromo-3-(tert-butyl)-4-((tert-butyldiphenylsilyl)oxy)-2H-benzo[d][1,3]oxaphosphole 3-oxide (13, 73.30 g, 157.77 mmol) in THF (200 mL) was added 1M solution of TBAF in THF (100 mL, 100 mol, 0.63 eq). The mixture was stirred at room temperature for 12 h for complete deprotecton. The mixture was concentrated and partitioned between water and EtOAc. The organic layer was separated and concentrated. The residue was filtered through a pad of silica gel, and eluted with first with 30% EtOAc in hexane and then with 10% MeOH in EtOAc. The pure fractions were concentrated to give the desired product as off-white solid product 14 (40.00 g, 83%).

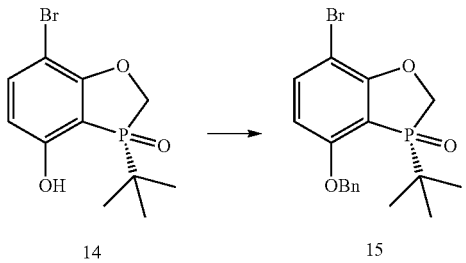 [SMILES: CC(C)(C)[P@@]1(=O)COc2c(Br)ccc(O)c21 ; CC(C)(C)[P@@]1(=O)COc2c(Br)ccc(OCc3ccccc3)c21]

Example 16: (S)-4-(benzyloxy)-7-bromo-3-(tert-butyl)-2H-benzo[d][1,3]oxaphosphole 3-oxide (15)

To the suspension of (S)-7-bromo-3-(tert-butyl)-4-hydroxy-2H-benzo[d][1,3]oxaphosphole 3-oxide (14, 40.00 g, 131.10 mmol) and $K_2CO_3$ (21.74 g, 157.32 mmol, 1.20 eq) in DMF (120 mL) was added BnBr (23.54 g, 137.66, 1.05 eq). The mixture was stirred at room temperature for 12-24 h until the disappearance of the starting material as monitored by HPLC. Water (300 mL) and EtOAc (300 mL) were added. After stirring for about 0.5 h at room temperature, the organic layer was separated and concentrated. The crude product 15 (51.80 g, 100%) was used in next step without further purification.

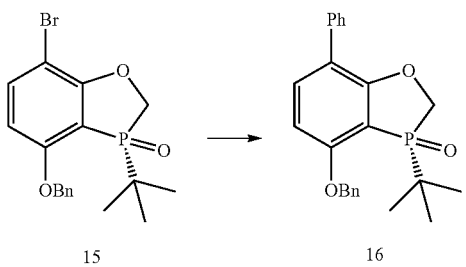 [SMILES: CC(C)(C)[P@@]1(=O)COc2c(Br)ccc(OCc3ccccc3)c21 ; CC(C)(C)[P@@]1(=O)COc2c(-c3ccccc3)ccc(OCc3ccccc3)c21]

Example 17: (S)-4-(benzyloxy)-3-(tert-butyl)-7-phenyl-2H-benzo[d][1,3]oxaphosphole 3-oxide (16)

The mixture of (S)-4-(benzyloxy)-7-bromo-3-(tert-butyl)-2H-benzo[d][1,3]oxaphosphole 3-oxide (15, 23.20 g, 58.70 mmol), $PhB(OH)_2$ (8.59 g, 70.44 mmol, 1.20 eq), $Na_2CO_3$ (14.93 g, 140.88 mmol, 2.40 eq), 1,4-dioxane (120 mL) and water was degased with argon. $PdCl_2(PPh_3)_2$ (0.83 g, 1.17 mmol, 0.02 eq) was added. The mixture was heated to 80° C. under argon for 2 h. The mixture was cooled and water (100 mL) and EtOAc (200 mL) were added. After the mixture was stirred at room temperature for 0.5 h, the organic layer was separated and concentrated to give the crude product 16 (23.00 g, 100%).

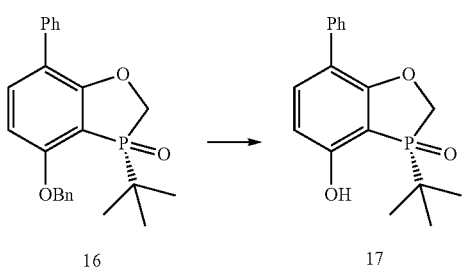 [SMILES: CC(C)(C)[P@@]1(=O)COc2c(-c3ccccc3)ccc(OCc3ccccc3)c21 ; CC(C)(C)[P@@]1(=O)COc2c(-c3ccccc3)ccc(O)c21]

Example 18: (S)-3-(tert-butyl)-4-hydroxy-7-phenyl-2H-benzo[d][1,3]oxaphosphole 3-oxide (17)

The crude (S)-4-(benzyloxy)-3-(tert-butyl)-7-phenyl-2H-benzo[d][1,3]oxaphosphole 3-oxide (16, 23.00 g, 58.61 mmol) was dissolved in MeOH (150 mL) and 10% pallidum over carbon (Degussa Type E101NE/W, 2.00 g) was added. The mixture was hydrogenated at room temperature under 300 psi of $H_2$ for about 48 h. The mixture was filtered and the filtrate was concentrated. The residue was suspended in MeCN (100 mL) and stirred for 0.5 h. The solid was filtered to give white solid product 17 (16.00 g, 90%).

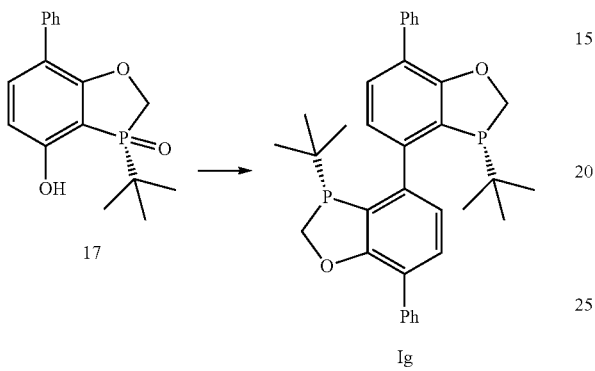

Example 19: (3S,3'S)-3,3'-di-tert-butyl-7,7'-diphenyl-2,2',3,3'-tetrahydro-4,4'-bibenzo[d][1,3]oxaphosphole (Ig)

Prepared using General Procedure from Example 7 to Example 9. $^1$H NMR (400 MHz, $CDCl_3$) δ7.67 (d, J=7.8, 4H), 7.44 (t, J=7.8 Hz, 6H), 7.33 (dd, J=7.9, 6.6 Hz, 2H), 7.10 (d, J=6.6 Hz, 2H), 4.89 (dd, J=12.7, 2H), 4.68 (dd, J=12.7, 23.8 Hz, 2H), 0.74 (d, J=6.2 Hz, 9H), 0.72 (d, J=6.0 Hz, 9H); $^{13}$C NMR (100 MHz, $CDCl_3$) 160.7, 145.3 (d, J=8.0), 145.2 (d, J=8.0 Hz), 138.0, 131.7, 128.8, 128.3, 127.2, 124.4, 124.0 (d, J=7.0 Hz), 123.9 (d, J=7.0 Hz), 123.0, 70.2 (d, J=14.3 Hz), 70.1 (d, J=14.1 Hz), 31.7 (d, J=7.8 Hz), 31.6 (d, J=7.8 Hz), 27.1 (d, J=7.5 Hz), 27.0 (d, J=7.5 Hz); $^{31}$P NMR (162 MHz, $CDCl_3$) δ −6.5.

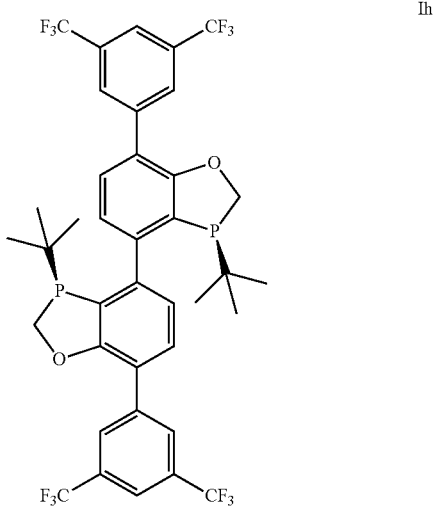 [SMILES: CC(C)(C)[P@]1COc2c(-c3cc(C(F)(F)F)cc(C(F)(F)F)c3)ccc(-c3ccc(-c4cc(C(F)(F)F)cc(C(F)(F)F)c4)c4c3[P@](C(C)(C)C)CO4)c21]

Example 20: (3S,3'S)-7,7'-bis(3,5-bis(trifluoromethyl)phenyl)-3,3'-di-tert-butyl-2,2',3,3'-tetrahydro-4,4'-bibenzo[d][1,3]oxaphosphole (Ih)

Prepared using General Procedure from Example 17 to Example 19. $^1$H NMR (400 MHz, $CDCl_3$) 8.13 (s, 4H), 7.84 (s, 2H), 7.50 (d, J=8.0 Hz, 2H), 7.16 (d, J=7.8 Hz, 2H), 4.96 (d, J=12.7, 2H), 4.73 (dd, J=12.7, 23.7 Hz, 2H), 0.75 (d, J=6.2 Hz, 9H), 0.73 (d, J=6.2 Hz, 9H); $^{31}$P NMR (162 MHz, $CDCl_3$) δ −7.8.

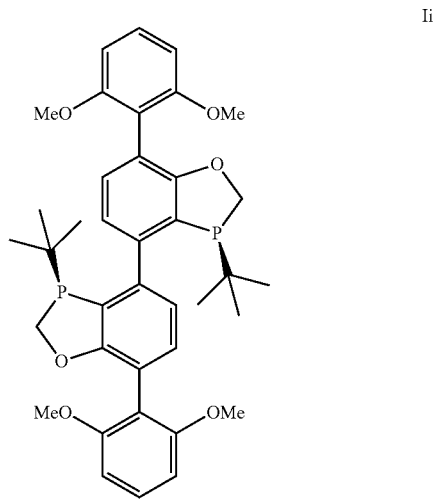 [SMILES: COc1cccc(OC)c1-c1ccc(-c2ccc(-c3c(OC)cccc3OC)c3c2[P@](C(C)(C)C)CO3)c2c1OC[P@@]2C(C)(C)C]

Example 21: (3S,3'S)-3,3'-di-tert-butyl-7,7'-bis(2,6-dimethoxyphenyl)-2,2',3,3'-tetrahydro-4,4'-bibenzo[d][1,3]oxaphosphole (Ii)

Prepared using General Procedure from Example 17 to Example 19. $^1$H NMR (400 MHz, $CDCl_3$) 7.21 (t, J=8.3, 2H), 7.14 (d, J=7.6 Hz, 2H), 7.02 (d, J=7.2 Hz, 2H), 6.59 (d, J=8.3 Hz, 4H), 4.69 (d, J=12.6, 2H), 4.52 (dd, J=12.6, 23.9 Hz, 2H), 0.71 (d, J=6.1 Hz, 9H), 0.69 (d, J=6.1 Hz, 9H); $^{13}$C NMR (100 MHz, $CDCl_3$) 161.9, 158.3, 157.9, 145.3 (d, J=7.9), 145.2 (d, J=7.9 Hz), 133.6, 129.0, 122.5 (d, J=6.7 Hz), 122.4 (d, J=6.7 Hz), 122.1, 70.0 (d, J=14.0 Hz), 69.9 (d, J=13.8 Hz), 56.2, 55.8, 31.6 (d, J=7.8 Hz), 31.5 (d, J=7.8 Hz), 27.1 (d, J=7.5 Hz), 27.0 (d, J=7.5 Hz); $^{31}$P NMR (162 MHz, $CDCl_3$) δ −5.5.

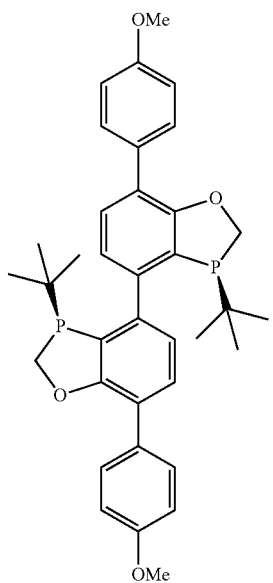

Ij

Example 22: (3S,3'S)-3,3'-di-tert-butyl-7,7'-bis(4-methoxyphenyl)-2,2',3,3'-tetrahydro-4,4'-bibenzo[d][1,3]oxaphosphole (Ij)

Prepared using General Procedure from Example 17 to Example 19. $^1$H NMR (400 MHz, CDCl$_3$) δ 7.65 (d, J=8.3, 4H), 7.44 (d, J=7.6 Hz, 2H), 7.11 (d, J=7.7 Hz, 2H), 7.01 (d, J=8.3 Hz, 4H), 4.91 (d, J=12.9 Hz, 2H), 4.70 (dd, J=12.6, 23.7 Hz, 2H), 3.88 (br s, 6H), 0.77 (d, J=6.1 Hz, 9H), 0.74 (d, J=6.1 Hz, 9H); $^{13}$C NMR (100 MHz, CDCl$_3$) 160.6, 158.9, 144.8 (d, J=7.9), 144.7 (d, J=7.9 Hz), 131.3, 130.4, 129.9, 124.0, 123.8 (d, J=7.0 Hz), 123.7 (d, J=7.0 Hz), 123.0, 113.7, 70.1 (d, J=14.2 Hz), 69.9 (d, J=14.0 Hz), 55.3, 31.7 (d, J=7.8 Hz), 31.6 (d, J=7.7 Hz), 27.1 (d, J=7.5 Hz), 27.0 (d, J=7.5 Hz); $^{31}$P NMR (162 MHz, CDCl$_3$) δ −6.8.

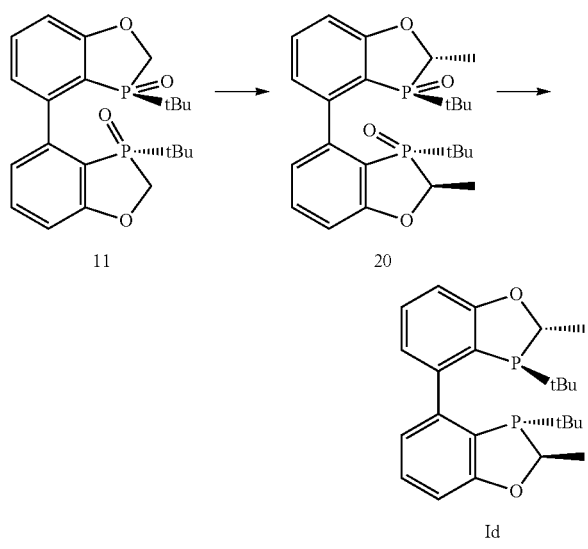

Example 23: (2R,2'R,3R,3'R)-3,3'-di-tert-butyl-2,2'-dimethyl-2,2',3,3'-tetrahydro-4,4'-bibenzo[d][1,3]oxaphosphole (Id)

To a solution of bisphosphine oxide 11 (0.50 g, 1.19 mmol, 1 equiv) in THF (10 mL) at −78° C. was added LDA (1.5 mL, 2 M in THF/toluene, 2.99 mmol, 2.5 equiv). The mixture was stirred at −78° C. for 1 h before addition of iodomethane (0.19 mL, 2.99 mmol, 2.5 equiv). The resulting mixture was kept at −78° C. for 1.5 h before it was warmed to r.t. Added water and extracted with dichloromethane. The organic layer was dried over magnesium sulfate, concentrated, and purified by silica gel column chromatography (0-10% methanol in dichloromethane) to give the desired product 20 (0.47 g, 1.06 mmol, 89%) as white solid.

To a solution of bismethylated bisphosphine oxide 20 (400 mg, 0.90 mmol) in THF (4 mL) at r.t. was added PMHS (0.6 g) and Ti(OiPr)$_4$ (0.6 mL, 2.06 mmol, 2.3 equiv). The mixture was stirred at 60° C. for 20 h, and then concentrated under vacuum to remove most THF. 30% aqueous NaOH solution (4 mL) was carefully added to the residue. Gas was generated during addition. The resulting mixture was further stirred at 65° C. for 0.5 h. To the mixture at r.t. was added MTBE (3×4 mL). The MTBE solution was dried, concentrated, and purified by passing through a neutral alumina plug affording the desired product Id as white solid (334 mg, 0.81 mmol, 90%). $^1$H NMR (400 Mz CDCl$_3$): δ 7.21 (t, J=6.4 Hz, 2H), 6.90 (bs, 2H), 6.80 (d, J=6.4 Hz, 2H), 4.93 (q, J=5.6 Hz, 2H), 1.46 (dd, J=12.8, 5.6 Hz, 6H), 0.58 (t, J=4.8 Hz, 18H); $^{31}$P NMR (162 MHz, CDCl$_3$): δ 9.4; $^{13}$C NMR (100 MHz, CDCl$_3$): δ 163.2, 146.7, 131.0, 122.3, 110.3, 79.5 (t, J=1 Hz), 31.6, 29.7, 27.1 (t, J=7 Hz), 21.3 (t, J=15 Hz).

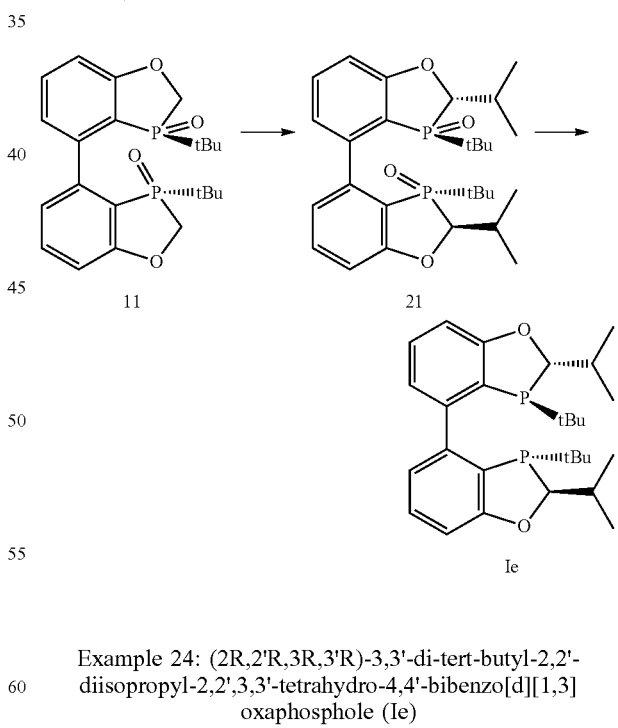

Example 24: (2R,2'R,3R,3'R)-3,3'-di-tert-butyl-2,2'-diisopropyl-2,2',3,3'-tetrahydro-4,4'-bibenzo[d][1,3]oxaphosphole (Ie)

To a solution of bisphosphine oxide 11 (400 mg, 0.96 mmol, 1 equiv) in THF (4 mL) at −78° C. was added LDA (1.2 mL, 2 M in THF/toluene, 2.39 mmol, 2.5 equiv). The mixture was stirred at −78° C. for 1 h before addition of iPrI (0.24 mL, 2.39 mmol, 2.5 equiv). The resulting mixture was kept at −78° C. for 1.5 h before it was warmed to r.t. After stirring overnight, added water and extracted with dichloromethane. The organic layer was dried over magnesium sulfate, concentrated, and purified by silica gel column chromatography (0-10% methanol in EtOAc) to give the desired product 21 (341 mg, 0.68 mmol, 71%) as white solid.

To a solution of bismethylated bisphosphine oxide 21 (300 mg, 0.60 mmol) in THF (3 mL) at r.t. was added PMHS (0.5 g) and Ti(OiPr)$_4$ (0.44 mL, 1.49 mmol, 2.5 equiv). The mixture was stirred at 60° C. for 20 h, and then concentrated under vacuum to remove most THF. 30% aqueous NaOH solution (4 mL) was carefully added to the residue. Gas was generated during addition. The resulting mixture was further stirred at 65° C. for 0.5 h. To the mixture at r.t. was added MTBE (3×4 mL). The MTBE solution was dried, concentrated, and purified by passing through a neutral alumina plug affording the desired product Ie as white solid (253 mg, 0.54 mmol, 90%). $^1$H NMR (400 Mz CDCl$_3$): δ 7.26 (t, J=6.4 Hz, 2H), 6.90 (bs, 2H), 6.86 (d, J=6.4 Hz, 2H), 4.58 (d, J=5.6 Hz, 2H), 2.14 (hp, J=5.6 Hz, 2H), 1.07 (t, J=5.6 Hz, 12H), 0.63 (t, J=4.8 Hz, 18H); $^{31}$P NMR (162 MHz, CDCl$_3$): δ −3.0; $^{13}$C NMR (100 MHz, CDCl$_3$): δ 164.5, 146.3, 130.8, 122.7, 109.5, 90.1 (t, J=14 Hz), 32.8, 31.4, 27.0, 19.1.

=7.56 min, rt (minor)=9.45 min). The absolute configurations of products were determined by comparison with authentic sample. $^1$H NMR (500 MHz, CDCl$_3$) δ 7.32-7.22 (m, 3H), 7.66-7.10 (m, 2H), 5.00 (d, J=7.1 Hz, 1H), 4.62-4.55 (m, 1H), 3.70 (s, 3H), 3.15-3.00 (m, 2H), 1.41 (s, 9H) ppm; $^{13}$C NMR (125 MHz, CDCl$_3$) δ 172.3, 155.1, 136.0, 129.3, 128.5, 127.0, 79.9, 54.4, 52.2, 38.4, 28.3 ppm.

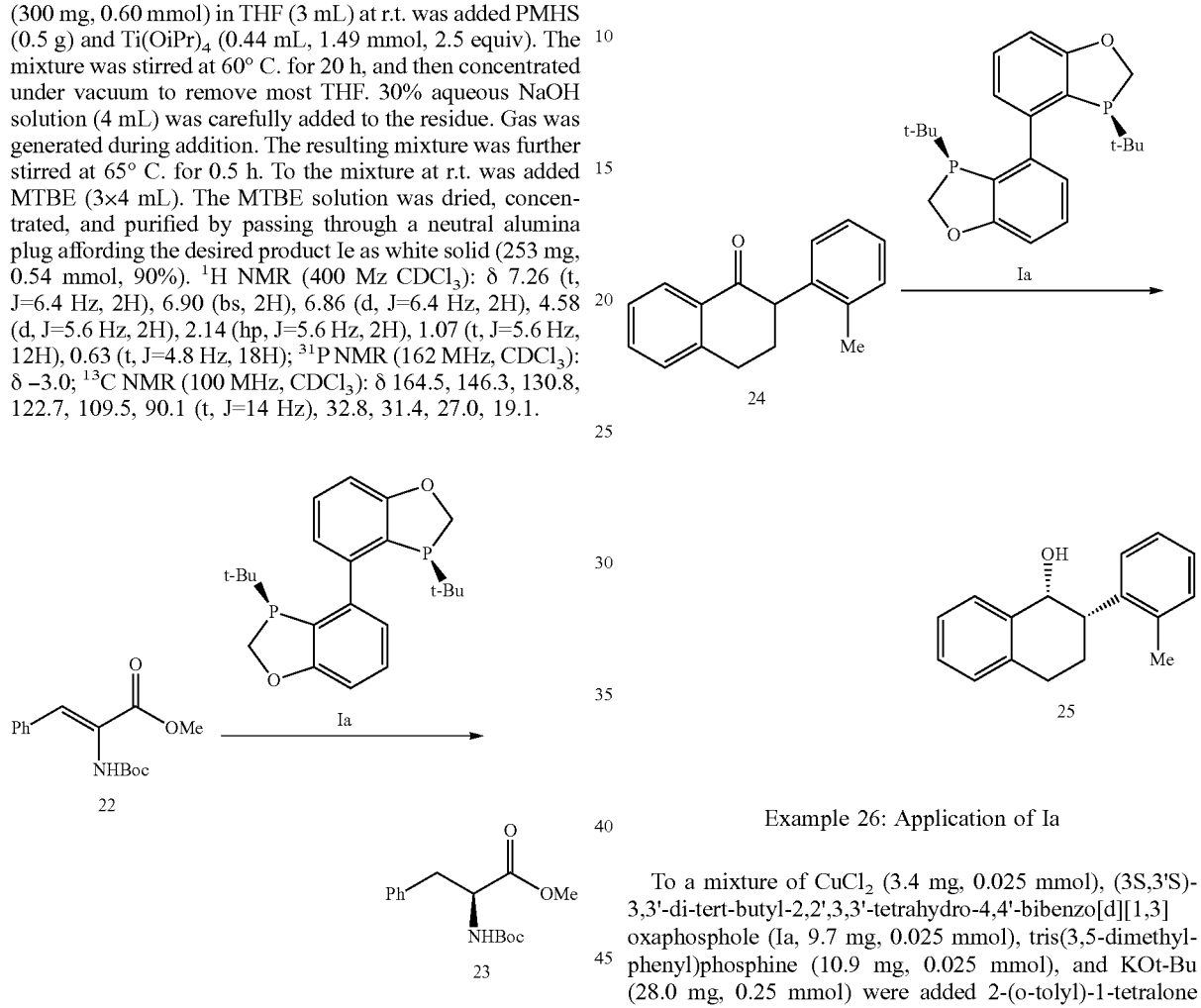

Example 26: Application of Ia

To a mixture of CuCl$_2$ (3.4 mg, 0.025 mmol), (3S,3'S)-3,3'-di-tert-butyl-2,2',3,3'-tetrahydro-4,4'-bibenzo[d][1,3]oxaphosphole (Ia, 9.7 mg, 0.025 mmol), tris(3,5-dimethylphenyl)phosphine (10.9 mg, 0.025 mmol), and KOt-Bu (28.0 mg, 0.25 mmol) were added 2-(o-tolyl)-1-tetralone (24, 118 mg, 0.5 mmol) and IPA (2 mL) under nitrogen. The reaction vessel was transferred into an autoclave and pressurized with hydrogen to 400 psi. The reaction mixture was stirred at this pressure and 20° C. for 24 h. After release of the hydrogen and purging with nitrogen, the reaction mixture was filtered through a plug of celite, the solvent was removed under reduced pressure, and the product was purified by silica gel column chromatography (eluent: 0-10% EtOAc in hexanes) to afford the alcohol 25 (107 mg, 90%, >99:1 dr, 91:9 er). The enantiomeric excess of the products was determined by chiral HPLC with a Chiralpak IB-3 (4.6×250 mm) column (heptane/(60% dichloromethane+40% denatured ethanol)=99.8:0.2, 1.5 mL/min, 20° C., rt (major)=7.08 min, rt (minor)=16.18 min). $^1$H NMR (500 MHz, CDCl$_3$) δ 7.31-7.13 (8, 8H), 4.67 (d, J=2.4 Hz, 1H), 3.28 (dt, J=12.8 Hz, 2.6 Hz, 1H), 3.05-2.85 (m, 2H), 2.46 (dq, J=12.6 Hz, 5.5 Hz, 1H), 3.33 (s, 3H), 1.86-1.75 (m, 1H) ppm. $^{13}$C NMR (125 MHz, CDCl$_3$) δ 140.5, 137.9, 136.9, 136.0, 130.8, 130.6, 129.2, 128.1, 128.0, 126.7, 126.3, 126.2, 68.9, 42.1, 30.2, 22.2, 19.6 ppm.

Example 25: Application of Ia

A solution of Rh(NBD)$_2$BF$_4$ (1.1 mg, 0.003 mmol) and (3S,3'S)-3,3'-di-tert-butyl-2,2',3,3'-tetrahydro-4,4'-bibenzo[d][1,3]oxaphosphole (Ia, 1.2 mg, 0.003 mmol) in 1.5 mL of N$_2$-purged methanol was stirred for 20 min under nitrogen. Methyl (Z)-2-((tert-butoxycarbonyl)amino)-3-phenylacrylate 22 (83 mg, 0.3 mmol) was then added. The reaction vessel was transferred into an autoclave and pressurized with hydrogen to 100 psi. The reaction mixture was stirred at this pressure and 20° C. for 24 h. After release of the hydrogen and purging with nitrogen, the reaction mixture was concentrated under reduced pressure, and the product was purified by silica gel column chromatography (eluent: 0-10% EtOAc in hexanes) to afford the acetamide 23 (76 mg, 91%, 99.3:0.7 er). The enantiomeric excess of the hydrogenation products was determined by chiral HPLC with a Kromasil 3-Amicoat (4.6×250 mm) column (heptane/denatured ethanol=95:5, 1.3 mL/min, 25° C., rt (major)

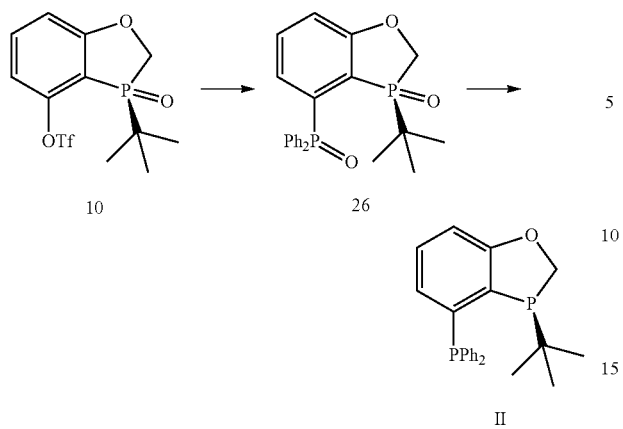

Example 27: (S)-3-(tert-butyl)-4-(diphenylphosphanyl)-2,3-dihydrobenzo[d][1,3]oxaphosphole (II)

The mixture of (R)-3-(tert-butyl)-3-oxido-2H-benzo[d][1,3]oxaphosphol-4-yl trifluoromethanesulfonate (10, 2.00 g, 5.58 mmol), diphenylphosphine oxide (1.24 g, 6.14 mmol, 1.10 eq), palladium acetate (0.05 g, 0.22 mmol, 0.04 eq), 1,4-bis(diphenylphosphanyl)butane (0.19 g, 0.15 mmol, 0.08 eq), N,N-diisopropylethylamine (2.89 g, 22.33 mmol, 4.00 eq) and DMSO (30 mL) was heated at 80° C. under argon for 12 h. On cooling, the mixture was quenched with diluted hydrochloric acid and extracted with ethyl acetate. The combined organic layer was dried, concentrated, and purified on silica gel (7% MeOH in EtOAc) to give (R)-3-(tert-butyl)-4-(diphenylphosphoryl)-2H-benzo[d][1,3]oxaphosphole 3-oxide (26, 1.25 g) in 54% yield.

A mixture of (R)-3-(tert-butyl)-4-(diphenylphosphoryl)-2H-benzo[d][1,3]oxaphosphole 3-oxide (26, 1.72 g, 4.19 mmol), 1,1,3,3-tetramethyldisiloxane (1.69 g, 12.57 mmol, 3.00 eq) and titanium isopropoxide (2.74 g, 9.64 mmol, 2.30 eq) and THF (3.5 mL) was heated t0 70° C. under argon for 3 h. The mixture were distilled under argon and normal pressure to remove volatiles, and chased with IPA (2×5 mL). The suspension was cooled to 0° C., filtered under argon and rinsed with cold IPA. The solid was dried by passing argon though to give white solid product II (1.12 g) in 70% yield. $^1$H NMR (400 MHz, CDCl$_3$) δ 7.45-7.20 (m, 13H), 6.91 (d, J=8.0 Hz, 1H), 6.68 (m, 1H), 4.89 (d, J=12.6 Hz, 1H), 4.47 (dd, J=12.6, 25.4 Hz, 1H), 1.04 (d, J=11.9 Hz); $^{31}$P NMR (162 MHz, CDCl$_3$) δ −5.6 (d, J=70.2 Hz, 1P), −12.8 (d, J=70.0 Hz, 1P).

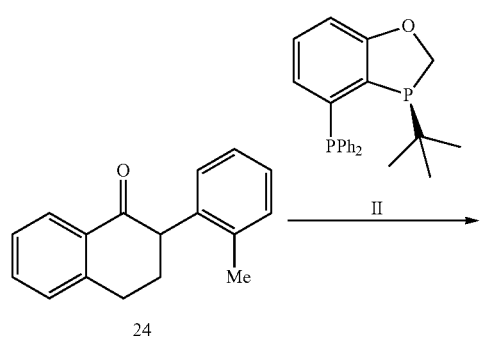

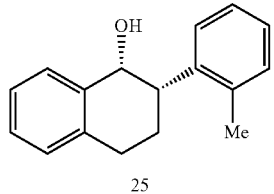

Example 28: Application of II. (1R,2S)-2-phenyl-1,2,3,4-tetrahydronaphthalen-1-ol (25)

To a mixture of CuCl$_2$ (3.4 mg, 0.025 mmol), ligand II, tris(3,5-dimethylphenyl)phosphine (10.9 mg, 0.025 mmol), and KOt-Bu (28.0 mg, 0.25 mmol) were added 2-(o-tolyl)-1-tetralone (24, 118 mg, 0.5 mmol) and IPA (2 mL) under nitrogen. The reaction vessel was transferred into an autoclave and pressurized with hydrogen to 400 psi. The reaction mixture was stirred at this pressure and 20° C. for 24 h. After release of the hydrogen and purging with nitrogen, the reaction mixture was filtered through a plug of celite, the solvent was removed under reduced pressure, and the product was purified by silica gel column chromatography (eluent: 0-10% EtOAc in hexanes) to afford the alcohol 25 (107 mg, 90%, 94:6 dr, 52:48 er). The enantiomeric excess of the products was determined by chiral HPLC with a Chiralpak IB-3 (4.6×250 mm) column (heptane/(60% dichloromethane+40% denatured ethanol)=99.8:0.2, 1.5 ml/min, 20° C., rt (major)=7.08 min, rt (minor)=16.18 min). $^1$H NMR (500 MHz, CDCl$_3$) δ 7.31-7.13 (8, 8H), 4.67 (d, J=2.4 Hz, 1H), 3.28 (dt, J=12.8 Hz, 2.6 Hz, 1H), 3.05-2.85 (m, 2H), 2.46 (dq, J=12.6 Hz, 5.5 Hz, 1H), 3.33 (s, 3H), 1.86-1.75 (m, 1H) ppm. $^{13}$C NMR (125 MHz, CDCl$_3$) δ 140.5, 137.9, 136.9, 136.0, 130.8, 130.6, 129.2, 128.1, 128.0, 126.7, 126.3, 126.2, 68.9, 42.1, 30.2, 22.2, 19.6 ppm.

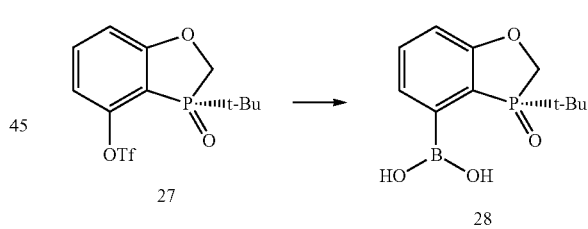

Example 29: (S)-(3-(tert-butyl)-3-oxido-2H-benzo[d][1,3]oxaphosphol-4-yl)boronic acid (28)

To a mixture of triflate 27 (2.00 g, 5.58 mmol), pinacol diborane (4.25 g, 16.75 mmol), Pd(dppf)Cl$_2$ (0.228 g, 0.28 mmol) and CsF (2.54 g, 16.75 mmol) in DMAc (54 mL) was heated to 80° C. under argon for 3 h. The mixture was diluted with water (200 mL) and MTBE (200 mL). The aqueous was extracted with MTBE (2×100 mL) and all three organic layers were combined. After filtration through a pad of Celite, the solvent was distilled. The residue was extracted with 1% NaOH (150 mL). After discarding the organic layer, the pH of the aqueous was adjusted to 6 and the product was extracted with MTBE (100 mL). The product 28 was thus isolated via crystallization in MTBE/hexanes. $^1$H NMR (500 MHz, DMSO) δ: 1.12 (d, J=16.5 Hz, 9H), 4.41 (dd, J=14.0, 10.0 Hz, 1H), 5.04 (d, J=14.0 Hz, 1H), 7.17 (dd, J=8.0, 3.5 Hz, 1H), 7.54 (dd, J=7.0, 2.5 Hz, 1H), 7.65 (t, J=8.0 Hz, 1H); $^{13}$C NMR (125 MHz, DMSO) δ: 22.9, 34.0 (d, J=67.8 Hz), 64.7 (d, J=61.5 Hz), 116.1 (d, J=83.5 Hz), 116.2 (d, J=1.6 Hz), 129.7 (d, J=10.0 Hz), 135.5 (d, J=1.9 Hz), 164.3 (d, J=20.9 Hz).

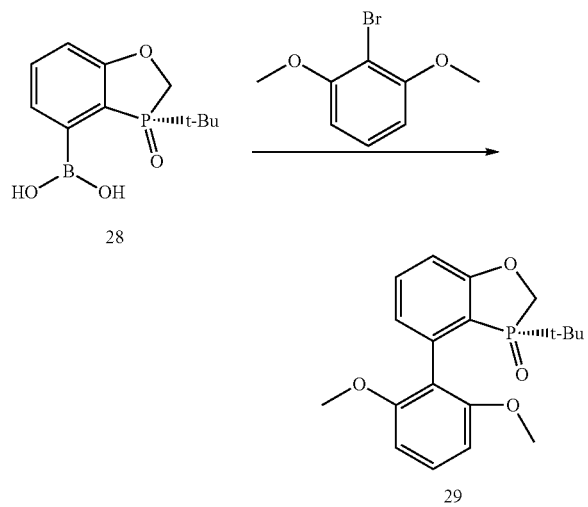

28

29

Example 30: (S)-3-(tert-butyl)-4-(2,6-dimethoxyphenyl)-2H-benzo[d][1,3]oxaphosphole 3-oxide (29)

To a mixture of boronic acid 28 (50.0 mg, 0.197 mmol), 2,6-dimethoxyphenylbromide (42.7 mg, 0.197 mmol), Pd$_2$(dba)$_3$ (18.0 mg, 0.02 mmol), BIDIME (13.0 mg, 0.039 mmol) and K$_2$CO$_3$ (81.6 mg, 0.590 mmol) in THF (0.5 mL) and water (0.13 mL) was heated to 70° C. under argon for 10 h. The mixture was diluted with water (2 mL) and EtOAc (2 mL). The solvent was removed and the residue was subjected to silica gel column purification using DCM/MeOH to afford the desired product 29 in 40% yield. $^1$H NMR (400 MHz, DMSO): δ=0.87 (d, J=15.9 Hz, 9H), 3.70 (s, 3H), 3.77 (s, 3H), 4.34 (dd, J=13.7, 10.5 Hz, 1H), 4.47 (dd, J=13.8, 1.8 Hz, 1H), 6.55 (d, J=8.4 Hz, 1H), 6.64 (d, J=8.4 Hz, 1H), 6.89 (m, 2H), 7.28 (t, J=8.4 Hz, 1H), 7.46 (t, J=7.9 Hz, 1H).

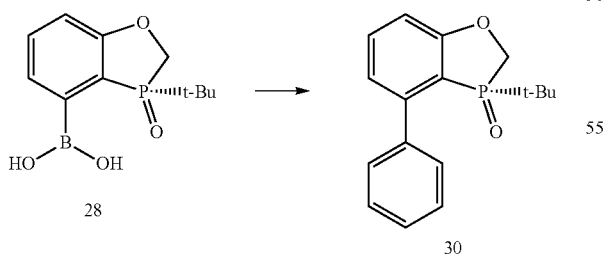

28

30

Example 31: (S)-3-(tert-butyl)-4-phenyl-2H-benzo[d][1,3]oxaphosphole 3-oxide (30)

To a mixture of boronic acid 28 (50.0 mg, 0.197 mmol), iodobenzene (40.0 mg, 0.197 mmol), Pd$_2$(dba)$_3$ (18.0 mg, 0.02 mmol), BIDIME (13.0 mg, 0.039 mmol) and K$_2$CO$_3$ (81.6 mg, 0.590 mmol) in THF (0.5 mL) and water (0.13 mL) was heated to 70° C. under argon for 10 h. The mixture was diluted with water (2 mL) and EtOAc (2 mL). The solvent was removed and the residue was subjected to silica gel column purification using DCM/MeOH to afford the desired product 30 in 50% yield. $^1$H NMR (400 MHz, DMSO) δ: 0.71 (d, J=16.0 Hz, 9H), 4.40 (dd, J=14.4, 10.8 Hz, 1H), 4.91 (dd, J=14.4, 1.6 Hz, 1H), 7.06 (dd, J=8.0, 2.8 Hz, 1H), 7.12 (dd, J=7.6, 3.6 Hz, 1H), 7.48 (m, 3H), 7.64 (m, 1H), 7.78 (m, 2H).

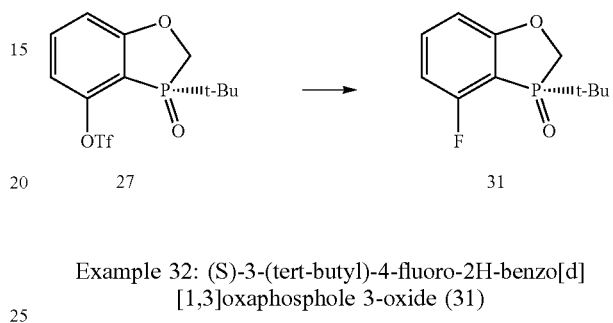

27

31

Example 32: (S)-3-(tert-butyl)-4-fluoro-2H-benzo[d][1,3]oxaphosphole 3-oxide (31)

To a mixture of triflate 27 (10.70 g, 29.87 mmol), CsF (13.61 g, 89.60 mmol), Pd$_2$(dba)$_3$ (0.69 g, 1.20 mmol) and AdbrettPhos (0.77 g, 1.20 mmol) in toluene (100 mL) was heated to reflux under argon for 10 h. The mixture was cooled to room temperature and filtered through a pad of Celite. After removing solvent, the product 31 was isolated via silica gel column chromatography using DCM/MeOH. $^1$H NMR (400 MHz, DMSO) δ: 1.18 (d, J=16.4 Hz, 9H), 4.45 (dd, J=10.0, 6.8 Hz, 1H), 4.97 (dd, J=14.4, 3.2 Hz, 1H), 6.95 (m, 2H), 7.64 (m, 1H).

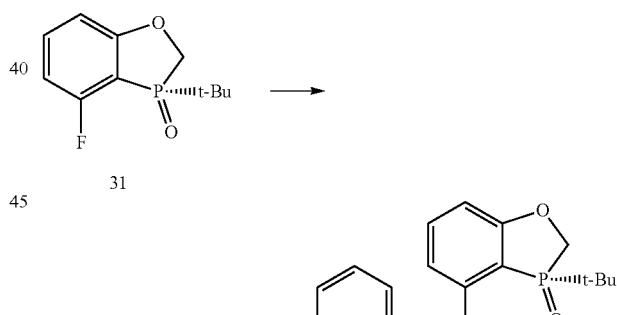

31

32

Example 33: (S)-4-(benzylamino)-3-(tert-butyl)-2H-benzo[d][1,3]oxaphosphole 3-oxide (32)

To a mixture of fluoride 31 (0.50 g, 2.19 mmol) in DMSO (0.5 mL) was added BnNH$_2$ (0.94 g, 8.76 mmol) and heated to 150° C. under argon for 10 h. The mixture was cooled to room temperature and diluted with MTBE (5 mL) and water (5 mL). The aqueous layer was discarded. After removing solvent, the product 32 was purified via silica gel column chromatography using MTBE/hexanes in 66% yield. $^1$H NMR (400 MHz, CDCl$_3$) δ: 1.29 (d, J=16.4 Hz, 9H), 4.37 (m, 3H), 4.53 (d, J=12.0 Hz, 1H), 5.18 (t, J=6.0 Hz, 1H), 6.23 (m, 2H), 7.33 (m, 6H); $^{13}$C NMR (100 MHz, CDCl$_3$) δ: 24.3, 35.1 (d, J=31 Hz), 47.9, 65.5 (d, J=59 Hz), 102.3 (d, J=5 Hz), 104.0 (d, J=6 Hz), 127.4 (d, J=12 Hz), 128.7, 136.6, 138.3, 151.3 (d, J=4 Hz), 165.57; $^{31}$P NMR (162 MHz, CDCl$_3$) δ: 66.72.

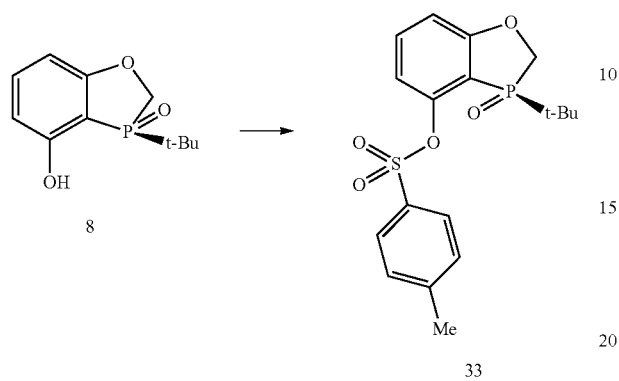

Example 34: (R)-3-(tert-butyl)-3-oxido-2H-benzo[d][1,3]oxaphosphol-4-yl 4-methylbenzenesulfonate (33)

To a solution of (R)-3-(tert-butyl)-4-hydroxy-2H-benzo[d][1,3]oxaphosphole 3-oxide (8, 2 g, 8.841 mmol, 1 equiv) in DCM (16 mL) at r.t. was added p-tolylsulfonyl chloride (2.02 g, 10.610 mmol, 1.2 equiv). To the resulting mixture was charged trimethylamine (5.76 g, 17.68 mmol, 2.0 equiv) over 5 min. After stirring at r.t. overnight, water (15 mL) and dichloromethane (20 mL) were added to the mixture. The dichloromethane solution was washed with water (20 mL), dried over magnesium sulfate, concentrated and purified by silica gel column chromatography (0-100% EtOAc in hexanes) to give product 33 (3.16 g, 8.3 mmol, 94%) as white solid. $^1$H NMR (400 MHz, CDCl3) δ 7.97 (d, J=8.0 Hz, 2H), 7.43 (t, J=8.4 Hz, 1H), 7.33 (d, J=8.4 Hz, 1H), 7.24 (dd, J=8.0, 3.6 Hz, 1H), 6.81 (dd, J=8.0, 2.4 Hz, 1H), 4.53 (dd, J=14.0, 2.4 Hz, 1H), 4.40 (dd, J=14.0, 10.8 Hz, 1H), 2.42 (s, 3H), 1.19 (d, J=16.8 Hz, 9H); $^{31}$P NMR (162 MHz, CDCl3) δ 61.8; $^{13}$C NMR (100 MHz, CDCl3) δ 166.4 (d, J=17.0 Hz), 150.6, 145.8, 136.1, 132.2, 129.8, 129.0, 112.9 (d, J=5 Hz), 111.9 (d, J=5 Hz), 107.6, 106.7, 66.2 (d, J=59.0 Hz), 33.9 (d, J=73.0 Hz), 24.2, 21.8.

Examples 35 to 46

Examples 35 to 46 illustrates how (4S)-3-(tert-butyl)-4-(2,6-dimethoxyphenyl)-6-methoxy-2H-benzo[d][1,3]oxaphosphole (47) is prepared:

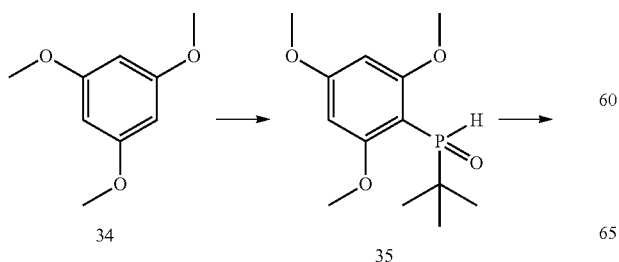

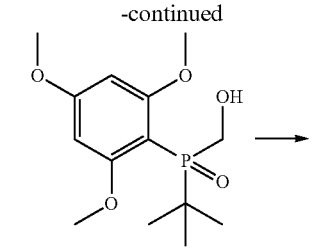

36

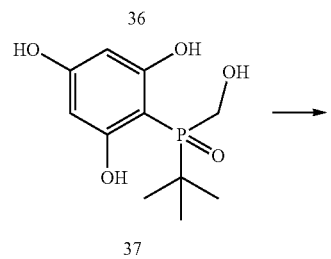

37

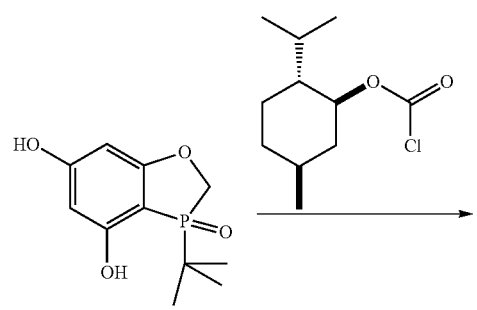

38

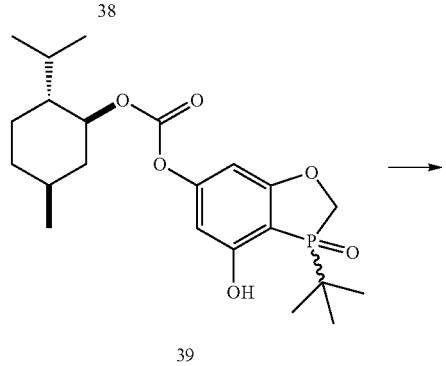

39

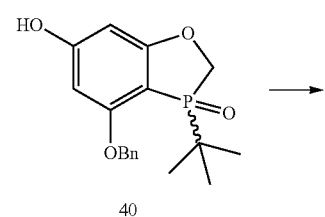

40

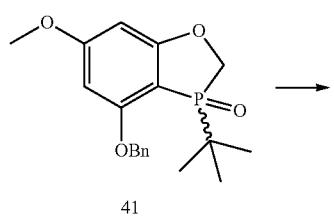

41

-continued

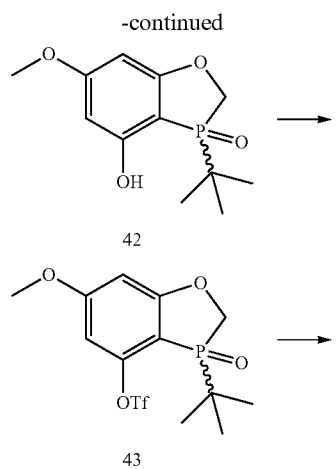

42

43

44

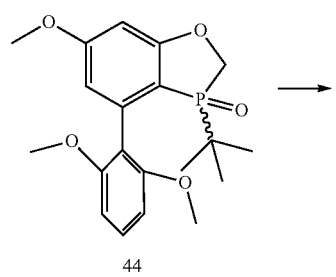

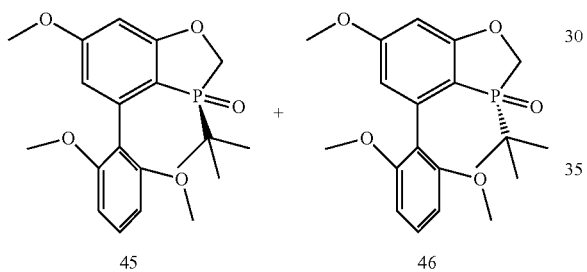

45     46

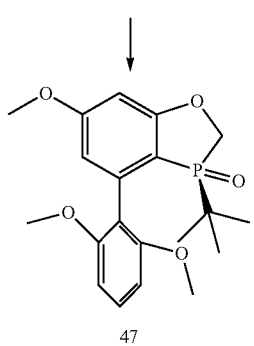

47

Example 35: tert-butyl(2,4,6-trimethoxyphenyl)phosphine oxide (35)

To a solution of 1,3,5-trimethoxybenzene (34, 47.00 g, 0.28 mol) in THF (300 ml) at −20° C. was added 2.5 M n-BuLi in hexane (129 mL, 0.32 mol, 1.15 eq). The mixture was warmed to 0° C. and stirred for 1 h. The mixture was cooled to −65° C. and tert-butyldichlorophosphane (44.43 g, 0.28 mol, 1.00 eq) was added. After the mixture was stirred at −25 to −5° C. for 0.5 h, water (200 mL) was added. The mixture was stirred at rt for 12 h, concentrated, and extracted with DCM (2×300 mL). The extracts were concentrated to give the desired product 35 as an oil (62.39 g, 82%).

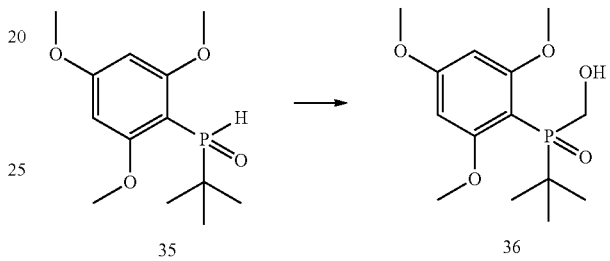

35     36

Example 36: tert-Butyl-(2,4,6-trimethoxyphenyl)(hydroxymethyl)phosphine oxide (36)

To the crude product 35 (60 g, 220 mmol) in water (100 mL) from previous step was added NaOH (13.2 g, 330 mmol, 1.50 eq) and 37% formaline solution (162 mL, 2200 mmol, 10 eq). The solution was heated to ~65° C. for 12 h. The mixture was cooled to room temperature. Concentrated hydrochloric acid (29.3 mL, 352.43 mmol, 1.6 eq) was added below 30° C. to adjust pH to 1. The mixture was extracted with $CH_2Cl_2$ (2×200 mL) and the combined extracts were concentrated to remove ~170 mL of solvents. The residual mixture was diluted with MeOH (150 mL) and treated with 2N HCl and heated to 52° C. for 1 h. The mixture was concentrated under reduced pressure. 2 Butanone (150 mL) was charged and the mixture was concentrated under reduced pressure. The desired product was crystallized from butanone/MTBE to give crystalline solid 36 (55.2 g, 83% yield).

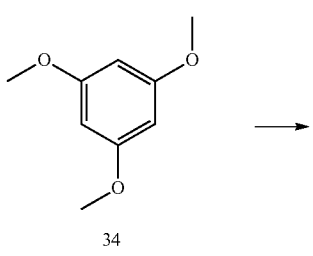 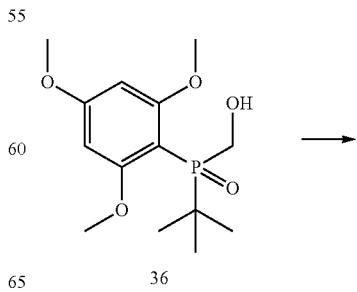

34     35     36

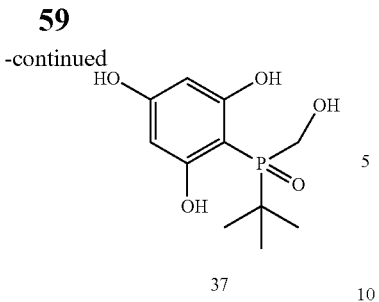

37

Example 37: tert-butyl(hydroxymethyl)(2,4,6-trihydroxyphenyl)phosphine oxide (37)

The mixture of tert-butyl(2,4,6-trimethoxyphenyl)phosphine oxide 36 (35.00 g, 0.16 mol) and 57% HI in water (337.76 g, 1.51 mol, 13 eq) was heated to 95° C. for 30 h. The mixture was cooled to rt and diluted with MeCN (30 mL). On cooling, a solution of NaOH (46.31 g, 1.16 mol, 10.00 eq) in water (60 mL) was slowly added and the resulting suspension was stirred at rt for 2 h. The solid was collected, rinsed with water and dried to give crude product 37 as off-white solid (26.00 g, 86%).

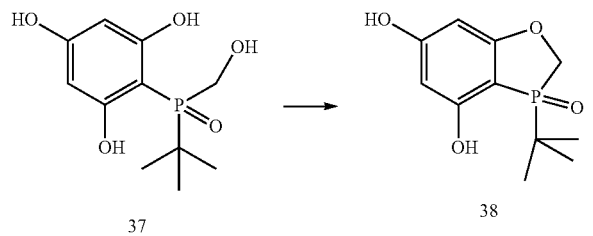 [SMILES: CC(C)(C)P(=O)(CO)c1c(O)cc(O)cc1O ; CC(C)(C)P1(=O)COc2cc(O)cc(O)c21]

Example 38: 3-(tert-butyl)-4,6-dihydroxy-2H-benzo[d][1,3]oxaphosphole 3-oxide (38)

To a mixture of the crude tert-butyl(hydroxymethyl)(2,4,6-trihydroxyphenyl)phosphine oxide 37 (48.60 g, 0.19 mol), THF (400 mL) and Et3N (94.49 g, 0.93 mol, 5.00 eq) at 0° C. was added MsCl (85.58 g, 0.76 mol, 4.00 eq) slowly. The resulting suspension was stirred at rt for 12 h. NaOH (52.29 g, 1.31 mol, 7.00 eq) in water (200 mL) was added. The mixture was stirred at 60° C. for 1 h, cooled, and neutralized with concentrated HCl (77 mL) in water (100 mL). THF was removed and resulting suspension was stirred at rt for 1 h. The solid was collected by filtration, rinsed with water and MeCN, and dried to give off-white solid product 38 (41.00 g, 91%).

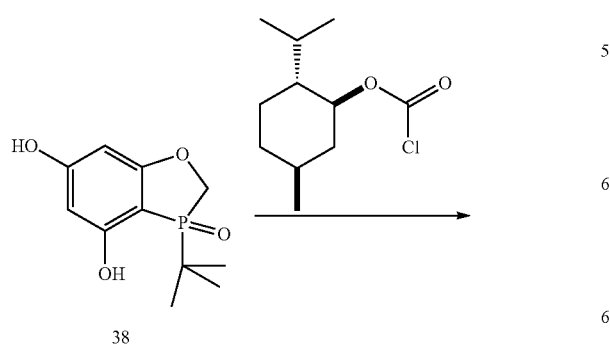

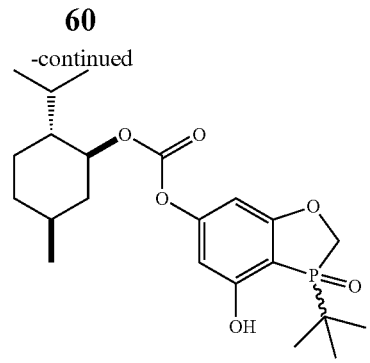

39

Example 39: 3-(tert-butyl)-4-hydroxy-3-oxido-2H-benzo[d][1,3]oxaphosphol-6-yl ((1S,2R,5S)-2-isopropyl-5-methylcyclohexyl) carbonate (39)

To a mixture of 3-(tert-butyl)-4,6-dihydroxy-2H-benzo[d][1,3]oxaphosphole 3-oxide (38, 41.00 g, 0.17 mol) and i-Pr₂NEt (72.69 mL, 0.42 mol, 2.50 eq) in MeCN (350 mL) was added (−)-menthyl chloroformate (86.62 mL, 0.41 mol, 2.40 eq). The suspension was warmed to and stirred at 60° C. for 1 h. EtOAc (500 mL) and water (300 mL) were added. The organic layer was separated and concentrated. The residue was filtered through silica gel and eluted with 50-80% EtOAc in hexane. The solution was concentrated to give oil (94%).

The oil (48.00 g, 79.24 mmol) was dissolved in THF (250 mL) and a solution of NaOH (7.92 g, 198.10 mmol, 2.5 eq) in water (75 mL) was added. The mixture was stirred at rt for 12 h. The organic layer was separated, diluted with EtOAc, washed with dilute HCl, and concentrated to dryness. The residue was triturated with MeCN (30 mL) to give 3-(tert-butyl)-4-hydroxy-3-oxido-2H-benzo[d][1,3]oxaphosphol-6-yl ((1S,2R,5S)-2-isopropyl-5-methylcyclohexyl) carbonatee (39) as white solid (18.95 g, 56%).

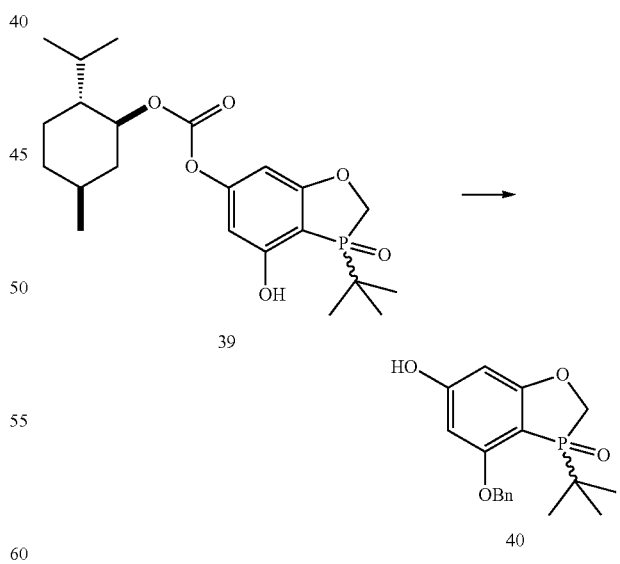

Example 40: 4-(benzyloxy)-3-(tert-butyl)-6-hydroxy-2H-benzo[d][1,3]oxaphosphole 3-oxide (40)

To a solution of 3-(tert-butyl)-4-hydroxy-3-oxido-2H-benzo[d][1,3]oxaphosphol-6-yl ((1S,2R,5S)-2-isopropyl-5- methylcyclohexyl) carbonate (39, 20.00 g, 47.12 mmol) in DMF (75 mL) was added $K_2CO_3$ (10.42 g, 75.39 mmol, 1.60 eq) and BnBr (12.89 g, 75.39 mmol, 1.60 eq). The mixture was stirred at rt for 1 h. Water (200 mL) and EtOAc (200 mL) were added. The organic layer was separated and concentrated. The residue was passed through a pad of silica gel, eluted first with hexane and then with 2% MeOH in EtOAc. The solution was concentrated to give desired intermediate (23.00 g, 95%). The intermediate (41.00 g, 79.83 mmol) was dissolved in THF (160 mL) and a solution of NaOH (7.98 g, 199.57 mmol, 2.50 eq) in water (50 mL) was added. The mixture was stirred at rt for 12 h for complete hydrolysis. The mixture was then neutralized with diluted HCl, and concentrated. The solid was collected and rinsed with water and heptane to give white solid product 40 (25.30 g, 98%).

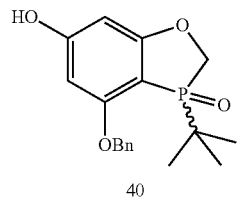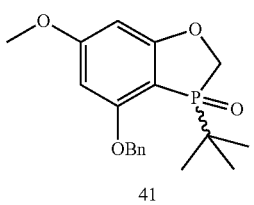

40

41

Example 41: 4-(benzyloxy)-3-(tert-butyl)-6-methoxy-2H-benzo[d][1,3]oxaphosphole 3-oxide (41)

4-(Benzyloxy)-3-(tert-butyl)-6-hydroxy-2H-benzo[d][1,3]oxaphosphole 3-oxide (40, 7.18 g, 21.60 mmol) was dissolved in DMF (35 mL). $K_2CO_3$ (5.97 g, 43.21 mmol, 2.00 eq) was added followed by MeI (2.69 mL, 43.21 mmol, 2.00 eq). The mixture was stirred at rt for 1 h, and quenched with water/EtOAc. The organic layer was separated and concentrated to give crude product 41 (7.50 g, 100%).

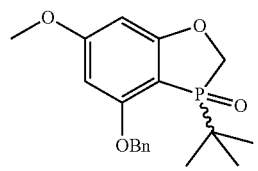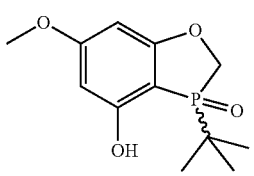

41

42

Example 42: 3-(tert-butyl)-4-hydroxy-6-methoxy-2H-benzo[d][1,3]oxaphosphole 3-oxide (42)

The crude 4-(benzyloxy)-3-(tert-butyl)-6-methoxy-2H-benzo[d][1,3]oxaphosphole 3-oxide (41, 10.70 g, 30.89 mmol) was dissolved in MeOH (50 mL). Palladium on carbon (10 wt %, 2.00 g) was added. The mixture was hydrogenated at 40° C. under 100 psi of $H_2$ for 3 h. The mixture was filtered, rinsed with MeOH and concentrated to dryness. The residue was triturated with MeCN (20 mL) to give white solid product 42 (6.40 g, 81%).

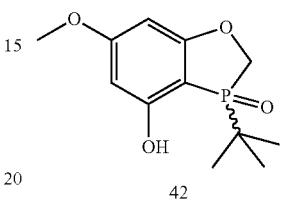

42

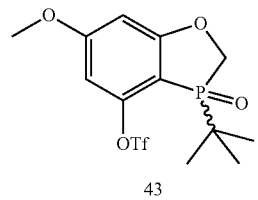

43

Example 43: 3-(tert-butyl)-6-methoxy-3-oxido-2H-benzo[d][1,3]oxaphosphol-4-yl trifluoromethanesulfonate (43)

Prepared using general procedure of Example 7 (5.01 g, 62%).

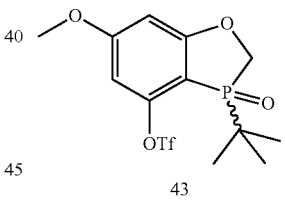

43

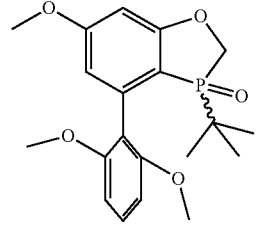

44

Example 44: 3-(tert-butyl)-4-(2,6-dimethoxyphenyl)-6-methoxy-2H-benzo[d][1,3]oxaphosphole 3-oxide (44)

A mixture of 3-(tert-butyl)-6-methoxy-3-oxido-2H-benzo[d][1,3]oxaphosphol-4-yl trifluoromethanesulfonate (43, 4.91 g, 12.64 mmol), (2,6-dimethoxyphenyl)boronic acid (4.60 g, 25.29 mmol, 2.00 eq), potassium fluoride (2.94 g, 50.58 mmol, 4.00 eq), Pd$_2$(dba)$_3$ (0.29 g, 0.32 mmol, 0.025 eq), XPhos (0.45 g, 0.95 mmol, 0.075 eq) and 1,4-dioxane (20 mL) was heated to reflux under argon for 16 h. The mixture was cooled and concentrated. NaOH (30%) was added to adjust pH to ~14 and the mixture was extracted with DCM. The extracts were dried over MgSO$_4$, filtered and and concentrated. The crude red oil was purified on silica gel (0-5% MeOH in DCM) and triturated with MTBE/hexane (1/2) to give white solid product 44 (2.99 g) in 63% yield. $^1$H NMR (400 MHz, CDCl$_3$) δ 7.29 (t, J=8.4 Hz, 1H), 6.66 (d, J=8.3 Hz, 1H), 6.56 (d, J=6.4 Hz, 1H), 6.49 (dd, J=2.4 Hz, 2.6 Hz, 1H), 6.40 (d, J=2.5, 2.5 Hz, 1H), 4.48 (dd, J=1.6, 13.7 Hz, 1H), 4.36 (dd, J=10.2, 13.7 Hz), 3.82 (s, 3H, 3.80 (s, 3H), 3.72 (s, 3H), 0.86 (d, J=15.9 Hz); $^{13}$C NMR (100 MHz, CDCl$_3$) 167.6, 164.7, 158.0, 139.0, 130.1, 117.6, 113.1, 106.4, 103.9, 97.1, 66.4, 56.2, 55.6, 55.5, 33.6, 23.9; $^{31}$P NMR (162 MHz, CDCl$_3$) δ −60.7.

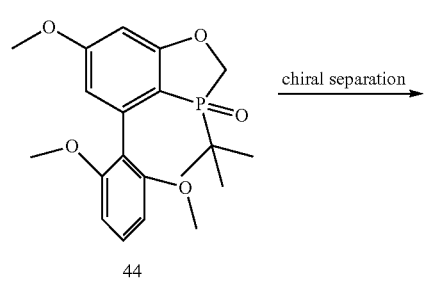

44 chiral separation →

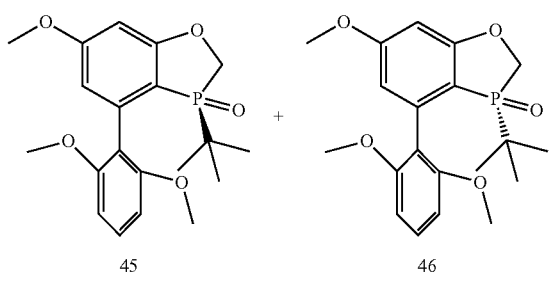

45            46

Example 45: Chiral separation of enantiomeric (4R)- and (4S)-3-(tert-butyl)-4-(2,6-dimethoxyphenyl)-6-methoxy-2H-benzo[d][1,3]oxaphosphole 3-oxide (45 and 46)

Analytical SFC method: Column: 4.6×100 mm Chiralcel OX-H from Chiral Technologies (West Chester, Pa.); CO2 Co-solvent (Solvent B): Methanol/Acetonitrile (1:3); Isocratic method: 25% Co-solvent at 4 mL/min.; System pressure: 125 bar; Column temperature: 40° C.; Sample diluent: MeOH; Retention time: 2.1 min(Isolate 1), 3.5 min (Isolate 2). Preparative SFC method: Column: 2.1×25.0 cm Chiralcel OX-H from Chiral Technologies (West Chester, Pa.); CO2 Co-solvent (Solvent B): Methanol/Acetonitrile (1:3); Isocratic method: 30% Co-solvent at 80 g/min; System pressure: 125 bar; Column temperature: 30° C.; Sample diluent: Methanol/Acetonitrile (1:3)

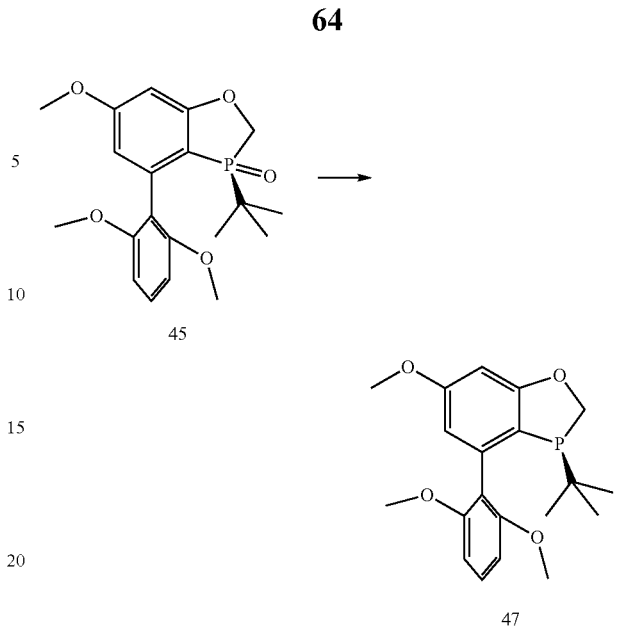

45

47

Example 46: (4s)-3-(tert-butyl)-4-(2,6-dimethoxyphenyl)-6-methoxy-2H-benzo[d][1,3]oxaphosphole (47)

Prepared using general procedure of Example 9. 1H NMR (400 MHz, DMSO) δ: 0.66 (d, J=12.0 Hz, 9H), 3.32 (s, 3H), 3.66 (s, 3H), 3.67 (s, 3H), 3.73 (s, 3H), 4.50 (dd, J=25.6, 12.4 Hz, 1H), 4.90 (dd, J=12.8, 1.6 Hz, 1H), 6.28 (t, J=2.4 Hz, 1H), 6.45 (d, J=2.0 Hz, 1H), 6.71 (dd, J=10.0, 8.4 Hz, 2H), 7.31 (t, J=8.4 Hz, 1H); 13C NMR (100 MHz, DMSO) δ: 26.8 (d, J=14 Hz), 31.0 (d, J=19 Hz), 55.9 (d, J=22 Hz), 56.0 (d, J=2 Hz), 71.3 (d, J=27 Hz), 95.4, 104.9 (d, J=46 Hz), 111.0 (d, J=56 Hz), 116.2 (d, J=12 Hz), 119.3, 129.7, 139.4 (d, J=19 Hz), 157.8 (d, J=76 Hz), 162.1, 165.2; 31P NMR (162 MHz, DMSO) δ: −10.2.

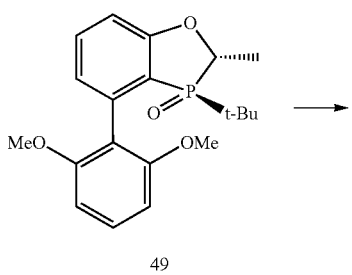

48

49

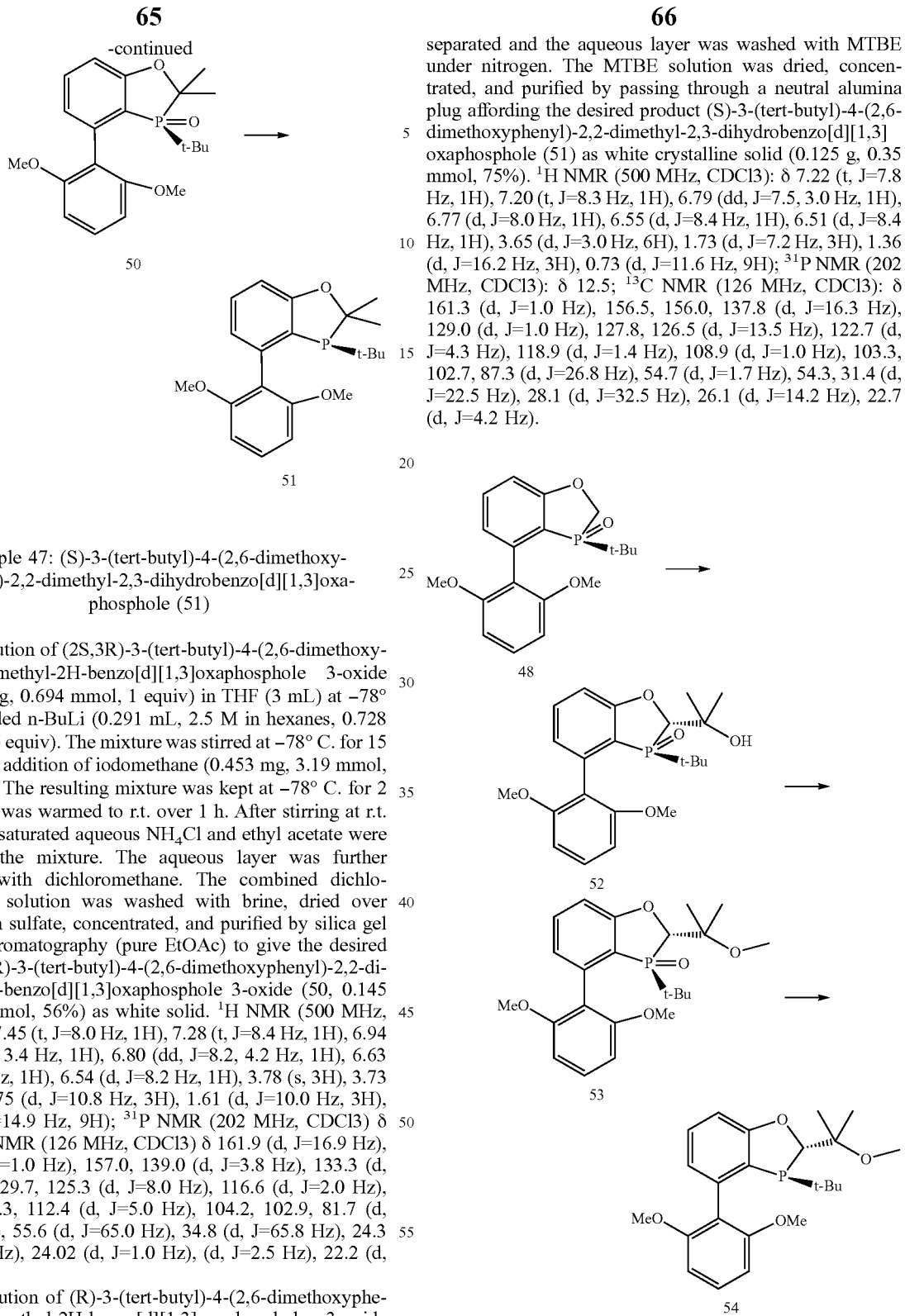

Example 47: (S)-3-(tert-butyl)-4-(2,6-dimethoxyphenyl)-2,2-dimethyl-2,3-dihydrobenzo[d][1,3]oxaphosphole (51)

To a solution of (2S,3R)-3-(tert-butyl)-4-(2,6-dimethoxyphenyl)-2-methyl-2H-benzo[d][1,3]oxaphosphole 3-oxide (49, 0.250 g, 0.694 mmol, 1 equiv) in THF (3 mL) at −78° C. was added n-BuLi (0.291 mL, 2.5 M in hexanes, 0.728 mmol, 1.05 equiv). The mixture was stirred at −78° C. for 15 min before addition of iodomethane (0.453 mg, 3.19 mmol, 4.6 equiv). The resulting mixture was kept at −78° C. for 2 h before it was warmed to r.t. over 1 h. After stirring at r.t. overnight, saturated aqueous $NH_4Cl$ and ethyl acetate were added to the mixture. The aqueous layer was further extracted with dichloromethane. The combined dichloromethane solution was washed with brine, dried over magnesium sulfate, concentrated, and purified by silica gel column chromatography (pure EtOAc) to give the desired product (R)-3-(tert-butyl)-4-(2,6-dimethoxyphenyl)-2,2-dimethyl-2H-benzo[d][1,3]oxaphosphole 3-oxide (50, 0.145 g, 0.387 mmol, 56%) as white solid. $^1$H NMR (500 MHz, CDCl3) δ 7.45 (t, J=8.0 Hz, 1H), 7.28 (t, J=8.4 Hz, 1H), 6.94 (dd, J=7.6, 3.4 Hz, 1H), 6.80 (dd, J=8.2, 4.2 Hz, 1H), 6.63 (d, J=8.4 Hz, 1H), 6.54 (d, J=8.2 Hz, 1H), 3.78 (s, 3H), 3.73 (s, 3H), 1.75 (d, J=10.8 Hz, 3H), 1.61 (d, J=10.0 Hz, 3H), 0.96 (d, J=14.9 Hz, 9H); $^{31}$P NMR (202 MHz, CDCl3) δ 61.7; $^{13}$C NMR (126 MHz, CDCl3) δ 161.9 (d, J=16.9 Hz), 158.7 (d, J=1.0 Hz), 157.0, 139.0 (d, J=3.8 Hz), 133.3 (d, J=2 Hz), 129.7, 125.3 (d, J=8.0 Hz), 116.6 (d, J=2.0 Hz), 116.0, 115.3, 112.4 (d, J=5.0 Hz), 104.2, 102.9, 81.7 (d, J=67.0 Hz), 55.6 (d, J=65.0 Hz), 34.8 (d, J=65.8 Hz), 24.3 (d, J=3.5 Hz), 24.02 (d, J=1.0 Hz), (d, J=2.5 Hz), 22.2 (d, J=4.0 Hz).

To a solution of (R)-3-(tert-butyl)-4-(2,6-dimethoxyphenyl)-2,2-dimethyl-2H-benzo[d][1,3]oxaphosphole 3-oxide (50, 0.175 g, 0.465 mmol) in THF (2.8 mL) at r.t. was added PMHS (0.18 g) and Ti(OiPr)4 (0.28 mL, 0.929 mmol, 2.0 equiv). The mixture was stirred at reflux for 12 h, and then concentrated under vacuum to remove most THF. 30% aqueous NaOH solution (2 mL) was carefully added to the residue. Gas was generated during addition. The resulting mixture was further stirred at 60° C. for 1 h. To the mixture at r.t. was added MTBE (3 mL). The MTBE layer was separated and the aqueous layer was washed with MTBE under nitrogen. The MTBE solution was dried, concentrated, and purified by passing through a neutral alumina plug affording the desired product (S)-3-(tert-butyl)-4-(2,6-dimethoxyphenyl)-2,2-dimethyl-2,3-dihydrobenzo[d][1,3] oxaphosphole (51) as white crystalline solid (0.125 g, 0.35 mmol, 75%). $^1$H NMR (500 MHz, CDCl3): δ 7.22 (t, J=7.8 Hz, 1H), 7.20 (t, J=8.3 Hz, 1H), 6.79 (dd, J=7.5, 3.0 Hz, 1H), 6.77 (d, J=8.0 Hz, 1H), 6.55 (d, J=8.4 Hz, 1H), 6.51 (d, J=8.4 Hz, 1H), 3.65 (d, J=3.0 Hz, 6H), 1.73 (d, J=7.2 Hz, 3H), 1.36 (d, J=16.2 Hz, 3H), 0.73 (d, J=11.6 Hz, 9H); $^{31}$P NMR (202 MHz, CDCl3): δ 12.5; $^{13}$C NMR (126 MHz, CDCl3): δ 161.3 (d, J=1.0 Hz), 156.5, 156.0, 137.8 (d, J=16.3 Hz), 129.0 (d, J=1.0 Hz), 127.8, 126.5 (d, J=13.5 Hz), 122.7 (d, J=4.3 Hz), 118.9 (d, J=1.4 Hz), 108.9 (d, J=1.0 Hz), 103.3, 102.7, 87.3 (d, J=26.8 Hz), 54.7 (d, J=1.7 Hz), 54.3, 31.4 (d, J=22.5 Hz), 28.1 (d, J=32.5 Hz), 26.1 (d, J=14.2 Hz), 22.7 (d, J=4.2 Hz).

Example 48: (2S,3S)-3-(tert-butyl)-4-(2,6-dimethoxyphenyl)-2-(2-methoxypropan-2-yl)-2,3-dihydrobenzo[d][1,3]oxaphosphole (54)

To a solution of (R)-3-(tert-butyl)-4-(2,6-dimethoxyphenyl)-2H-benzo[d][1,3]oxaphosphole 3-oxide (48, 0.50 g, 1.444 mmol, 1 equiv) in THF (5 mL) at −78° C. was added LDA (0.938 mL, 2.0 M in heptane/THF/chlorobenzene, 1.877 mmol, 1.3 equiv). The mixture was stirred at −78° C. for 30 min before addition of dry acetone (0.4 mL, 5.5 mmol, 3.8 equiv). The resulting mixture was kept at −78° C. for 2 h before it was warmed to r.t. over 1 h. After stirring at r.t. overnight, saturated aqueous NH4Cl and ethyl acetate were added to the mixture. The aqueous layer was further extracted with ethyl acetate. The combined ethyl acetate solution was washed with brine, dried over magnesium sulfate, concentrated to give the crude product (2S,3R)-3-(tert-butyl)-4-(2,6-dimethoxyphenyl)-2-(2-hydroxypropan-2-yl)-2H-benzo[d][1,3]oxaphosphole 3-oxide (52, 0.565 g, 1.4 mmol, 97%) as off-white solid. $^1$H NMR (400 MHz, CDCl3) δ 7.51 (t, J=10.0 Hz, 1H), 7.30 (t, J=10.5 Hz, 1H), 6.93 (dd, J=8.2, 3.6 Hz, 2H), 6.64 (d, J=8.4 Hz, 1H), 6.56 (d, J=8.4 Hz, 1H), 4.39 (s, 1H), 4.18 (d, J=2.4 Hz, 1H), 3.73 (s, 6H), 1.44 (s, 3H), 1.40 (s, 3H), 0.91 (d, J=15.6 Hz, 9H); $^{31}$P NMR (162 MHz, CDCl3) δ 65.7; $^{13}$C NMR (100 MHz, CDCl3) δ 164.3 (d, J=20.0 Hz), 158.6, 157.2, 138.5 (d, J=5.0 Hz), 134.5 (d, J=1.7 Hz), 130.0, 125.1 (d, J=8.4 Hz), 116.7 (d, J=2.0 Hz), 113.6, 112.7, 112.0 (d, J=5.7 Hz), 104.0, 103.0, 77.8 (d, J=60.5 Hz), 73.4 (d, J=2.0 Hz), 55.6 (d, J=13.6 Hz), 34.3 (d, J=70.4 Hz), 28.5 (d, J=6.5 Hz), 24.4 (d, J=2.5 Hz), 23.1.

To a solution of (2S,3R)-3-(tert-butyl)-4-(2,6-dimethoxyphenyl)-2-(2-hydroxypropan-2-yl)-2H-benzo[d][1,3]oxaphosphole 3-oxide (52, 0.50 g, 1.24 mmol, 1 equiv) in THF (5 mL) at 0° C. was added NaH (0.34 g, 60% dispersion in mineral oil, 1.5 mmol, 1.2 equiv). The mixture was stirred at 10° C. for 2 h before addition of iodomethane (0.38 g, 2.64 mmol, 2.1 equiv). The resulting mixture was warmed to r.t. over 1 h. After stirring at r.t. overnight, saturated aqueous NH4Cl and ethyl acetate were added to the mixture. The aqueous layer was further extracted with ethyl acetate. The combined organic solution was washed with brine, dried over magnesium sulfate, concentrated, and purified by silica gel column chromatography (0-100% EtOAc in hexanes) to give the desired product (2S,3R)-3-(tert-butyl)-4-(2,6-dimethoxyphenyl)-2-(2-methoxypropan-2-yl)-2H-benzo[d][1,3]oxaphosphole 3-oxide (53, 0.50 g, 1.2 mmol, 97%) as white solid. $^1$H NMR (500 MHz, CDCl3) δ 7.49 (t, J=8.0 Hz, 1H), 7.28 (t, J=8.3 Hz, 1H), 6.99 (dd, J=8.3, 3.5 Hz, 1H), 6.91 (dd, J=7.3, 3.2 Hz, 1H), 6.62 (d, J=8.4 Hz, 1H), 6.54 (d, J=8.4 Hz, 1H), 4.39 (s, 1H), 3.72 (d, J=6.4 Hz, 6H), 3.36 (s, 3H), 1.43 (s, 3H), 1.36 (s, 3H), 0.88 (d, J=15.6 Hz, 9H); $^{31}$P NMR (200 MHz, CDCl3) δ 58.8; $^{13}$C NMR (126 MHz, CDCl3) δ 163.8 (d, J=19.5 Hz), 158.8, 157.2, 138.5 (d, J=5.5 Hz), 134.2 (d, J=1.9 Hz), 129.7, 124.9 (d, J=8.6 Hz), 116.7 (d, J=2.2 Hz), 113.6, 112.8, 111.8 (d, J=5.8 Hz), 104.0, 102.9, 77.5, 77.2 (d, J=3.0 Hz), 55.5 (d, J=35.0 Hz), 49.3 (d, J=1.0 Hz), 34.1 (d, J=72.7 Hz), 23.3 (d, J=1.0 Hz), 20.3, 19.9 (d, J=1.6 Hz). To a solution of 3-(tert-butyl)-4-(2,6-dimethoxyphenyl)-2-(2-methoxypropan-2-yl)-2H-benzo[d][1,3]oxaphosphole 3-oxide (53, 0.44 g, 1.04 mmol) in THF (7 mL) at r.t. was added PMHS (0.45 g) and Ti(OiPr)4 (0.62 mL, 2.08 mmol, 2.0 equiv). The mixture was stirred at reflux for 12 h, and then concentrated under vacuum to remove most THF. 30% aqueous NaOH solution (5 mL) was carefully added to the residue. Gas was generated during addition. The resulting mixture was further stirred at 60° C. for 0.5 h. To the mixture at r.t. was added MTBE (5 mL). The MTBE layer was separated and the aqueous layer was washed with MTBE under nitrogen. The MTBE solution was dried, concentrated, and purified by passing through a neutral alumina plug affording the desired product (2S,3S)-3-(tert-butyl)-4-(2,6-dimethoxyphenyl)-2-(2-methoxypropan-2-yl)-2,3-dihydrobenzo[d][1,3]oxaphosphole (54) as white crystalline solid (0.418 g, 1.07 mmol, 100%). $^1$H NMR (400 MHz, CDCl3) δ 7.31-7.26 (m, 2H), 6.91 (d, J=7.9 Hz, 1H), 6.80 (d, J=4.6 Hz, 1H), 6.64 (dd, J=19.8, 8.2 Hz, 2H), 4.77 (s, 1H), 3.72 (d, J=3.0 Hz, 6H), 3.34 (s, 3H), 1.22 (s, 3H), 1.18 (s, 3H), 0.74 (d, J=12.0, 9H). $^{31}$P NMR (162 MHz, CDCl3) δ 1.8; $^{13}$C NMR (100 MHz, CDCl3) δ 164.6, 157.8, 156.9, 138.1 (d, J=17.6 Hz), 130.4, 128.9, 124.2 (d, J=13.9 Hz), 123.5 (d, J=4.0 Hz), 119.6, 109.1, 103.9 (d, J=57.4 Hz), 89.1 (d, J=30.7 Hz), 77.8 (d, J=19.0 Hz), 55.5 (d, J=18.4 Hz), 49.9, 31.1 (d, J=18.2 Hz), 26.6 (d, J=14.5 Hz), 21.3 (d, J=11.8 Hz), 20.8 (d, J=5.0 Hz).

Examples 49 to 53

Examples 49 to 53 illustrates how Ma can be prepared.

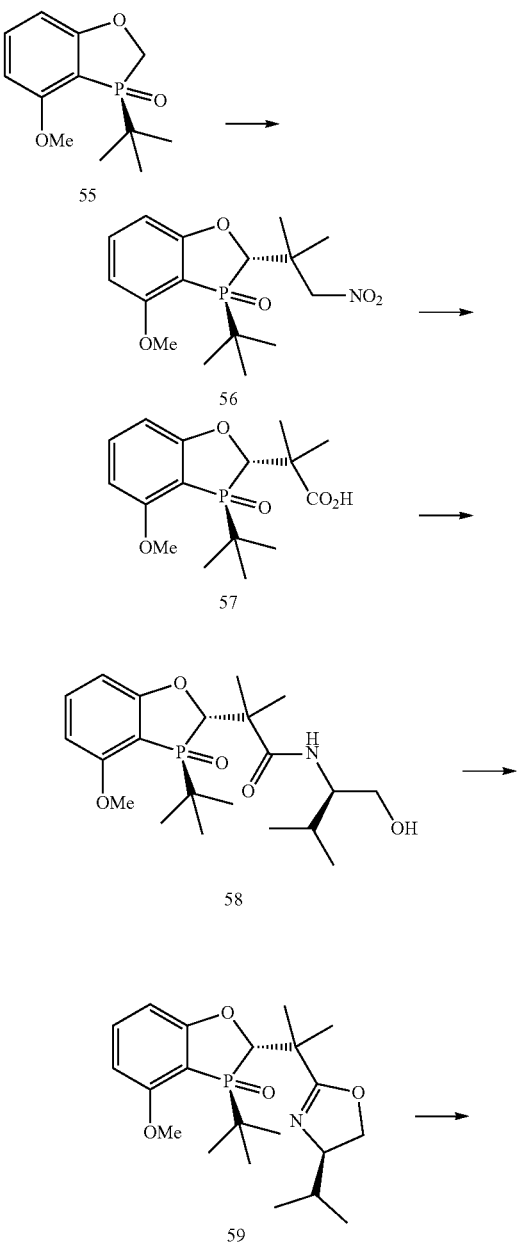

-continued

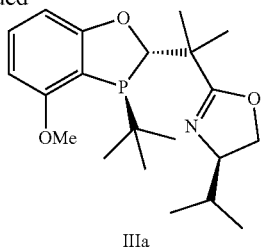

IIIa

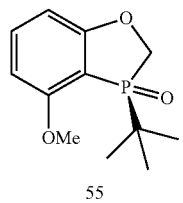

55

Example 49: (2S,3R)-3-(tert-butyl)-4-methoxy-2-(2-methyl-1-nitropropan-2-yl)-2H-benzo[d][1,3]oxaphosphole 3-oxide (56)

(R)-3-(tert-butyl)-4-methoxy-2H-benzo[d][1,3]oxaphosphole 3-oxide (55, 4.80 g, 19.98 mmol) was dissolved in THF and cooled to −75° C. A solution of 2 M LDA in THF/ethylbenzene (11.99 mL, 23.98 mmol, 1.2 eq) was added in 10 min and the resulting solution was stirred at −75° C. for 1 h. 2-Methyl-1-nitroprop-1-ene (0.21 g, 2.08 mmol, 1.00 eq) was added and the mixture was stirred at −75° C. for 1 h. The mixture was quenched with saturated NH4Cl, concentrated, and extracted with DCM. The combined extracts were washed with 0.5 M HCl, dried over MgSO4, and concentrated. The residue was purified on silica gel (50-80% EtOAc in hexane) to give (3R)-3-(tert-butyl)-4-methoxy-2-(2-methyl-1-nitropropan-2-yl)-2H-benzo[d][1,3]oxaphosphole 3-oxide as colorless oil (56, 2.92 g, 43%).

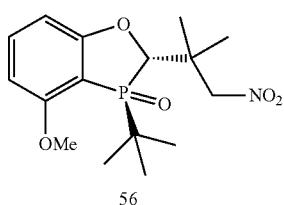

56

Example 50: 2-((2S,3R)-3-(tert-butyl)-4-methoxy-3-oxido-2H-benzo[d][1,3]oxaphosphol-2-yl)-2-methylpropanoic acid (57)

(3R)-3-(tert-Butyl)-4-methoxy-2-(2-methyl-1-nitropropan-2-yl)-2H-benzo[d][1,3]oxaphosphole 3-oxide (56, 3.40 g, 9.16 mmol) was dissolved in MeOH (60 mL). A solution of 1 N NaOH and 0.5 N Na2HPO4 in water (165 mL) was added and the mixture was stirred at rt for 1 h. Oxone (14.08 g, 22.91 mmol, 2.50 eq) in water (25 mL) was added and the mixture was stirred at rt for 10 h. The mixture was neutralized with 1N HCl to pH ~3, and extracted with DCM (3×100 mL). The combined extracts were dried over MgSO4, filtered and concentrated to give crude solid, which was suspended in MTBE (60 mL) at 50° C. for 0.5 h, cooled to rt, and filtered to give 2-((3R)-3-(tert-butyl)-4-methoxy-3-oxido-2H-benzo[d][1,3]oxaphosphol-2-yl)-2-methylpropanoic acid (57, 2.32 g, 78%).

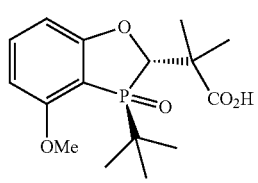

57

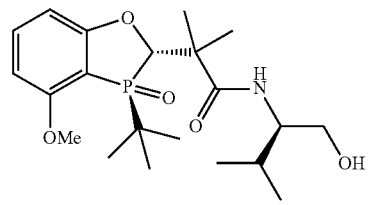

58

Example 51: 2-((2S,3R)-3-(tert-butyl)-4-methoxy-3-oxido-2H-benzo[d][1,3]oxaphosphol-2-yl)-N—((R)-1-hydroxy-3-methylbutan-2-yl)-2-methylpropanamide (58)

2-((3R)-3-(tert-butyl)-4-methoxy-3-oxido-2H-benzo[d][1,3]oxaphosphol-2-yl)-2-methylpropanoic acid (57, 0.50 g, 1.53 mmol) was dissolved in DCM (10 mL). Triethylamine (0.47 g. 4.60 mmol, 3.00 eq) and TBTU (0.68 g, 1.84 mmol, 1.20 eq) were added and the mixture was stirred at rt for 1 h. (R)-2-Amino-3-methylbutan-1-ol (0.18 g, 1.69 mmol, 1.10 eq) was added and the mixture was stirred at rt overnight. The mixture was concentrated and the residue was purified on silica gel and eluted with 0-5% MeOH in DCM as eluent to give 2-((3R)-3-(tert-butyl)-4-methoxy-3-oxido-2H-benzo[d][1,3]oxaphosphol-2-yl)-N—((R)-1-hydroxy-3-methylbutan-2-yl)-2-methylpropanamide (58, 0.57 g, 90%).

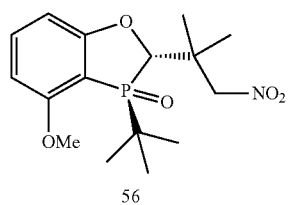

56

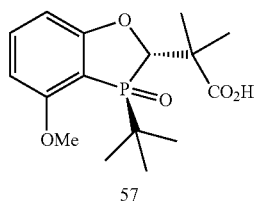

57

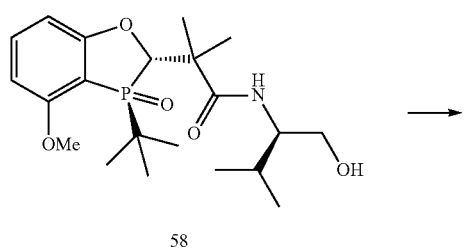

58

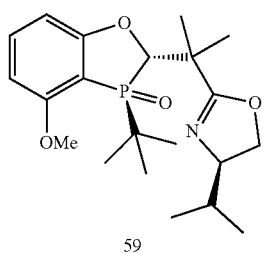

59

Example 52: (2S,3R)-3-(tert-butyl)-2-(2-((R)-4-isopropyl-4,5-dihydrooxazol-2-yl)propan-2-yl)-4-methoxy-2H-benzo[d][1,3]oxaphosphole 3-oxide (59)

To a chilled solution of (3R)-3-(tert-butyl)-2-(2-((S)-2-isopropyl-2,5-dihydrooxazol-4-yl)propan-2-yl)-4-methoxy-2H-benzo[d][1,3]oxaphosphole 3-oxide (58, 0.73 g, 1.38 mmol) in DCM (10 mL) was added Et$_3$N (2.09 g, 20.67 mmol, 15 eq) and MSCl (0.79 g, 6.89 mmol, 5.00 eq). The mixture stirred at rt for 2 days. The mixture was diluted with DCM (100 mL) and water (50 mL). The DCM layer was separated and washed with water (50 mL), dried over MgSO$_4$, filtered and concentrated. The residue was purified on silica gel and eluted with 0-5% MeOH in DCM to give (3R)-3-(tert-butyl)-2-(2-((S)-2-isopropyl-2,5-dihydrooxazol-4-yl)propan-2-yl)-4-methoxy-2H-benzo[d][1,3]oxaphosphole 3-oxide (59) as yellowish oil (0.51 g, 94%).

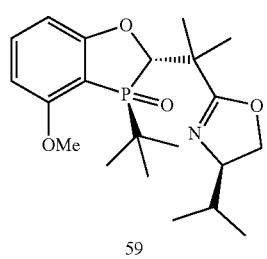

59

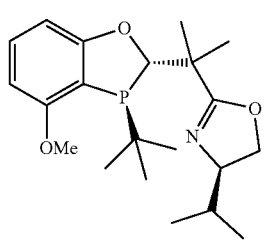

IIIa

Example 53: (R)-2-(2-((2R,3S)-3-(tert-butyl)-4-methoxy-2,3-dihydrobenzo[d][1,3]oxaphosphol-2-yl)propan-2-yl)-4-isopropyl-4,5-dihydrooxazole (IIIa)

(2S)-4-(2-((3S)-3-(tert-butyl)-4-methoxy-2,3-dihydrobenzo[d][1,3]oxaphosphol-2-yl)propan-2-yl)-2-isopropyl-2,5-dihydrooxazole (59, 0.21 g, 0.49 mmol) was dissolved in PhMe (10 mL). Et$_3$N (3.98 g, 39.30 mmol, 80.00 eq) and HSiCl$_3$ (1.00 g, 7.37 mmol, 15.00 eq) was added. The mixture was stirred at 100° C. for 16 h for complete reduction. The mixture was cooled to rt, and degased 30% NaOH (10 mL) was added. The resulting mixture was stirred at 60° C. for 1 h. The mixture was cooled and diluted with MTBE (100 mL). The organic layer was separated and washed with water (5 mL), concentrated to give the crude product IIIa. $^{31}$P NMR (162 MHz, CDCl$_3$) δ −7.4, which was directly used in preparation of iridium complex with [(Ir(COD)Cl)]$_2$ and sodium tetrakis(3,5-bis(trifluoromethyl)phenyl)borate.

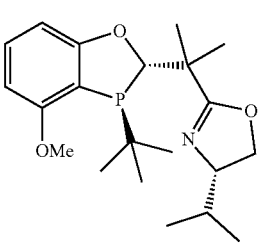

IIIb

Example 54: (4S)-2-(2-((3S)-3-(tert-butyl)-4-methoxy-2,3-dihydrobenzo[d][1,3]oxaphosphol-2-yl)propan-2-yl)-4-isopropyl-4,5-dihydrooxazole (IIIb)

Prepared using General Procedure from Example 49 to Example 53. $^{31}$P NMR (162 MHz, CDCl$_3$) δ −8.2.

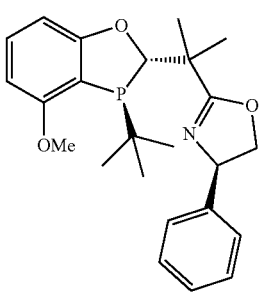

IIIc

Example 55: (4R)-2-(2-((3S)-3-(tert-butyl)-4-methoxy-2,3-dihydrobenzo[d][1,3]oxaphosphol-2-yl)propan-2-yl)-4-phenyl-4,5-dihydrooxazole (IIIc)

Prepared using General Procedure from Example 49 to Example 53. $^{31}$P NMR (162 MHz, CDCl$_3$) δ −7.4.

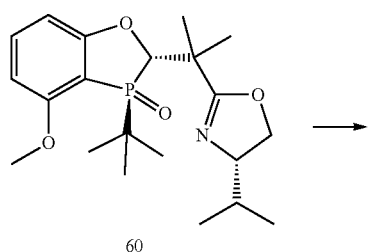

60

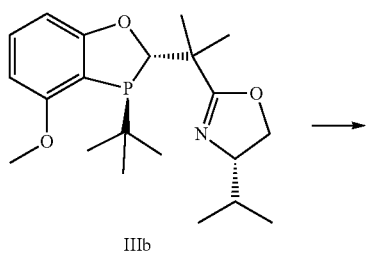

IIIb

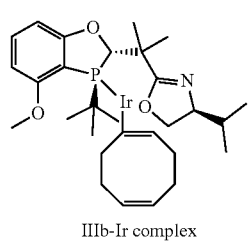

IIIb-Ir complex

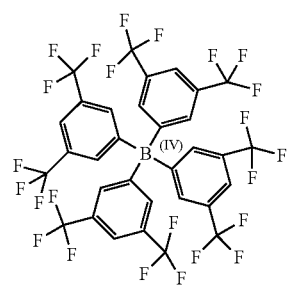

(IV)

Example 56: Preparation of IIIb-Ir Complex

An oven dried 50 mL Schlenk flask equipped with a magnetic stir bar was charged with phosphine oxide 60 (60 mg, 0.114 mmol) and toluene (5 mL). The solution was thoroughly degassed by vacuum purge-and-refill with argon before addition of 1.91 mL Et$_3$N (13.72 mmol) and 0.35 mL HSiCl$_3$ (3.43 mmol). The resulting mixture was heated to 100° C. for 14 h. A sample was taken for 31PNMR analysis. A single free phosphine was observed at −8.2 ppm. The mixture was cooled down to 0° C. with an ice bath and quenched with degassed 30% aqueous NaOH (5 mL) over 10 min. The resulting mixture was then stirred at 60° C. for 1 h. The mixture was cooled to room temperature and the layers were separated under argon. The aqueous layer was washed once with degassed MTBE. The combined organic was dried over MgSO$_4$ and concentrated. Degassed CH$_2$Cl$_2$ (10 mL) was added followed by 38.8 mg [Ir(COD)Cl]$_2$ (0.057 mmol) and 125.4 mg NaBArF (0.137 mmol). The mixture was stirred at room temperature for 12 h. LCMS indicated the formation of iridium complex cation: m/z: 676 (60%), 678 (100%). The mixture was diluted with 10 mL degassed CH$_2$Cl$_2$ and 10 mL degassed H$_2$O. The organic layer was dried over MgSO$_4$. The organic was passed through a short silica gel under Ar. The product was eluted along solvent front. The solvent was dried to give 82 mg orange solid product IIIb-Ir complex, 46% yield, $^{31}$P NMR (162 MHz, CDCl$_3$) δ 27.1 ppm.

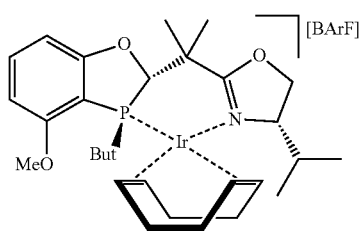

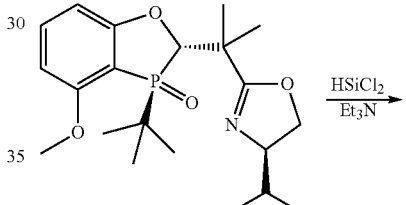

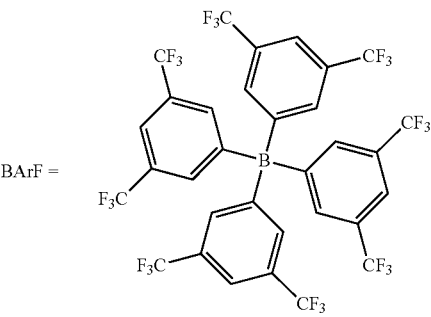

IIIa

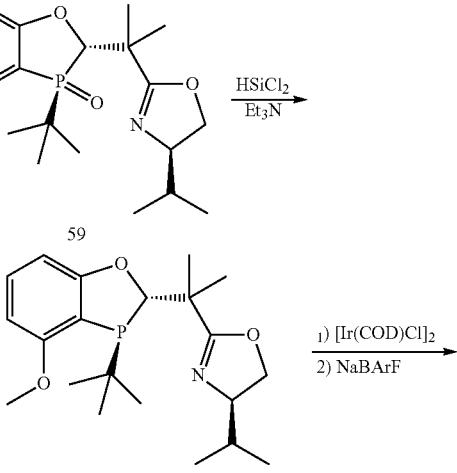

IIIa-Ir complex

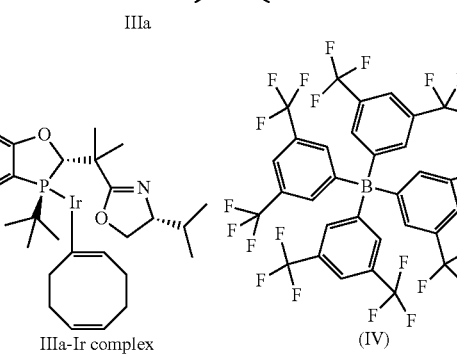

(IV)

Example 57: Preparation of IIIa-Ir Complex

Prepared using the general procedure of Example 56. 62% yield. $^{31}$P NMR (162 MHz, CDCl$_3$) δ 38.5 ppm.

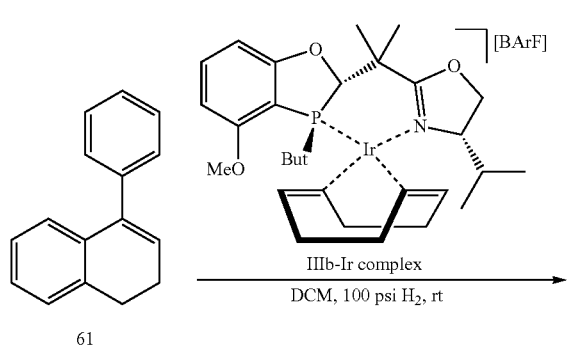

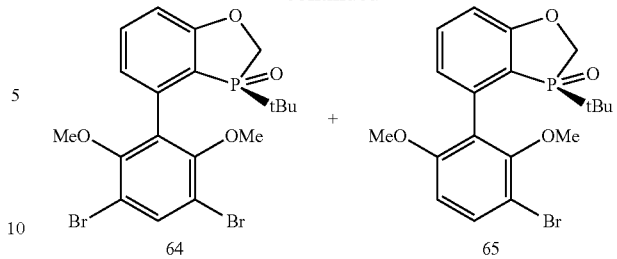

Example 59: (R)-3-(tert-butyl)-4-(3',5'-dibromo-2', 6'-dimethoxyphenyl)-2H-benzo[d][1,3]oxaphosphole 3-oxide (64)

(R)-3-(tert-butyl)-4-(2',6'-dimethoxyphenyl)-2H-benzo [d][1,3]oxaphosphole-3-oxide (63, 5.00 g, 14.44 mmol, 1 equiv) and acetonitrile (20 mL) are charged into a three necked bottom flask under $N_2$ atmosphere. The reaction stirred at ambient temperature. To the formed solution, N-bromosuccinimide (6.4 g, 36.1 mmol, 2.5 equiv) is added in three portions. The reaction mixture is stirred at 20° C. for 16 h to give 95:5 ratio of dibromo to monobromo products respectively. Water (20 mL) and EtOAc (40 mL) are added to the reaction mixture. The mixture stirred for 20 min then the organic fraction is separated, washed with 2N HCl (2×20 mL), dried over magnesium sulfate, filtered then concentrated. The crude product is purified by silica gel column chromatography (30% EtOAc in Hexanes) to provide the dibromo product 64 (5.75 g, 79% yield) as white solid. $^1$H NMR (400 MHz, CDCl$_3$) δ 7.79 (s, 1H), 7.51 (t, J=8.6 Hz, 1H), 7.00 (dd, J$_1$=8.6 Hz, J$_2$=3.3 Hz, 1H), 6.89 (dd, J$_1$=8.6 Hz, J$_2$=3.3 Hz, 1H), 4.58 (dd, J$_1$=14.8 Hz, J$_2$=1.8 Hz, 1H), 4.38 (dd, J$_1$=14.3 Hz, J$_2$=10.4 Hz, 1H), 3.71 (s, 3H), 3.68 (s, 3H), 1.03 (d, J=16.4 Hz, 9H); $^{31}$P NMR (162 MHz, CDCl$_3$) δ 62.62; $^{13}$C NMR (100 MHz, CDCl$_3$) δ 165.6 (d, J=18 Hz), 155.8, 154.7, 137.0 (d, J=6 Hz), 136.5, 133.8, 131.4, 124.0 (d, J=7 Hz), 114.8 (d, J=90 Hz), 113.8 (d, J=5 Hz), 113.0, 112.1, 65.9 (d, J=60 Hz), 61.6, 61.4, 33.9 (d, J=71 Hz), 23.7; m/z calcd for C$_{19}$H$_{22}$Br$_2$O$_4$P [M+H]$^+$: 502.9617, found: 502.9615.

Example 58: Hydrogenation of Alkenes using IIIb-Ir Complex.
1-phenyl-1,2,3,4-tetrahydronaphthalene (62)

To a glass vial were added 62 mg of 4-phenyl-1,2-dihydronaphthalene (61, 0.3 mmol) and 9.3 mg catalyst IIIb-Ir complex (0.006 mmol) and 3 mL of degassed DCM under argon. The vial was inserted into an Endeavor hydrogenation reactor. The reactor was then sealed and purged with $N_2$ three times and $H_2$ three times. The mixture was stirred under 100 psi $H_2$ pressure at room temperature for 20 h. Upon completion, the reactor was vented and the solvent was concentrated. The product was purified on silica using 100% hexanes to 5% CH$_2$Cl$_2$/hexanes to obtain the product 1-phenyl-1,2,3,4-tetrahydronaphthalene (62) as colorless oil after dryness, 50 mg, 80% yield, 50% ee; Enantioselectivity was determined on GC using a Chiraldex BP-H column: 30 m, 0.25 mm, 0.25 urn, 150° C., 1.0 mL/min, t$_1$=12.3 min, t$_2$=13.0 min; $^1$H NMR (400 MHz, CDCl$_3$) δ 7.32-7.36 (m, 2H), 7.24-7.28 (m, 1H), 7.14-7.18 (m, 3H), 6.81-6.91 (m, 3H), 4.03 (t, J=6.8 Hz, 1H), 2.78-2.84 (m, 1H), 2.70-2.76 (m, 1H), 2.04-2.10 (m, 1H), 1.74-1.84 (m, 2H), 1.61-1.69 (m, 1H).

(3R)-4-(3-bromo-2,6-dimethoxyphenyl)-3-(tert-butyl)-2H-benzo[d][1,3]oxaphosphole 3-oxide (65)

Identified by LCMS and $^{31}$P-NMR as mixture of interconverting atrop-isomers: $^{31}$P NMR (162 MHz, CDCl$_3$) δ 63.45; 63.28 ppm; m/z calcd for C$_{19}$H$_{23}$BrO$_4$P [M+H]$^+$: 425 (100%)-427 (97.3%), found: 425.0, 427.1.

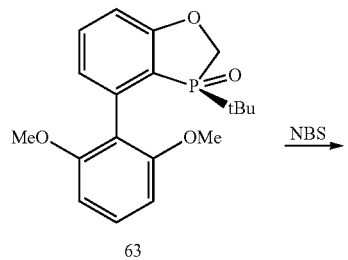

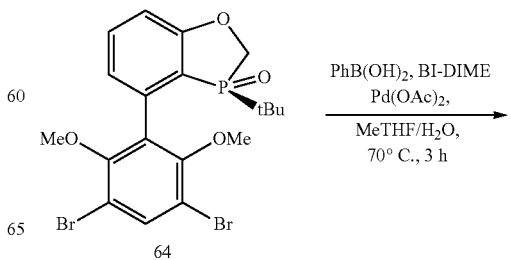

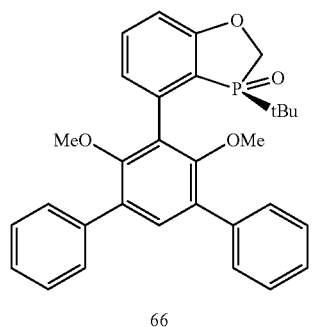

66

Example 60: (R)-3-(tert-butyl)-4-(2,6-dimethoxy-phenyl-3,5-diphenyl)-2H-benzo[d][1,3]oxaphosphole 3-oxide (66)

To a 250-mL reactor equipped with mechanical stirrer, condenser and argon line, (R)-3-(tert-butyl)-4-(3',5'-dibromo-2',6'-dimethoxyphenyl)-2H-benzo[d][1,3]oxaphosphole 3-oxide (64, 3.4 g, 6.7 mmol), phenylboronic acid (2.06 g, 16.86 mmol), Na$_2$CO$_3$ (2.14 g, 20.0 mmol), Pd(OAc)$_2$ (31.4 mg, 0.14 mmol) and racemic BI-DIME (46 mg, 0.14 mmol) are charged. The reactor is purged with argon for 5 minutes then MeTHF (20 mL) and H$_2$O (7 mL) are added. The resulting mixture is purged with argon for additional 20 min then heated to 70° C. for 3 h. HLPC analysis indicates >98% conversion. The mixture is cooled down to 20° C. then 20 mL H$_2$O is added. The layers are separated and the organic fraction washed with water (20 mL), dried over magnesium sulfate, filtered, concentrated then purified by silica gel column chromatography (30% EtOAc in Hexanes) to give the desired product 66 (3 g, 90% yield) as white solid; $^1$H NMR (400 MHz, CDCl$_3$) δ 7.7 (d, J=7.7 Hz, 2H), 7.56 (d, J=7.7 Hz, 2H), 7.50 (t, J=8.0 Hz, 1H), 7.45-7.25 (m, 7H), 6.97 (m, 2H), 4.58 (dd, J$_1$=14.1 Hz, J$_2$=2.0 Hz, 1H), 4.45 (dd, J$_1$=14.1 Hz, J$_2$=10.8 Hz, 1H), 3.32 (s, 3H), 3.24 (s, 3H), 1.11 (d, J=16.2 Hz, 9H); $^{31}$P NMR (162 MHz, CDCl$_3$) δ 62.67; $^{13}$C NMR (100 MHz, CDCl$_3$) δ 165.6 (d, J=19.3 Hz), 156.2, 155.0, 139.1 (d, J=6 Hz), 138.5, 138.1, 135.6, 134.0, 133.8 (d, J=2 Hz), 133.7, 132.7, 130.9, 130.5, 130.0, 129.2, 128.6, 128.5, 128.3, 128.0, 127.6, 127.2, 123.9 (d, J=7 Hz), 114.90 (d, J=90 Hz), 112.9 (d, J=5 Hz), 65.7 (d, J=60 Hz), 61.2, 61.0, 33.8 (d, J=71 Hz), 24.0; m/z calcd for C$_{31}$H$_{32}$O$_4$P [M+H]$^+$: 499.2033, found: 499.2057.

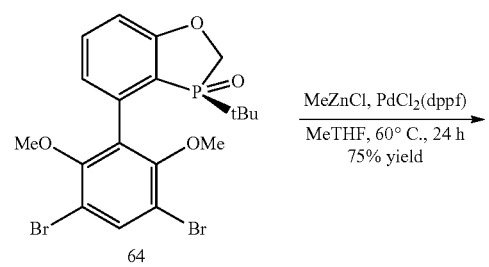

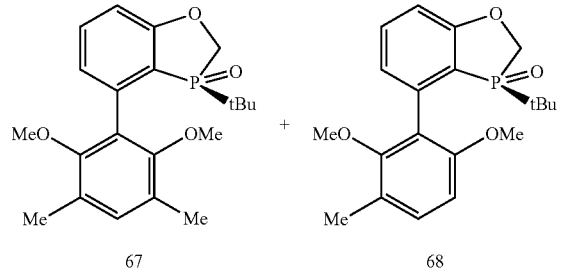

Example 61: (R)-3-(tert-butyl)-4-(2',6'-dimethoxy-3',5'-dimethylphenyl)-2H-benzo[d][1,3]oxaphosphole 3-oxide (67)

To a 100-mL reactor equipped with mechanical stirrer, condenser and argon line, (R)-3-(tert-butyl)-4-(3',5'-dibromo-2',6'-dimethoxyphenyl)-2H-benzo[d][1,3]oxaphosphole 3-oxide (64, 1.0 g, 2.0 mmol) and PdCl$_2$(DPPF) (162.0 mg, 0.2 mmol) are charged. The reactor purged with argon for 5 minutes then degassed MeTHF (10 mL) is added. The reaction mixture is purged with argon for additional 20 min then 2M solution of MeZnCl in THF (3 mL, 6 mmol) is added. The reaction mixture heated to 60° C. for 24 h to give 95:5 ratio of dimethylated product 67 to monomethylated product 68 respectively. The reaction cooled down to 20° C. then carefully quenched with water 20 mL H$_2$O. EtOAc (20 mL) is added. The mixture stirred for 10 minutes then the layers are separated. The organic fraction washed with 2N HCl (20 mL) then water (10 mL), dried over magnesium sulfate, filtered, concentrated, then purified by silica gel column chromatography (50% EtOAc in Hexanes) to give the desired product 67 (560 mg, 75% yield) as a colorless oil. $^1$H NMR (400 MHz, CDCl$_3$) δ 7.47 (t, J=7.9 Hz, 1H), 7.00 (s, 1H), 6.95 (m, 2H), 4.53 (dd, J$_1$=13.9 Hz, J$_2$=2.0 Hz, 1H), 4.36 (dd, J$_1$=13.8 Hz, J$_2$=10.6 Hz, 1H), 3.60 (s, 3H), 3.50 (s, 3H), 2.26 (s, 3H), 2.21 (s, 3H), 0.98 (d, J=16.1 Hz, 9H); $^{31}$P NMR (162 MHz, CDCl$_3$) δ 62.68; $^{13}$C NMR (100 MHz, CDCl$_3$) δ 165.5 (d, J=19.4 Hz), 155.3, 154.4, 139.3 (d, J=6 Hz), 133.4 (d, J=1.9 Hz), 133.3, 127.8 (d, J=2 Hz), 126.7, 125.9, 124.4 (d, J=8 Hz), 115.0 (d, J=90 Hz), 112.8 (d, J=5 Hz), 65.8 (d, J=61 Hz), 60.9, 60.6, 33.8 (d, J=71 Hz), 23.7, 16.1, 15.9; m/z calcd for C$_{21}$H$_{28}$O$_4$P [M+H]$^+$: 375.17, found: 375.1715.

(3R)-3-(tert-butyl)-4-(2,6-dimethoxy-3-methylphenyl)-2H-benzo[d][1,3]oxaphosphole 3-oxide (Monomethylated 68)

Formed by partial methylation and hydro-debromination reactions. The structure of 68 identified by LCMS and $^{31}$P-NMR as mixture of interconverting atrop-isomers: $^{31}$P NMR (162 MHz, CDCl$_3$) δ 79.01; 77.78 ppm; m/z calcd for C$_{20}$H$_{25}$O$_4$P [M+H]$^+$: 361.4, found: 361.2.

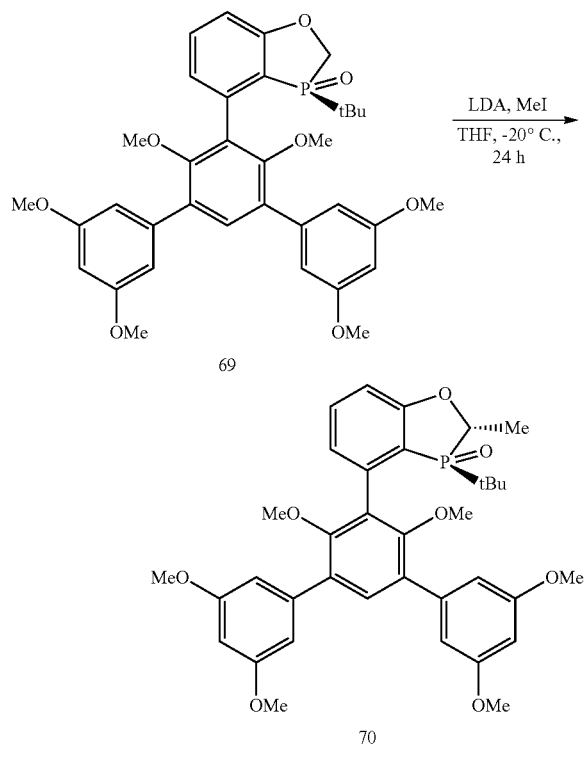 [SMILES: COc1cc(OC)cc(-c2cc(-c3cc(OC)cc(OC)c3)c(OC)c(-c3cccc4c3[P@](=O)(C(C)(C)C)CO4)c2OC)c1 ; COc1cc(OC)cc(-c2cc(-c3cc(OC)cc(OC)c3)c(OC)c(-c3cccc4c3[P@](=O)(C(C)(C)C)[C@@H](C)O4)c2OC)c1]

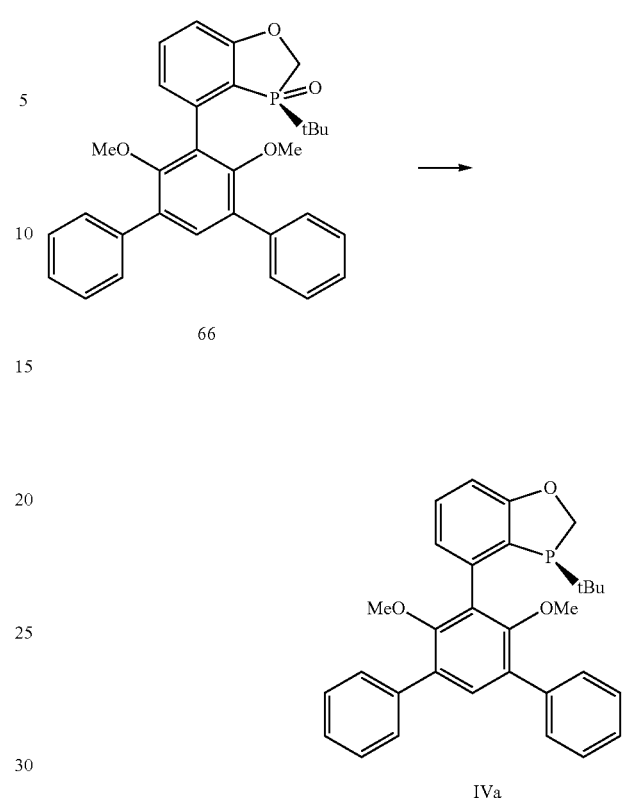

Example 62: (2S,3R)-3-(tert-butyl)-4-(3,3'',4',5,5'', 6'-hexamethoxy-[1,1':3',1''-terphenyl]-5'-yl)-2-methyl-2H-benzo[d][1,3]oxaphosphole 3-oxide (70)

To a 100-mL round bottom flask under argon atmosphere, the phosphine oxide 69 (700 mg, 1.13 mmol, 1 equiv) is added followed by addition of THF (10 mL). The resulted solution is cooled down to −78° C. then LDA (0.71 mL, 2.0 M in THF/toluene, 1.42 mmol, 1.25 equiv) is added via syringe in a rate that maintains the internal reaction temperature below −70° C. The mixture is stirred at −70° C. for 1 h then iodomethane (0.08 mL, 1.3 mmol, 1.2 equiv) is added drop wise. The resulting mixture is kept at −78° C. for 1 h then it is warmed to r.t. over 1 h. After stirring at r.t. 1.5 h, saturated aqueous NH$_4$Cl and ethyl acetate are added. The aqueous layer is further extracted with dichloromethane. The combined dichloromethane solution is washed with brine, dried over magnesium sulfate, filtered, concentrated, and purified by silica gel column chromatography (0-5% methanol in EtOAc) to give the desired product 70 (0.48 g, 67% yield) as a white solid. $^1$H NMR (500 MHz, CDCl$_3$) δ 7.50 (t, J=7.9 Hz, 1H), 7.37 (s, 1H), 6.93 (m, 2H), 6.79 (d, J=2.4 Hz, 2H), 6.72 (d, J=2.4 Hz, 2H), 6.45 (t, J=2.4 Hz, 1H), 6.44 (t, J=2.4 Hz, 1H), 4.58 (q, J=7.1 Hz, 1H), 3.80 (s, 12H), 3.40 (s, 3H), 3.34 (s, 3H), 1.61 (dd, J$_1$=11.9 Hz, J$_2$=7.2 Hz, 3H), 1.09 (d, J=15.6 Hz, 9H), $^{31}$P NMR (202 MHz, CDCl$_3$) δ 60.50; $^{13}$C NMR (125 MHz, CDCl$_3$) δ 164.3 (d, J=18 Hz), 160.8, 160.7, 156.3, 155.0, 140.6, 140.3, 139.4 (d, J=5 Hz), 133.8 (d, J=2 Hz), 133.5, 130.2, 129.4, 128.8, 128.7, 123.7 (d, J=8 Hz), 115.0 (d, J=90 Hz), 112.9 (d, J=5 Hz), 107.0, 106.8, 100.0, 99.4, 70.6 (d, J=63 Hz), 61.5, 61.1, 55.5, 55.4, 33.3 (d, J=71 Hz), 24.1, 15.0 (d, J=1.5 Hz); m/z calcd for C$_{36}$H$_{42}$O$_4$P [M+H]$^+$: 633.2612, found: 633.2639.

Example 63: (S)-3-(tert-butyl)-4-(4',6'-dimethoxy-[1,1':3',1''-terphenyl]-5'-yl)-2,3-dihydrobenzo[d][1,3] oxaphosphole (IVa)

Oxaphosphole oxide 66 (2.0 g, 4.0 mmol) is added to a 150 mL Schlenk flask equipped with magnetic stir-bar and reflux condenser. The reaction is inerted with Ar using three vacuum-purge cycles. Toluene (20.0 mL) is charged followed by triethylamine (2.2 mL, 16.0 mmol, 4 equiv) and HSiCl$_3$ (2.26 mL, 12.44 mmol, 3.1 equiv). The mixture is then heated at 55° C. and monitored by $^{31}$P NMR spectroscopy. After 3 h, the reaction is cooled to rt, quenched with 2 mL of degassed (Ar sparge) 30% NaOH, then vigorously stirred at rt for 1 h. The aqueous layer is removed and subsequently extracted under Ar with tert-butylmethyl ether (3×20 mL). The combined organics are dried over MgSO$_4$ under Ar then filter through argon-purged neutral alumina. The solvents are removed in vacuo to afford 1.66 g (86%) of desired product IVa as a white solid. $^1$H NMR (500 MHz, CDCl$_3$) δ 7.63 (d, J=8.0 Hz, 2H), 7.54 (d, J=7.9 Hz, 2H), 7.40 (t, J=7.4 Hz, 4H), 7.33, (m, 4H), 6.94 (m, 2H), 4.88 (dd, J$_1$=12.3 Hz, J$_2$=1.9 Hz, 1H), 4.60 (dd, J$_1$=25.4 Hz, J$_2$=12.3 Hz, 1H), 3.35 (s, 3H), 3.20 (s, 3H), 0.89 (d, J=12.3 Hz, 9H); $^{31}$P NMR (162 MHz, CDCl$_3$) δ −7.72; $^{13}$C NMR (100 MHz, CDCl$_3$) δ 163.7, 155.6, 154.9, 139.4 (d, J=18.1 Hz), 138.8, 138.5, 132.9, 131.0, 130.6 (d, J=1.3 Hz), 130.2, 130.1, 129.2, 128.7, 128.4, 128.2, 127.1, 126.9, 125.1 (d, J=15.2 Hz), 125.0, 123.0 (d, J=4 Hz), 109.8 (d, J=1.1 Hz), 70.6 (d, J=27 Hz), 61.2, 60.7 (d, J=2.7 Hz), 31.0 (d, J=19.3 Hz), 27.0 (d, J=14.6 Hz); HRMS (ES pos.): m/z calcd for C$_{31}$H$_{32}$O$_3$P [M+H]$^+$: 483.2083, found: 483.2080.

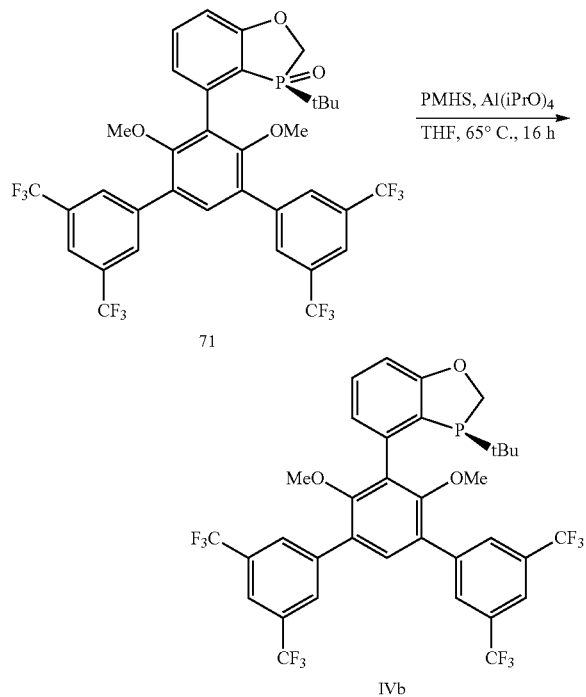

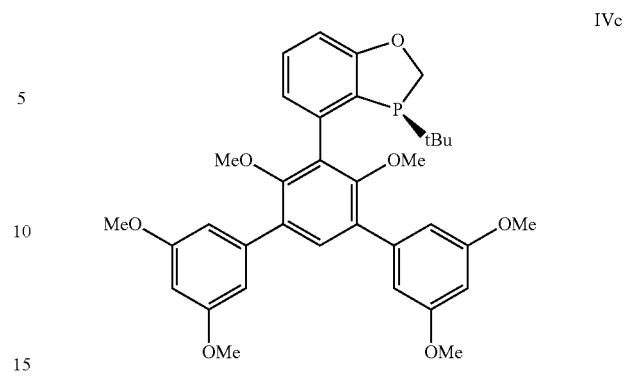

Example 64: (S)-3-(tert-butyl)-4-(4',6'-dimethoxy-3,3'',5,5''-tetrakis(trifluoromethyl)-[1,1':3',1''-terphenyl]-5'-yl)-2,3-dihydrobenzo[d][1,3]oxaphosphole (IVb)

Oxaphosphole oxide 71 (320 mg, 0.415 mmol) is added to a 50 mL Schlenk flask equipped with magnetic stir-bar and reflux condenser. The reaction is inerted with Ar using three vacuum-purge cycles. THF (10.0 mL) is charged followed by addition of PMHS (1.2 g) and titanium tetra-isopropoxide (282.5 mg, 0.66 mmol, 2.4 equiv) at 20° C. The reaction mixture is heated at 60° C. and monitored by $^{31}$P NMR spectroscopy. After 16 h, the reaction is cooled to rt, the THF removed under reduced pressure. The reaction then quenched by dropwise addition of degassed (Ar sparge) 30% NaOH (20 mL) followed by addition of tert-butylmethyl ether (20 mL), vigorously stirred at 60° C. for 1 h. The aqueous layer is removed and subsequently extracted under Ar with tert-butylmethyl ether (3×20 mL). The combined organics are dried over MgSO$_4$ under Ar then filter through argon-purged neutral alumina. The solvents are removed under reduced pressure to afford 274 mg (87.4%) of desired product IVb as a white solid. $^1$H NMR (400 MHz, CDCl$_3$) δ 7.98 (s, 2H), 7.94 (s, 2H), 7.81 (s, 2H), 7.30 (bs, 2H), 6.93 (m, 2H), 4.83 (d, J=14 Hz, 1H), 4.53 (dd, J$_1$=25.0 Hz, J$_2$=13 Hz, 1H), 3.31 (s, 3H), 3.18 (s, 3H), 0.83 (d, J=12 Hz, 9H); $^{31}$P NMR (162 MHz, CDCl$_3$) δ −8.58; $^{19F}$ NMR (376 MHz, CDCl$_3$) δ −62.70, −62.87; $^{13}$C NMR (100 MHz, CDCl$_3$) δ 164.1, 157.0, 156.3, 140.0 (d, J=22 Hz), 137.9, 137.7, 132.2, 132.0, 131.5, 131.2, 130.7, 129.4 (d, J=2 Hz), 129.0 (m), 128.8 (d, J=2 Hz), 128.0 (m), 124.9 (d, J=16.3 Hz), 124.7, 124.6, 122.8 (d, J=4 Hz), 122.0, 121.9 (m), 122.2, 110.7, 70.8 (d, J=29 Hz), 61.8, 61.2 (d, J=3 Hz), 31.1 (d, J=20 Hz), 26.8 (d, J=14 Hz); HRMS (ES pos.): m/z calcd for C$_{35}$H$_{28}$F$_{12}$O$_3$P [M+H]$^+$: 755.1579, found: 755.1572.

Example 65: (S)-3-(tert-butyl)-4-(3,3'',4',5,5'',6'-hexamethoxy-[1,1':3',1''-terphenyl]-5'-yl)-2,3-dihydrobenzo[d][1,3]oxaphosphole (IVc)

Prepared using General Procedure for Example 64. 58 mg product IVc was isolated as amorphous white solid in 60% yield. $^1$H NMR (400 MHz, CDCl$_3$) δ 7.27 (s, 1H), 7.26 (t, J=7.9 Hz, 1H), 6.85 (m, 4H), 6.70 (d, J=23 Hz, 2H), 6.63 (d, J=2.3 Hz, 2H), 6.38 (t, J=2.2 Hz, 2H), 4.79 (dd, J$_1$=12.6 Hz, J$_2$=2.1 Hz, 1H), 4.49 (dd, J$_1$=25.6 Hz, J$_2$=12.6 Hz, 1H), 3.75 (s, 6H), 3.73 (s, 6H), 3.34 (s, 3H), 3.22 (s, 3H), 1.08 (d, J=12.2 Hz, 9H); $^{31}$P NMR (162 MHz, CDCl$_3$) δ −8.64; $^{13}$C NMR (100 MHz, CDCl$_3$) δ 163.7, 160.7, 160.6, 155.6, 155.0, 140.7 (d, J=12.5 Hz), 139.5, 139.4, 132.6, 130.5, 130.3, 129.8, 125.0 (d, J=15.5 Hz), 122.9 (d, J=3.8 Hz), 109.9, 107.4, 106.8, 99.3 (d, J=2 Hz), 70.7 (d, J=27.6 Hz), 61.3, 61.0 (d, J=4 Hz), 55.4 (d, J=7.5 Hz), 31.0 (d, J=19.5 Hz), 30.3, 26.9 (d, J=14.7 Hz); HRMS (ES pos.): m/z calcd for C$_{35}$H$_{40}$O$_7$P [M+H]$^+$: 603.2506, found: 603.2497.

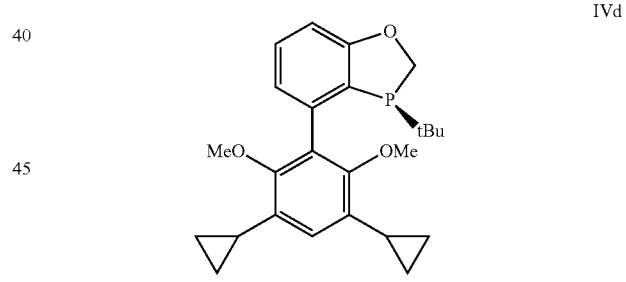

Example 66: (S)-3-(tert-butyl)-4-(3,5-dicyclopropyl-2,6-dimethoxyphenyl)-2,3-dihydrobenzo[d][1,3]oxaphosphole (IVd)

Prepared using General Procedure of Example 64. $^1$H NMR (500 MHz, CDCl$_3$) δ 7.31 (t, J=7.7 Hz, 1H), 6.97 (dd, J$_1$=7.2 Hz, J$_2$=3 Hz, 1H), 6.91 (d, J=8.2 Hz, 1H), 6.37 (s, 1H), 4.84 (dd, J$_1$=12.4 Hz, J$_2$=2.1 Hz, 1H), 4.57 (dd, J$_1$=25.8 Hz, J$_2$=12.4 Hz, 1H), 3.79 (s, 3H), 3.41 (s, 3H), 2.22 (m, 1H), 2.02 (m, 1H), 0.93 (m, 3H), 0.88 (m, 1H), 0.76 (m, 1H), 0.75 (d, J=12.2 Hz, 9H), 0.62 (m, 2H), 0.52 (m, 1H); $^{31}$P NMR (202 MHz, CDCl$_3$) δ −7.20; $^{13}$C NMR (125 MHz, CDCl$_3$) δ 163.7, 155.0, 154.3, 139.3 (d, J=18.1 Hz), 132.0, 131.4, 130.0 (d, J=1.1 Hz), 129.3 (d, J=1.1 Hz), 124.9 (d, J=15.2 Hz), 123.3 (d, J=4 Hz), 121.1, 109.7 (d, J=1.1 Hz), 70.6 (d, J=27 Hz), 61.7, 60.7 (d, J=2.7 Hz), 30.8 (d, J=19.0

Hz), 26.8 (d, J=14.8 Hz), 9.65, 9.07, 8.91, 8.41, 7.63, 7.2, 6.91; HRMS (ES pos.): m/z calcd for $C_{25}H_{32}O_4P$ [M+OH]$^+$: 427.20327, found: 427.2038.

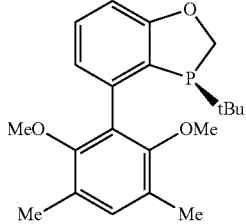

IVe

Example 67: (S)-3-(tert-butyl)-4-(4',6'-dimethoxy-3,3'',5,5''-tetrakis(trifluoromethyl)-[1,1':3',1''-terphenyl]-5'-yl)-2,3-dihydrobenzo[d][1,3]oxaphosphole 3-oxide (IVe)

Prepared using General Procedure of Example 63. $^1$H NMR (500 MHz, CDCl$_3$) δ 7.31 (d, J=7.7 Hz, 1H), 7.00 (s, 1H), 6.96 (dd, J$_1$=7.5 Hz, J$_2$=3.0 Hz, 1H), 6.92 (d, J=8.1 Hz, 1H), 4.84 (dd, J$_1$=12.4 Hz, J$_2$=1.5 Hz, 1H), 4.56 (dd, J$_1$=25.8 Hz, J$_2$=12.5 Hz, 1H), 3.68 (s, 3H), 3.32 (s, 3H), 2.27 (s, 3H), 2.24 (s, 3H), 0.75 (d, J=12.1 Hz, 9H); $^{31}$P NMR (202 MHz, CDCl$_3$) δ -7.26; $^{13}$C NMR (125 MHz, CDCl$_3$) δ 163.7, 155.0, 153.8, 139.3 (d, J=17.8 Hz), 132.5, 130.3 (d, J=1.1 Hz), 129.5 (d, J=1.1 Hz), 126.7, 126.3, 124.9 (d, J=15.2 Hz), 123.3 (d, J=4 Hz), 109.7 (d, J=1.1 Hz), 70.6 (d, J=27 Hz), 61.2, 60.2 (d, J=2.7 Hz), 30.8 (d, J=19.7 Hz), 26.8 (d, J=14.6 Hz); HRMS (ES pos.): m/z calcd for $C_{21}H_{28}O_3P$ [M+H]$^+$: 359.1770, found: 359.1770.

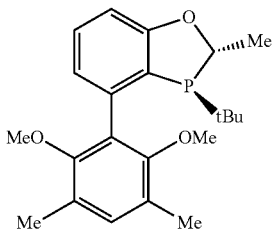

IVe

Example 68: (2S,3S)-3-(tert-butyl)-4-(2,6-dimethoxy-3,5-dimethylphenyl)-2-methyl-2,3-dihydrobenzo[d][1,3]oxaphosphole (IVg)

Prepared using General Procedure of Example 63. $^1$H NMR (500 MHz, CDCl$_3$) δ 7.31 (t, J=7.8 Hz, 1H), 6.91 (s, 1H), 6.86 (dd, J$_1$=7.4 Hz, J$_2$=3.2 Hz, 1H), 6.82 (d, J=8.2 Hz, 1H), 4.94 (q, J=7.2 Hz, 1H), 3.58 (s, 3H), 3.24 (s, 3H), 2.19 (s, 3H), 2.16 (s, 3H), 1.38 (dd, J$_1$=16.3 Hz, J$_2$=7.1 Hz, 3H), 0.69 (d, J=12.1 Hz, 9H); $^{31}$P NMR (202 MHz, CDCl$_3$) δ 11.02; $^{13}$C NMR (125 MHz, CDCl$_3$) δ 163.82, 154.95, 153.71, 139.7 (d, J=17 Hz), 132.4, 129.96, 129.5, 126.6, 126.1, 123.45 (d, J=4 Hz), 110.1, 78.7 (d, J=24 Hz), 61.1, 59.8, 30.9 (d, J=18.7 Hz), 26.9 (d, J=14.3 Hz), 21.8 (d, J=30.5 Hz), 16.26, 16.04; HRMS (ES pos.): m/z calcd for $C_{22}H_{30}O_3P$ [M+H]$^+$: 373.1927, found: 373.1926.

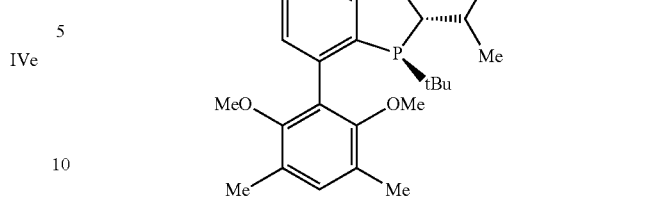

IVh

Example 69: (2S,3S)-3-(tert-butyl)-4-(2,6-dimethoxy-3,5-dimethylphenyl)-2-isopropyl-2,3-dihydrobenzo[d][1,3]oxaphosphole (IVh)

Prepared using General Procedure of Example 63. $^1$H NMR (500 MHz, CDCl$_3$) δ 7.27 (t, J=7.9 Hz, 1H), 6.97 (s, 1H), 6.88 (m, 2H), 4.67 (d, J=5.5 Hz, 1H), 3.66 (s, 3H), 3.24 (s, 3H), 2.26 (s, 3H), 2.23 (s, 3H), 2.03 (m, 1H), 1.0 (d, J=6.7 Hz, 3H), 0.97 (d, J=6.7 Hz, 3H), 0.74 (d, J=12.0 Hz, 9H); $^{13}$C NMR (125 MHz, CDCl$_3$) δ 164.5, 154.9, 154.0, 139.1 (d, J=17.4 Hz), 132.3, 129.7, 126.6, 126.0, 123.1 (d, J=4 Hz), 109.0, 89.1 (d, J=28.5 Hz), 61.1, 59.8, 34.0 (d, J=22.1 Hz), 30.5 (d, J=19 Hz), 29.7, 27.0 (d, J=14.7 Hz), 19.0, 18.8, 17.9, 17.8, 16.2, 16.0; $^{31}$P NMR (500 MHz, CDCl$_3$) δ 0.02; HRMS (ES pos.): m/z calcd for $C_{24}H_{34}O_3P$ [M+H]$^+$: 401.2240, found: 401.2241.

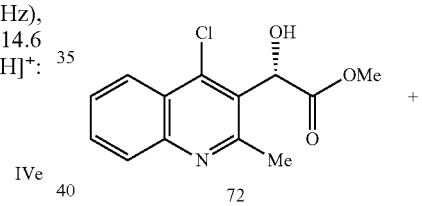

72

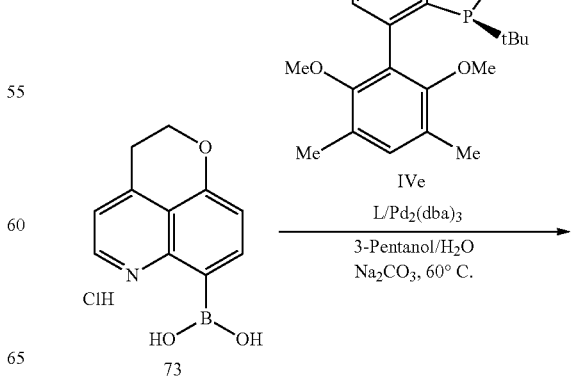

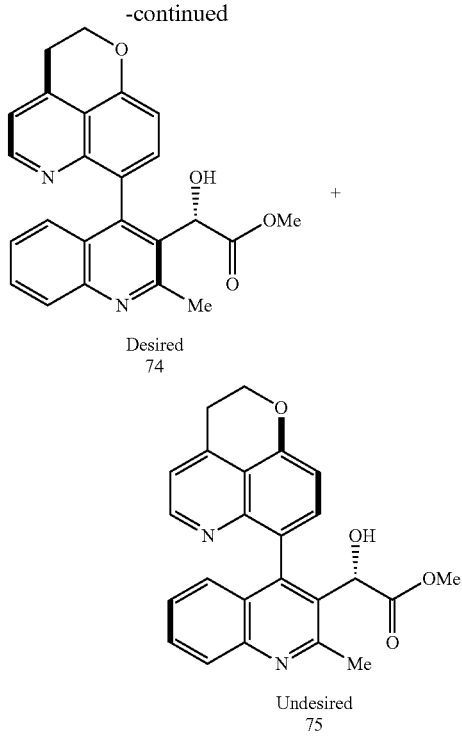

Desired
74

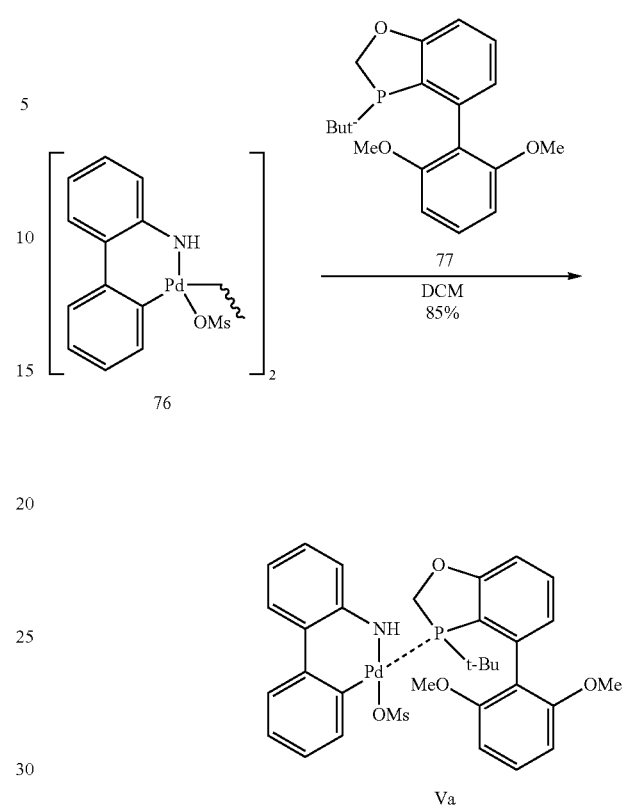

76

77
DCM
85%

Undesired
75

Example 70: Application of ligands IV. Methyl (2S)-2-(4-(2,3-dihydropyrano[4,3,2-de]quinolin-7-yl)-2-methylquinolin-3-yl)-2-hydroxyacetate (74)

Chloroquinoline 72 (0.75 mmol, 1 eq), boronic acid HCl 73 (0.83 mmol, 1.1 eq), Pd$_2$dba$_3$ (7.0 mg, 0.008 mmol), monophosphine ligand IVe (0.018 mmol), sodium carbonate (160 mg, 1.5 mmol), degassed 3-pentanol (1.6 mL), and degassed water (0.8 mL) are added to a 10 mL sealed vial. The mixture is degassed by sparging with argon for 10-15 min. The reaction is heated to 60-63° C. and agitated at this temperature for 16 h. The reaction is sampled for HPLC analysis to determine conversion and atroisomeric ratio. The mixture then cooled to 20° C. Water (2 mL) and EtOAc (10 mL) are added, the organic phase separated, washed with water, dried over MgSO$_4$, and then purified on silica column (0-5% MeOH/EtOAc). Refer to table 1 for diastereomeric ratios obtained with different ligands. The above procedure was applied on 2.0 g scale of quinolone 2 using phosphine ligand. 15:1 diastereomeric ratio of desired 74 to undesired 75 respectively, was obtained. 2.68 g of the major atropisomer 74 was isolated in 89% yield. Major isomer desired 74: $^1$H NMR (500 MHz, CDCl$_3$) δ 8.67 (d, J=4.3 Hz, 1H), 8.06 (d, J=8.3 Hz, 1H), 7.62 (t, J=7.2 Hz, 1H), 7.45 (d, J=7.8 Hz, 1H), 7.23 (t, J=8.4 Hz, 1H), 7.16 (d, J=4.4 Hz, 1H), 7.13 (d, J=8.1 Hz, 1H), 7.03 (d, J=8.1 Hz, 1H), 5.38 (d, J=7.5 Hz, 1H), 4.75 (bs, 1H), 4.75 (t, J=6.0 Hz, 2H), 3.40 (s, 3H), 3.34 (t, J=6.0 Hz, 2H), 2.93 (s, 3H); $^{13}$C NMR (125 MHz, CDCl$_3$) δ 173.64, 158.19, 153.98, 150.91, 147.46, 147.23, 145.35, 141.37, 133.13, 129.77, 129.46, 128.81, 127.81, 126.54, 126.46, 125.81, 118.05, 117.29, 109.90, 70.38, 65.85, 52.29, 28.64, 24.12; HRMS (ES pos.): m/z calcd for C$_{24}$H$_{21}$N$_2$O$_4$ [M+H]$^+$: 401.1496, found: 401.1502.

Example 71: Procedure for the Preparation of Palladacycle of Formula Va

A reaction vessel, equipped was charged with 76 (7.4 g, 10 mmol, 0.50 eq) and 77 (6.6 g, 20 mmol, 1.00 eq). The reaction vessel was evacuated and backfilled with nitrogen three times. DCM (100 mL) was charged and the resulting mixture was allowed to stir for 12 h. After completion, the reaction Mixture, a solvent switch to MTBE (100 mL) was performed and the resulting slurry was stirred for 1 h at room temperature. The resulting solid was isolated via filtration and the cake was washed with additional MTBE (20 mL). The solid was then dried under vacuum at 30° C. to afford Va with 85% yield. $^1$H NMR (400 MHz, DMSO) δ 7.56 (d, J=7.2 Hz, 1H), 7.50 (t, J=7.6 Hz, 1H), 7.42 (dd, J=8.0, 17.0 Hz, 1H), 7.37 (d, J=7.6 Hz, 1H), 7.30-7.15 (m, 3H), 7.09 (t, J=7.1 Hz, 1H), 7.00-6.93 (m, 1H), 6.92-6.83 (m, 3H), 6.82-6.70 (m, 3H), 5.76 (s, 2H), 4.65 (d, J=13.0 Hz, 1H), 3.93 (s, 3H), 3.65 (s, 3H), 2.32 (s, 3H), 0.76 (d, J=14.3 Hz, 9H); $^{31}$P NMR (162 MHz, CDCl$_3$) δ 37.3.

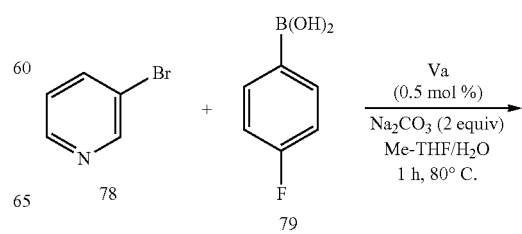

78

79

Va
(0.5 mol %)
Na$_2$CO$_3$ (2 equiv)
Me-THF/H$_2$O
1 h, 80° C.

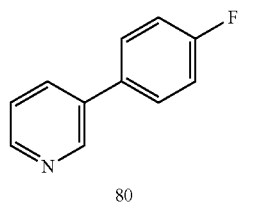

80

Example 72: Application of palladacycle Va. 3-(4-fluorophenyl)pyridine (80)

The base, boronic acid 79 and Va were charged to an inerted reactor. The reactor was evacuated and backfill with nitrogen twice. The agitation was initiated and pre-nitrogen-sparged Me-THF (50 mL) and water (12.5 mL) were charged. 3-bromopyridine was then charged. The batch was heated to about 85° C. (jacket temp, internal temp=75-77° C.) over 30 min-1 hour. The reaction mixture was agitated at that temperature for 3 hours or until full consumption of the starting material is observed. Water was charged to the reaction mixture and mixture was cooled down to room temperature. The layers were separated and the organic layer was washed again with water. The organic layer was distilled off and the crude mixture was purified by flash chromatography to provide 80 with 79% yield. $^1$H-NMR (400 MHz, CDCl3): 8.81 (d, J=1.5 Hz, 1H), 8.61 (d, J=4.8 Hz, 1H), 7.83 (d, J=7.8 Hz, 1H), 7.50 (dd, J=8.6, 5.1 Hz, 2H), 7.38 (dd, J=7.8, 4.7 Hz, 1H), 7.17 (dd, J=8.6, 8.7 Hz, 2H).

General procedure for ligands of formula VI:

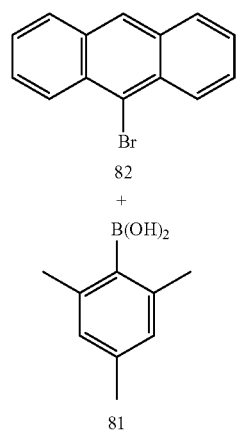

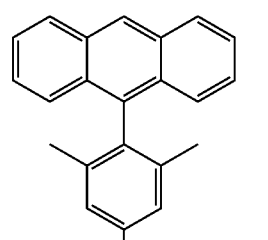

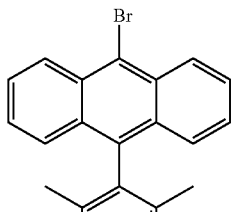

84

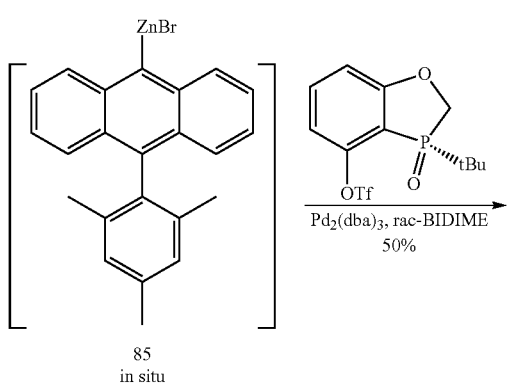

85
in situ

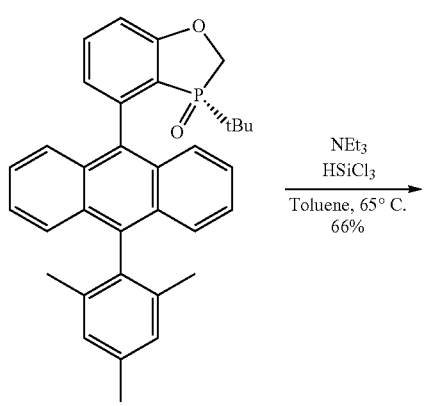

86

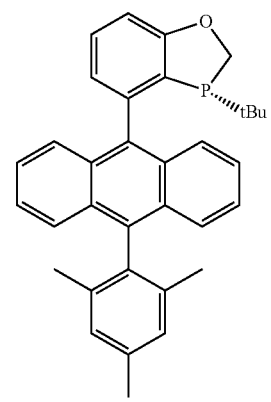

VIa

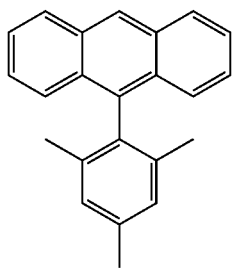

Example 73: 9-mesitylanthracene (83)

500 mL oven-dried round bottom flask charged with 9-bromoanthracene 82 (12.85 g, 50.0 mmol), 2,4,6-trimethylphenylboronic acid 81 (20.50 g, 125.0 mmol), PEPPSI-IPent (0.395 g, 0.5 mmol), potassium tert-butoxide (16.85 g, 150.0 mmol), activated powder 4 Å molecular sieves (2.50 g), t-BuOH (75 mL), and dioxane (75 mL). The mixture was stirred at 65° C. for 17 h. The mixture was then diluted with dioxane (200 mL), filtered through a plug of celite, concentrated in vacuo, and purified via flash column chromatography with hexane. The yield of the above reaction is 92%.

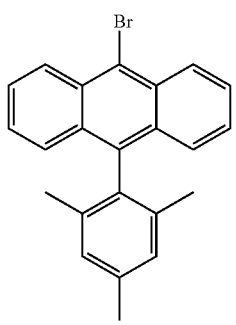

Example 74: 9-bromo-10-mesitylanthracene (84)

To an oven-dried 500 mL flask, 9-(2,4,6-trimethylphenyl)-anthracene 83 (10.2 g, 34.4 mmol) and CH$_2$Cl$_2$ (125 mL) were added. Br$_2$ (1.95 mL, 37.9 mmol, 1.1 equiv.) was added dropwise to the resulting solution over 5 minutes while stirring. The reaction mixture was allowed to stir for overnight at rt and quenched with saturated Na$_2$SO$_3$ (140 mL). The organic layer was separated. The aqueous layer was washed one more time with CH$_2$Cl$_2$ (3×100 mL). The combined organic layers were dried over anhydrous Na$_2$SO$_4$, concentrated in vacuo, made slurry with DCM (15 mL), filtered, washed with DCM (2×5 mL). The yield is 79%.

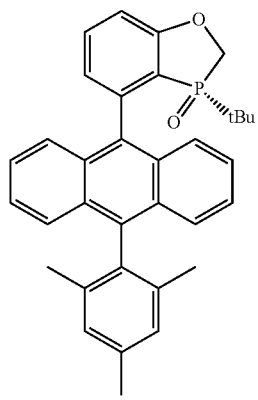

Example 75: 3-(tert-butyl)-4-hydroxy-2-methyl-2H-benzo[d][1,3]oxaphosphole 3-oxide (85)

A 100 mL 2-neck round-bottom flask with magnetic stir-bar and fitted with a reflux condenser with a short-path distillation head was purged with N$_2$. Then 9-bromo-10-mesitylantraene 84 (2.066 g, 5.51 mmol) and THF (7 mL) were charged to the flask. The solution was cooled to −78° C. in a dry ice acetone bath. t-BuLi (1.5 M in pentane, 7.2 mL, 10.74 mmol) was then added dropwise over 10 min. The resulting yellow slurry was stirred at −78° C. for 10 min and then allowed to warm to rt and stirred for an additional 15 min before use. ZnBr$_2$ (1.45 g, 6.45 mmol) in THF (5 mL). This solution was then transferred by cannula to the aryllithium reagent at rt, and the mixture was allowed to stir for an additional 20 min. A solution of triflate (1.0, 2.686 mmol), Pd$_2$(dba)$_3$ (0.049 g, 0.054 mmol), and rac-BIDIME (0.054 g, 0.1600 mmol) in THF (3 mL) was prepared in the glove box. The vial was sealed with a septum. The catalyst/triflate solution was then transferred to the ArZnBr solution using cannula transfer. The residue in the vial was rinsed with an additional THF (0.25 mL). The final mixture was then immersed in an oil bath at 70° C. heated for 12 h before analyzing it by UPLC/MS. Purification of the crude mixture by flash chromatography (gradient, 0 to 50% EtOAc in hexanes) resulted the product 85 (70%).

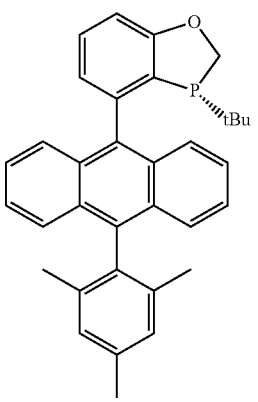

VIa

Example 76: (R)-3-(tert-butyl)-4-(10-mesitylanthracen-9-yl)-2,3-dihydrobenzo[d][1,3]oxaphosphole (VIa)

DCM (5 mL) was added to 3-(tert-butyl)-4-hydroxy-2-methyl-2H-benzo[d][1,3]oxaphosphole 3-oxide 86 (1.1 g, 4.58 mmol) under argon. Then triethylamine (1.15 mL, 8.25 mmol) was added to the mixture followed by trichlorosilane (1.64 g, 4.58 mmol). The reaction was stirred at rt for 16 h before analyzed by LCMS. The reaction was cooled down to 0° C. The reaction mixture washed with 2N NaOH (5 mL×2), then 1N HCl (5 mL×2), then with water (2 mL). Purification was done by column chromatography (from 0 to 50% ethylacetate to hexane) to yield 74% of VIa. $^1$H NMR (400 MHz, CDCl$_3$): δ 7.91 (d, J=8.80, 1H), 7.86 (d, J=8.72, 1H), 7.48-7.53 (m, 4H), 7.18 (ddd, J=9.4, J=3.22, J=0.90, 1H), 7.09-7.12 (m, 3H), 4.85 (dd, J=12.54, 2.10, 1H), 4.62 (dd, J=33.45, 12.60, 1H), 2.46 (s, 3H), 1.83 (s, 3H), 1.64 (s, 3H), 0.43 (d, J=12.24, 9H); $^{13}$C NMR (100 MHz, CDCl$_3$): δ 164.3, 142.5, 142.4, 137.5, 137.1, 136.3, 135.9, 134.8, 130.9, 130.8, 129.5, 129.4, 128.8, 128.2, 127.6, 127.6, 127.2, 126.4, 26.2, 126.0, 125.6, 125.3, 125.3, 125.2, 125.2, 110.5, 70.5, 30.7, 30.5, 26.9, 21.3, 19.8; 31P (162 MHz, CDCl$_3$): δ −9.1.

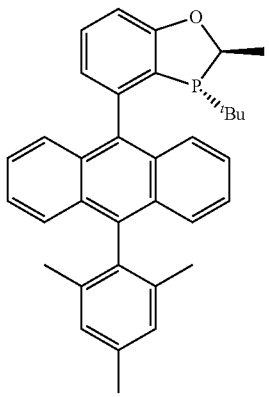 [SMILES: Cc1cc(C)c(-c2c3ccccc3c(-c3cccc4c3[P@@](C(C)(C)C)[C@H](C)O4)c3ccccc23)c(C)c1]

Example 77: (2R,3R)-3-(tert-butyl)-4-(10-mesitylanthracen-9-yl)-2-methyl-2,3-dihydrobenzo[d][1,3]oxaphosphole (VIb)

Prepared using general Procedure for formula VI. $^1$H NMR (400 MHz, CDCl$_3$): δ 7.93 (d, J=7.93, 1H), 7.81 (d, J=8.56, 1H), 7.48-7.54 (m, 3H), 7.28-7.41 (m, 4H), 7.15 (dd, J=6.62, 3.10, 1H), 7.08-7.12 (m, 3H), 5.03 (q, J=7.08, 1H), 2.46 (s, 3H), 1.83 (s, 3H), 1.63 (s, 3H), 1.51 (dd, J=16.59, 7.06, 3H), 0.43 (d, J=12.12, 9H); $^{13}$C NMR (100 MHz, CDCl$_3$): δ 163.4, 142.7, 137.5, 137.1, 136.3, 134.8, 131.0, 130.9, 130.7, 129.6, 129.4, 128.8, 128.7, 128.3, 128.2, 127.6, 127.6, 127.3, 126.2, 126.0, 125.6, 125.3, 125.2, 125.1, 125.0, 125.0, 110.9, 79.0, 68.2, 38.7, 30.4, 28.9, 27.0, 20.1, 19.7; 31P (162 MHz, CDCl$_3$): δ −9.96.

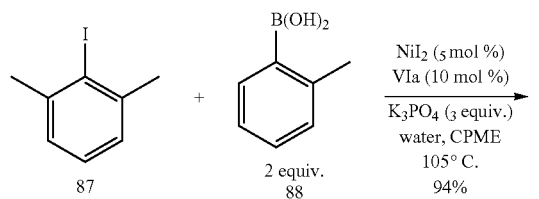

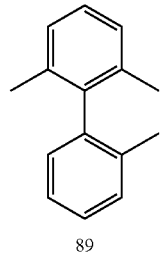

Example 78: Application of ligands with formula VI: 2,2',6-trimethyl-1,1'-biphenyl (89)

To a mixture of Ni-Cat. (0.0125 mmol NiI$_2$+0.025 mmol VIa) and Ar-I 87 (0.036 mL, 0.058 g, 0.25 mmol) 1.0 mL of CPME was added. The mixture was stirred for 10 mins. Then the water (0.02 mL, 0.02 g, 1.11 mmol) was added. To the mixture, boronic acid 88 (0.068 g, 0.5 mmol), bases (0.160 g, 0.75 mmol) were added. The reaction mixture was stirred at 105° C. (as mentioned) and aliquot was taken after different time interval to analyze the data by GC/MS. After that the reaction mixture was filtered through neutral alumina, concentrated under vacuum, purified by flash chromatography with hexane. $^1$H NMR (CDCl3, 400 MHz): δ 1.99 (s, 6H), 2.01 (s, 3H), 7.05-7.08 (m, 1H), 7.14-7.35 (m, 6H); $^{13}$C NMR (CDCl3, 100 MHz): δ 19.4, 20.3, 126.0, 126.9, 126.9, 127.2, 128.8, 130.0, 135.6, 135.8, 140.5, 141.0.

What is claimed is:

1. A compound of formula II

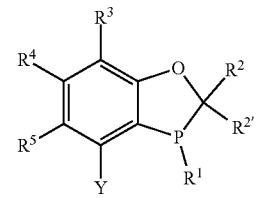

wherein,
Y=PR$^6$R$^7$, CR$^8$R$^9$, NR$^8$R$^9$, SR$^8$;

R$^1$, R$^6$ and R$^7$ are each independently selected from alkyl, cycloalkyl or optionally substituted aryl;

R$^2$ and R$^{2'}$ are each independently selected from the group consisting of hydrogen, halo, perhaloalkyl, —NR$^8$R$^9$, —OR$^8$, —SR$^8$, —Si(R$^8$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent R$^2$ and R$^{2'}$ taken together with the carbon atoms to which they are bound to form a substituted or unsubstituted cycloalkyl or heterocyclyl;

R$^3$, R$^4$, and R$^5$ are each independently selected from the group consisting of hydrogen, halo, perhaloalkyl, —NR$^8$R$^9$, —OR$^8$, —SR$^8$, —Si(R$^8$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$ alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, $R^8$ and $R^9$ are each independently selected from the group consisting of hydrogen, perhaloalkyl, alkyl, alkenyl, alkynyl, cycloalkyl, heterocycloalkyl, benzyl, aryl, and alkyl, and the enantiomers and diastereomers thereof.

2. The compound according to claim 1 wherein $R^1$ is $C_{1-6}$ alkyl;

$R^2$ and $R^{2'}$ are H;

$R^3$, $R^4$, and $R^5$ are H;

$R^6$ and $R^7$ are $C_{1-6}$alkyl or aryl;

and the enantiomers and diastereomers thereof.

3. The compound according to claim 1 wherein

Y is $PR^6R^7$ $R^1$ is t-butyl;

$R^2$ and $R^{2'}$ are H;

$R^3$, $R^4$, and $R^5$ are H;

$R^6$ and $R^7$ are t-butyl or phenyl;

and the enantiomers and diastereomers thereof.

4. The compound according to claim 1 selected from the group consisting of

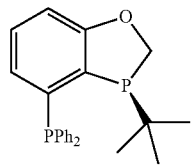

IIa and the enantiomers and diastereomers thereof.

5. A compound of formula III

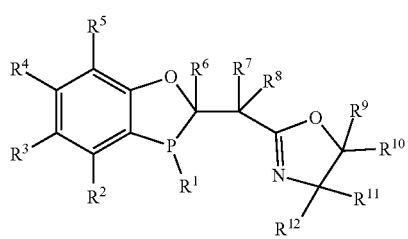

III wherein $R^1$ is selected from alkyl, cycloalkyl or optionally substituted aryl;

$R^2$, $R^3$, $R^4$, $R^5$, and $R^6$ are each independently selected from the group consisting of hydrogen, halo, perhaloalkyl, —NR$^{13}$R$^{14}$, —OR$^{13}$, —SR$^{13}$, —Si(R$^{13}$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted;

$R^7$, $R^8$, $R^9$, $R^{10}$, $R^{11}$ and $R^{12}$ are each independently selected from the group consisting of hydrogen, halo, perhaloalkyl, —NR$^{13}$R$^{14}$, —OR$^{13}$, —SR$^{13}$, —Si(R$^{13}$)$_3$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent $R^7$, $R^8$, $R^9$, $R^{10}$, $R^{11}$ and $R^{12}$ taken together with die carbon atoms to which they are bound to form a substituted or unsubstituted cycloalkyl, aryl or heteroaryl ring;

$R^{13}$ and $R^{14}$ are each independently selected from the group consisting of hydrogen, perhaloalkyl, alkyl, alkenyl, alkynyl, cycloalkyl, heterocycloalkyl, benzyl, aryl, and alkyl and the enantiomers and diastereomers thereof.

6. The compound according to claim 5 wherein $R^1$ is $C_{1-6}$alkyl, $C_{3-6}$cycloalkyl or optionally substituted aryl;

$R^2$, $R^3$, $R^4$, and $R^5$ are each independently selected from H or optionally substituted aryl or heteroaryl;

$R^6$ is H;

$R^7$ and $R^8$ are $C_{1-6}$ alkyl;

$R^9$, $R^{10}$, $R^{11}$ and $R^{12}$ are independently selected from H and $C_{1-6}$ alkyl;

and the enantiomers and diastereomers thereof.

7. The compound according to claim 5 wherein $R^1$ is $C_{1-6}$alkyl;

$R^2$, $R^3$, $R^4$, and $R^5$ are H;

$R^6$ is H;

$R^7$ and $R^8$ are $C_{1-6}$ alkyl;

$R^9$, $R^{10}$, $R^{11}$ and $R^{12}$ are independently selected from H and $C_{1-6}$ alkyl and the enantiomers and diastereomers thereof.

8. The compound according to claim 5 wherein $R^1$ is t-butyl;

$R^2$, $R^3$, $R^4$, and $R^3$ are H;

$R^6$ is H;

$R^7$ and $R^8$ are methyl;

$R^9$, $R^{10}$, $R^{11}$ and $R^{12}$ are independently selected from H and $C_{1-6}$ alkyl and the enantiomers and diastereomers thereof.

9. The compound according to claim 5 selected from the group consisting of

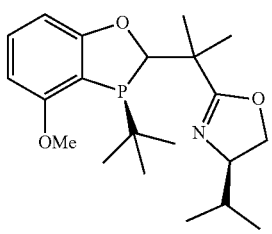

IIIa

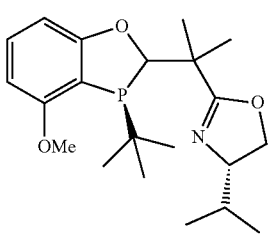

IIIb

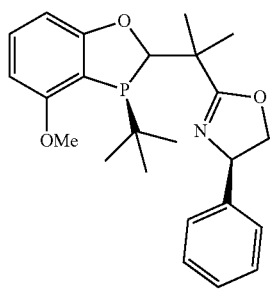
IIIc
and
and the enantiomers and diastereomers thereof.
* * * * *